US 6,605,696 B1

(12) United States Patent
Rosey

(10) Patent No.: US 6,605,696 B1
(45) Date of Patent: Aug. 12, 2003

(54) *LAWSONIA INTRACELLULARIS* PROTEINS, AND RELATED METHODS AND MATERIALS

(75) Inventor: Everett L. Rosey, Preston, CT (US)

(73) Assignees: Pfizer, Inc., New York, NY (US); Pfizer Products, Inc., Groton, CT (US)

( * ) Notice: Subject to any disclaimer, the term of this patent is extended or adjusted under 35 U.S.C. 154(b) by 0 days.

(21) Appl. No.: 09/689,065

(22) Filed: Oct. 12, 2000

Related U.S. Application Data

(60) Provisional application No. 60/160,922, filed on Oct. 22, 1999, and provisional application No. 60/163,868, filed on Nov. 5, 1999.

(51) Int. Cl.[7] .................. A61K 38/00; A61K 39/02; A61K 39/00; A61K 39/085; C07L 16/00
(52) U.S. Cl. .................. 530/300; 424/190.1; 424/192.1; 424/193.1; 424/243.1; 424/245; 424/252.1; 530/300; 530/324; 530/388.2
(58) Field of Search .................. 424/190.1, 192.1, 424/193.1, 243, 245, 252.1; 530/300, 324, 398.2

(56) References Cited

U.S. PATENT DOCUMENTS 5,885,823 A * 3/1999 Knittel et al. ............... 435/243

FOREIGN PATENT DOCUMENTS

| EP | 843818 | 12/1996 |
|---|---|---|
| WO | 9639629 | 12/1996 |
| WO | 9720050 | 6/1997 |
| WO | 0069903 | 11/2000 |
| WO | 0069904 | 11/2000 |
| WO | 0069905 | 11/2000 |
| WO | 0069906 | 11/2000 |

OTHER PUBLICATIONS

J.C. Boucher et al., *Journal of Bacteriology*, Jan. 1996 pp. 511–523 Two Distinct Loci Affecting Conversion to Mucoidy in *Pseudomonas aeruginosa* in Cystic Fibrosis Encode Homologs of the Serine Protease HtrA.
C. Dale et al. *Microbiology* 1998, 144, 2073–2084, Identification and sequencing of the groE operon and flanking genes of *Lawsonia intracellularis*: use in phylogeny.
Search Report: EP 00 30 9125.

* cited by examiner

*Primary Examiner*—Lynette R. F. Smith
*Assistant Examiner*—Vanessa L Ford
(74) *Attorney, Agent, or Firm*—Paul H. Ginsburg; Lorraine B. Ling; Kohn & Associates, PLLC

(57) ABSTRACT

Isolated polynucleotide molecules contain a nucleotide sequence that encodes a *L. intracellularis* HtrA, PonA, HypC, LysS, YcfW, ABC1, or Omp100 protein, a substantial portion of the sequences, or a homologous sequence. Related polypeptides, immunogenic compositions and assays are described.

5 Claims, 8 Drawing Sheets

FIG. 2

```
Li_Ycfw    ---MKFELFIALHYLFARRKQAFIYLISLMSILGVAIGVASLVVVLGVYNGFTIDIRDKI  57
AJ235272   MINNNFSFNIAFRYFRAKKNEKFVSIIAAFSLVGVMIGVAALIVVMSVMNGFHLELTKNI  60
             :*.: **::*: *:::: *: :*: :*::** ****:*:**..* *** :::  .:*

Li_Ycfw    LGANAHIIITGNFDSPIEEPTSFTQLSTTSMLSQNALIILNKLQQTSAIIGATPFIYAEC  117
AJ235272   IGLNGDIVINRQGDN-----IDNYEEIKTTLLKQDYVKHVTYIAHGQALALGK-------  158
           :* *..*:*.  : *.       . : .*::*.*: :  :. : : .*:    ..

Li_Ycfw    MISSPHGVKGLILRGIDPSSAQNVISMLSHLTKGNLEDLIPKVLGTPDGIIIGNELAQRL  177
AJ235272   ---SNN--SGVLVKGIKLNDLSLRNGIFKNVNFGSFDNFHGKNV-----IALGEQLASNL  158
              *  :  .*:::::**. ... .  .::::.. *.:::: * :    * :*::**..*

Li_Ycfw    NVTIGSRVNLLSPTGQKTSSGFQPRIRPLIVTGIFHTGMFEYDTSLAFTSLNAARELLGL  237
AJ235272   GVTVGEKLRLISPNSVSTAFGSIPRSKEFQIIAIFNSGMYDYDLTTILMPLTAAQNFLSL  218
           .**:*.::.*:.**.. .*: * ** : : .**::**::** :  : .*.**::*.*

Li_Ycfw    PHYTISGIEVSIHDVYQANYITNQLQQELGHNFSVRSWMDMNANLFAALKLEKIGMFIIL  297
AJ235272   G-NDINSIEINSLDPDQAITYSYKIQSLLGPNLYVFNWKTLNSQFLSALAVERTAMFTIL  277
              * *..**:.. * ** :  : ::*. ** **  :* .* :*:::::** :*: .** **

Li_Ycfw    AMVVLIGSFSIVTTLIMLVMEKTRDIAILTSMGATSQMIRRIFILQGTIIGIVGTLLGYL  357
AJ235272   SLIITVAAFNIISNLFMLVKDKTSDIAILRTMGASTKQIMVIFIYNGMFIGLLGTTLGVI  337
           ::::  :..*.*::.*:*:.*** ***** :****:.:** ** : :    * *** :* :**::** **  :

Li_Ycfw    LGITLALLLQKYQ--------FIKLPPGVYTIDHLPVLLNWLDIFIIGTSAMLLCFFATL  409
AJ235272   LGVTFSYNIQTIKNYLERITGIKIFEAAIYFLYSLPSKVKTDDIILITSLSIILCFLATI  397
           **:*::  :*. :          :  : ..:* :  **  :: **:*.* ::::***:**:

Li_Ycfw    YPAHQAARLQPIEGLRYE  427
AJ235272   YPSYRASKLNPVDALRYE  415
           **::.:*:.*.:: .****
```

FIG. 3

```
Li_ABC1    MSQYLLENIVKQYDSPSEPICVLHKINLSIAHGESLAIIGFSGSGKSTLLHILGALDIPS    60
AE000212   ---MQCDNLCKRYQEGSVQTDVLHNVSFSVGEGEMMAIVGSSGSGKSTLLHLLGGLDIPT   57
                :*::*:   .*::   *  :*:::..:.**  ****.*******:**:.* ***  *

Li_ABC1    SGTVLFNNKNLSHMGPNEKACFRNKLLGFIFQFHNLLPEFSAEENVAMKALIAGIPKKKA  120
AE000212   SGDVIFNGQPMSKLSSAAKAELRNQKLGFIYQFHHLLPDFTALENVAMPLLIGKKKPAEI  117
           **.*:**   :*:  . ::.* **:****::***:***:*:* *****  *:* **

Li_ABC1    LLLAREALGSVGLENKYHHRITMLSGGERQRVAIARAILLFPQVLLADEPTGNLDQKTGE  180
AE000212   NSRALEMLKAVGLDHRANHRPSELSGGERQRVAIARALVNNPRLVLADEPTGNLDARNAD  177
             .* * :.:***::: :**   *:**********::.:*::***********:  .:

Li_ABC1    HIANLLISLNKTFNITLIVVTHNNDIAHSMGRCLELKSGDLHDKTPEYISSTVTV      235
AE000212   SIFQLLGELNRLQGTAFLVVTHDLQLAKRMSRQLEMRDGRLTAELSLMGAE----      228
            *  ** .**:  .:**:****:  :*:  .**:**::**      .::.*
```

FIG. 4

```
Li_OMP100  MTKRLNIFLLLLLCNILYCNIIANAASKDDPSIVVLPFQINGSSNDEELQTELPMLLATA  60
U70214     ------------------------------------------------------------

Li_OMP100  LKNKGFRVIPNKSALNLLYKQNISQLNISTAKKVAQQLHADYVVYGSFNQTGENFSIDSR  120
U70214     ------------------------------------------------------------

Li_OMP100  LIDSTGVASARPLYIEKPKFNELNIAVTELAERISNGLIKKNTIADVRIHGLKVLDPDVI  180
U70214     ----------------MAMKKLLIASLLFSSATVYG-AEGFVVKDLHFEGLQRVAVGAA   42
                           :::* **  ::.   *  :  .: *:::.**: :   ..

Li_OMP100  LTRLTINKGDHTDHAKINAEIKKIWELGYFSDVSASIEESGEGRLLVFTVQEKPKITDVV  240
U70214     LLSMPVRTGDTVNDEDISNTIRALFATGNFEDVRVLRD----GDTLLVQVKERPTIASIT   98
           *  :.:..** .:. .*. *:  ::  * *.**   :      *  *:. *.:*:*.*:..

Li_OMP100  VQGSKAVSIDNILAAMSSK--KGSVISDRLLSQDIQK-ITDLYRKEGYYLAEVNYEIKEK  297
U70214     FSGNKSVKDDMLKQNLEASGVRVGESLDRTTIADIEKGLEDFYYSVGKYSASVKAVVTPL  158
           ..*.*:*. * :    :..   . :.    **    **:.*   * :.*  * * *.*:  :.

Li_OMP100  ENTSSATLLLTVNEGKKLYIKDVRIEGLETIKAKTLKKELALTERNFLSWFTGTG--VLR  355
U70214     P-RNRVDLKLVFQEGVSAEIQQINIVGNHAGTTDELISHFQL--RDEVPWWNVVGDRKYQ  215
             .   . * *..:**   *:::.** .  *:..:..  * *  *: .*.*::. .*

Li_OMP100  EEYLERDSIAISAYAMNHGYVDIQVASPEVTFN--EKGIVITFRVKEGKRYKIGKIDFKG  413
U70214     KQKLAGDLETLRSYYLDRGYARFNIDSTQVSLTPDKKGIYVTVNITEGDQYKLSGVEVSG  275
           :: *   *  :: :* :::**.  :::  *..*::   :*** :*...**.:**:.  :...*

Li_OMP100  DLIETNEQLLKVTKIDDHKNYEQYFSLSVMQDDVKALTDFYSDYGYAFAEVDLETTKNEE  473
U70214     NLAGHSAEIEQLTKIEPGE-LYNGTKVTKMEDDIKKLLG---RYGYAYPRVQSMPEINDA  331
           :*    . ::  :*** *:  :   : *:**:* :       ****:..*: *  :

Li_OMP100  DATIDVTFLIDKKQKVFLRRIIVEGNTRTRDNVILRELRLADGDLFNGQHLRRSNECLNR  533
U70214     DKTVKLRVNVDAGNRGYVRKIRFEGNDTSKDAVLRREMRQMEGAWLGSDLVDQGKERLNR  391
           * *:.: . :*  :::::*::*  *** ..:*: *:  **.*  :  :..: *** ***

Li_OMP100  LGYFNQVDTDTLPT-GKDDEVDLLVKVQEARTGAITGGVGYSTHSKFGVSGSISERNLWG  592
U70214     LGFFETVDTDTQRVPGSPDQVDVVYKVKERNTGSFNFGIGYGTESGVSFQAGVQQDNWLG  451
           **:*: ***** .*  *.*.:*::  *: :.: *.**  *:** **.. .*  .......  * *

Li_OMP100  KGYILSIEGFISSKSSSLDLSFTNP--RVYDTDFG---FSNNIYTLRDEWDDFRKKTYGD  647
U70214     TGYAVGINGTKNDYQTYAELSVTNPYFTVDGVSLGGRLFYNDFQADDADLSDYTNKSYGT  511
            ** :.*.*   ..  .  :*.***    *  ***   * :..:*  *  : .*  :*:**

Li_OMP100  TIRLFHPIGEYSSIFVGYRIDQYRLYDI-PSTAPRSYLDYQGKNISSVVSGG------FT  700
U70214     DVTLGFPINEYNSLRAGLGYVHNSLSNMQPQVAMWRYLYSMGEHPSTSDQDNSFKTDDFT  571
            : * . **.**.** :. *      :  * ::  *:..*  . **  *:: *:   ...  **

Li_OMP100  FDSTDSRERPSKGHIAK---LIVEYGGGGLGGNDN-FFKPIAELQGFYSISRSKNHIIHW  756
U70214     FNYGWTYNKLDRGYFPTDGSRVNLTGKVTIPGSDNEYYKVTLDTATYVPIDDDHKWVVLG  631
           *:   :   :: ..::..      :    *    :  :*  : *.** ::*  : .:  ::

Li_OMP100  RTRAGAAYKNSKKPVPVFDRFFIGGIDSIRGYDTEDLAPK-----------DP-------  798
U70214     RTRWGYGDGLGGKEMPFYENFYAGGSSTVRGFQSNTIGPKAVYFPHQASNYDPDYDYECA  691
           ***    *     .  * .:*::.. *:  **  * :.:*::.**          **

Li_OMP100  ---------RFGDEIGGDRMAFLNLEYIWTF-----QPELGLALVPFYDIGFQTDSVQTS  844
U70214     TQDGAKDLCKSDDAVGGNAMAVASLEFITPTPFISDKYANSVRTSFFWDMGTVWDTNWDS  751
                     :.*:: **:.**. .**:*  .      :  :.:  *..  :  *: *:*

Li_OMP100  NPFS---------KLKQSYGLELRWRSPMGDLRFAYGIPLNKNVSGKKTRGRFEFSMGQF  895
U70214     SQYSGYPDYSDPSNIRMSAGIALQWMSPLGPLVFSYAQPFKKYDGDK--AEQFQFNIGKT  809
           . :*         :::  :.* :* **:* * *:*. *:.:..* *   *  : *.:*:*:

Li_OMP100  F   896
U70214     W   810
           :
```

FIG. 5

```
Li_PonA    -MKQVISFDMKKFFLNIVIFCFGIILLSIIGLIGLYFWVSRDLPNITKLNDYRPALVTTV  59
AF087677   MIKKIITTCMG---LNNGLALFGVGLIAIAILV-----TYPKLPSLDSLQHYKPKLPLTI  52
            :*::*:  *    **   :  **: *::*        .**.: .*:.*:*  *  *:

Li_PonA    LARDGTLIGYIYREKRFLIPLSFMSPFLPKAFLAAEDAEFYEHEGVNPLAIIRAFLINLQ  119
AF087677   YSSDGQVIGVYGEQRREFTKIDDFFKILKDAVIAAEDKRFYDHWCVDVWGVARAVIGNVM  112
           : ** :**   .::*  :  :.:::.:**..*.:**** .**:* **: .: **.:  *:

Li_PonA    SGTTRQGGSTITQQVIKRLLLSPERSYERKIKEAILAYRLEKYLSKDEILTIYLNQTFLG  179
AF087677   AGGVQSGASTITQQVAKNFYLSSERSFTRKFNEALLAYKIEQSLSKDKILELYFNQIYLG  172
           :*  ::*.*.******* ::  *:***. **: ** *****::::: ***** :**:***

Li_PonA    AHSYGVEAAARTYFAKHAKDLSLAECALLAGLPQAPSRYNPYKDPEAAKIRQRYALRRLH  239
AF087677   QRAYGFASAAQTYFNKNVNDLTLAEAAMLAGLPKAPSAYNPIVNPERAKLRQAYILNNML  232
            :.**. .:**:*** *..:**:***.*:*****:***.*** :.**:***  *   :

Li_PonA    DVGWITQAEYEEALQEPLYFSSMKEGLGAESSWYMEEVRKQLVSFLSKENISQYGIVLPL  299
AF087677   EEQMITLQQRDQALKEELIYERFVQNIDQSALYVAEMARQEL--F-----------EK    277
           :  ** **  ::**:* *::   ::.:: :: :   *::**  *           .*

Li_PonA    YGEDALYELGFTIQTAMDPQAQLVAYDVLRNGLENFSK---RQGWKGPIEHISSTMIQHY  356
AF087677   YGEDA-YTQGFKVYTTVDTAHQRVATEALRKVLRNFDRGSSYRGAENYIDLSKSDNVEET  336
           *****  * :**.: :..:.*:* * ::**: ****.:   :*. :    * :.  .::

Li_PonA    LENATFTPEKLDGGAWAKAIVSKVSQEGAEVFLSSIYKGFVSVETMGWARKPNPEVRSAY  416
AF087677   VSQYLSTLYTVD--KMIPAVVLEASRKGVQIQLPSGRKVTLNNHALGFA------ARAVN  388
           :.:   *   .:*   *:* :::*: :*.: :**  **:  :.    *:        *::

Li_PonA    CAPIKDARSVLNPGDIIWVSGVGPDSTHRYSSKTLDTSKPIPLALQQLPQIQGALISIEP  476
AF087677   NEKMGDDR--IRRGSVIRVKGSG-D----------------TFTVVQEPLLQGALVSLDA  429
            :   *    :. .*:* * *.* *                 .::: * * :**::*::.

Li_PonA    NTGDVIAMIGGYEFGKSQFNRAVQAMRQPGSAFKPIVYSAALDHDYTSATMVLDAPIVEF  536
AF087677   KTGAVRALVGGYDYHSKTFNRATQAMRQPGSTFKPFIYSAALAKGMTASTMINDAPISLP  489
           :** * *::***::..*:.****.*******:***::*****  . **:**:.****

Li_PonA    ME--SGDIWRPGNYEKNFKGPMLFSNALALSRNLCTVRIAQSIGLPAVIERAKALGFNGN  594
AF087677   GKGANGKAWNPKNSDGRYAGYITLRQALTASKNMVSIRILMSIGIGYAQQYIQRFGFKPS  549
            :  .*. *.*.*   *:* : :: **:*:.* ::.**: *** . :   * *:**:..

Li_PonA    -FPEFFSISLGAVEVTPIRLVNAYTAFANGGNLATPRFILSIKDSNN-TVIYRQEIEQHP  652
AF087677   EIPASLSMALGAGETTPLRIAEGYSVFANGGYKVSAHVIDKIYDSQGRLRAQMQPLVAGE  609
            :*    *: ***.* **:*:.: *:.****: :::: *  * **:  .   : :.

Li_PonA    ----VISPQNAYIMASLLKNVVNIGTARKAKVLERP-LAGKTGTTNGEHDAWFIGFTPYL  707
AF087677   NAPQAIDPRNAYIMYKIMQDVVRVGTARGAATLGRSDIAGKTGTTNDNKDAWFVGFNPNV  669
               .*.*:***** .::: :**.:****.*. * *. :*******:::****:**.*.:

Li_PonA    VTGVYVGNDHPQTLGKDGTGAVAALPIFTEYSKVVLKKYPESDFPVPDGITFASIDTQTG  767
AF087677   VTAVYIGFDKPRSMGRAGYGGTIAVPVWVEYIGFALKGTSVKPMKAPEGVVTNGGEVYMR  729
           **.**:* *.*::: : * *.. *:*::.** .. ** .   .  .**: :   :.

Li_PonA    NRATANS----TNSVVLP----------------FYVGTVPEYFDSKDNEVNTIERGED  806
AF087677   ERMTTSSDLALDNSGIRPRPTQPARRAVPNENRRRAESNTAPAREESDETPVLPSNTGNN  789
           :* *:.*    .**  *                    .*   *:.*      *   *::

Li_PonA    ---LLKQFF  816
AF087677   NRQQLDSLF  798
              *...:*
```

FIG. 6

```
Li_HtrA   MFCKLKVIICITLMFIITVVPTIAESALPNFVPLVKDASKAVVNISTEKKIPR---GRTE   57
U32853    -MHTLKRCMAAMVALLALSLAMTAPAELPDFTPLVEQACFAVVNISTRQKLPDRAMARGQ   59
          : .**   :.  : ::     :.  *.: **:*.***::** ***** .*:*     .* :

Li_HtrA   FPMEMFRGLPPGFERFFEQFEPKGPDSQIHKQR---SLGTGFIISSDGYIVTNNHVIEGA   114
U32853    LSIPDLEGLPPMFRDFLERSIPQVPRNPRGQQREAQSLGSGFIISNDGYILTNNHVVADA   119
          :.:  :.**** *. *:*:  *:  *  .  :**   ***.*****.****.*****: .*

Li_HtrA   DSVRVNLEGTSGKEESLPAEVIGRDEETDLALLKVKSKDSLPYLIFGNSDTMEVGEWVLA   174
U32853    DEILVRLSDRS--E--HKAKLIGADPRSDVAVLKIEAKN-LPTLKLGDSNKLKVGEWVLA   174
          *  . *  *   *     *..** *  .:*:*:**:...*: ** * .*.*.*:*******

Li_HtrA   IGNPFGLGHTVTAGILSAKGRDIHAGPFDNFLQTDASINPGNSGGPLINMSGQVVGINTA   234
U32853    IGSPFGFDHSVTAGIVSAKGRSLPNESYVPFIQTDVAINPGNSGGPLLNLQGEVVGINSQ   234
          **.***:.*:*****:*****.:    .  *:***.************:*:.*:*****.

Li_HtrA   IMAS-G--QGIGFAIPSSMADRIIEQLKTNKKVSTGWIGVTIQDVDTNTAKALGLSQAKG   291
U32853    IFTRSGGFMGLSFAIPIDVALNVADQLKKAGKVSTGWLGVVIQEVNKDLAESFGLDKPSG   294
          *::  *   *:.**** .:*  :::***..:******:**.**:*:. .*:. **.:..*

Li_HtrA   ALVGSVVPGDPADKAGLKVGDIVTQADGKQIDSASSLLKAIATKPPFSVVKLKVWRDGKS   351
U32853    ALVAQLVEDGPAAKGGLQVGDVILSLNGQSINESADLPHLVGNMKPGDKINLDVIRNGQR   354
          ***..:*  ..** *.**:***: . :.*.*:.*:: .  *.  *.*     *.*:.*:

Li_HtrA   KDISITLGER----KTTSSQKQSSPESLPGALGLSVRPLTQEESKSFDVKLGIGLLVVSV   407
U32853    KSLSMAVGSLPDDDEEIASMGAPGAERSSNRLGVTVADLTAEQRKSLDIQG--GVVIKEV   402
          *.:*:::*.      : :*   ...*  **..*.:.** *::**:*:::    *::..:*

Li_HtrA   EPNKPASEAGIREQDIILSANLKPLQSADDLANIICGDAKKKGVIMLQLQRNGQTFFKTL   467
U32853    Q-DGPAAVIGLRPGDVITHLDNKAVTSTKVFADVAKALPKNR-SVSMRVLRQGRASFITF   470
          : : **: *:*  *:*   .. *.::*:.. :*:   . *:: : :::**:*::* *:*

Li_HtrA   SLTEDSN   474
U32853    KLAE---   474
          .*:*
```

FIG. 7

```
Li_HypC    MCHAIPVKVIELLDNDIIRATVGDSTTILTVSGMLLPEPVTVGDYIIVHAGFAIHKLEAT  60
AJ223629   MCLAIPAR-IETIENGVATCRVGASDTFVKASLLLEGQAGPGDYLVVHAGFALRKMDVK   59
           ** ****.: ** ::.:  .  ** *:::.. :**  .    ********::.: :

Li_HypC    EAEESLRLFRELSIAV-GDTPNF    82
AJ223629   EAEESLQVMRDMAAVMNGGDVRF    82
           ******: :*:::::  * . *
```

FIG. 8

```
Li_ORF1    ------------------------------------------------------------
U67555     MNVFDKYAEEYDKWFDENEIIYKSEIEALKRHIPKGRGLEIGVGTGRFAKPFNIKIGVDI   60

Li_ORF1    ----------EFQLGALDDLPFEDESFNYASLVTILEYVEDPKKILAEAFRVASDG-     46
U67555     SKEMAKIAEKRGIKVIIAKGEDLPFKDEEFFLINTVLEFAENPKKMIEEAKRVLKRGG  120
                     .: :**:..** *** :: ** :: * **..* ***:: ** **  *

Li_ORF1    -IIVGFTNKWSINHIINSTLQLLHKKPKKDSQWVSPWQLIRITKQLYPECRIYCRSTLLG   105
U67555     KIIGIIDRDSFLGKMYEEKKQKSK-FYKDANFLSAKEVIENLKELG------FKN      169
           :**.:: **  :  *:::::.::. **::::.: ::**.  :*:*.*      . :

Li_ORF1    PKRTWDVTSSWSKLNRIILSFPIG--TYVGMRIEKRPKPTLTPLLLKAKEQAVNVYNALS   153
U67555     IKATQTIFKEIDKVDKVEVKEGYGEGGFVAISAEKI------------------------  205
            *   .:  .   *::: :.: *    :*: ..**:

Li_ORF1    PEATSTIQHNRTNK    177
U67555     --------------
```

FIG. 9

```
Li_LysS       LIQKKKSHPPIKLATKSPHVSYFKPLLESLAEKNELNEVIKNCVVKSCELLDSGIPLYPD  60
AB012100_LysS ------------------------MSHEELNDQLRVRREKLKKIEELGVDPFGK       30
                                      ::.:***::   ::    : ::  *:   ::   .

Li_LysS       EFVKEHYAGMLRAEYEAYSASELESLDEIFACAGRIISLPSFGKVIFFHIMDRSGF QCY 120
AB012100_LysS RFERTHKAEELFELYGDLSKEELEEQQIEVAVAGRIMTKFGMGKAGFAHIQDVTGQ QIY  90
              .*.:**  ::  *.*    . ..* :* .*:*****::.  *  *:* :*::: ** **

Li_LysS       ASRENMGEEAFSTFKKFDIGDIVGVNGKLFRTKMGELTLNCSTITLLAKSFRSLPEKHNG 180
AB012100_LysS VRQDDVGEQQYELFKISDLGDIVGVRGTMFKTKVGELSIFVSSYEFLTKALRPLPEKYHG 150
               ::::.** :: .** :*:*******.*.:* **:***::. : :: *:: * ****::*

Li_LysS       LTNIELRYRQRYIDLIVNPKTRDIFRKRSKIIHEIRAFLIENGFIEVETPILQPIPGGAM 240
AB012100_LysS LKDIEQRYRQRYLDLIMNPESKKTFITRSLIIQSMRRYLISHGYLEVETPMMHAVAGGAA 210
              *.:**:****** *** **::: :*  ** **.  *:**  .*:*****::: :.***

Li_LysS       ARPFTTHNNAMDMTLYMRIAPELYLKRLLVGGFEKLFELNRSFRNEGISIQHNPEFTMCE 300
AB012100_LysS ARPFITHHNALDMTLYMRIAIELHLKRLIVGGLEKVYEICRVFRNEGISTRHNPEFTMLE 270
              ****:**:**:********* **:****:***:**::*: *.******* :******:*

Li_LysS       FYWAYATYLDLMELTEEMFAYLTKKICGTMTISYQGNTIIFTPGTWQKYTFHESLEKIGG 360
AB012100_LysS LYEAYADFRDIMKLTENLIAHIATEVLGTTKIQYGEHLVF LTP-EWRRLHMVDAIKEYVG 329
               *.**  : *:*:***::: ::.:::.**   ** *: ::  *   :: : :: **  *

Li_LysS       HSPEFYNNFEKVSEYIKEHGEKVLTTDKIGKLQAKLFDLIVENKLIQPTFIYHYPTDISP 420
AB012100_LysS VDFWRQMSDEEARELAKEHGVEVAPHMTFGHIVNEFFEQKVEDKLIQPTFIYGHPVFISP 389
                . : :.. :..     ****:.* .  . :: .*   :::********* :*..***

Li_LysS       LSKKNKDNPEVTDRFELFIAGKEIANAFSELNDPIDQRLFFEEQVLEKARGDEEACFMDE 480
AB012100_LysS LAKKNPDDPRFTDRFELFIVGREHANAFTELNDPIDQRQFEEQLKEREQGNDEAHFMDE  449
              *:***.*:*.:********.*:* ****:********* *  *: :::* ::** ****

Li_LysS       DYLRALEYGMPPAAGEGIGIDRLVMLLTDSPSIREVILFELLRTER 526
AB012100_LysS DFLEALEYGMPPTGGLGIGVDRLVMLLTNSPSIRDVLLFQMRHK-  494
              *:*.********:.* ***:*******:*****:*::*::  :   ::
```

LAWSONIA INTRACELLULARIS PROTEINS, AND RELATED METHODS AND MATERIALS

This application claims priority under 35 U.S.C. §119(e) of U.S. application Ser. Nos. 60/160,922, filed Oct. 22, 1999 and 60/163,868, filed Nov. 5, 1999, which applications are hereby incorporated by reference.

FIELD OF THE INVENTION

The present invention relates to proteins derived from *Lawsonia intracellularis* and encompasses related proteins, nucleic acids, and immunogenic compositions. The immunogenic compositions are particularly useful in prevention of *L. intracellularis* infections in susceptible animals, such as pigs. The proteins, fragments, and nucleic acids can also be employed as diagnostic agents.

BACKGROUND OF THE INVENTION

Commercially raised pigs are sensitive to a wide spectrum of intestinal diseases or syndromes that are collectively referred to as porcine proliferative enteropathy (PPE). These diseases include intestinal adenomatosis complex (Barker I. K. et al., 1985, In "Pathology of Domestic Animals," 3$^{rd}$ Edition, Vol. 2 p. 1–237, eds. K, V. F. Jubb et al. (Academic Press Orlando)), porcine intestinal adenomatosis (PIA), necrotic enteritis (Rowland A. C. et al., 1976, *Veterinary Record* 97:-178–180), proliferative haemorrhagic enteropathy (Love, R. J. et al., 1977, *Veterinary Record* 100: 473), regional ileitis (Jonsson, L. et al., 1976, Acta *Veterinaria Scandinavica* 17: 223–232), haemorrhagic bowel syndrome (O'Neil, I. P. A., 1970, *Veterinary Record* 87:742–747), porcine proliferative enteritis and Campylobacter spp-induced enteritis (Straw, B. E., 1990, *Journal of American Veterinary Medical Association* 197: 355–357).

One major type of PPE is non-haemorrhagic and is manifested by porcine intestinal adenomatosis (PIA). This form of PPE frequently causes growth retardation and mild diarrhea. Another important type of PPE is haemorrhagic. It is often fatal, and is manifested by proliferative haemorrhagic enteropathy (PHE) wherein the distal small intestine lumen becomes engorged with blood.

While PPE in pigs is commercially most important, PPE is also a problem in the raising of hamsters (Stills, H. F., 1991, *Infection and Immunology* 59: 3227–3236), ferrets (Fox et al. 1989, *Veterinary Pathology* 26: 515–517), guinea pigs (Elwell et al., 1981, *Veterinary Pathology* 18: 136–139), rabbits (Schodel et al., 1990, *Veterinary Pathology* 27: 73–80) and certain birds (Mason et al, 1998).

The organism that causes PPE is the Campylobacter-like bacterium "*L. intracellularis*" (McOrist S et al, 1995, *International Journal Of Systematic Bacteriology* 45: 820–825). This organism is also known as lleal symbiont intracellularis (Stills, 1991, supra). PPE-like diseases in pigs may also be caused by other species of Campylobacter (Gebhart et al., 1983, *American Journal of Veterinary Research* 44: 361–367).

*L. intracellularis* is located in the cytoplasm of villi and intestinal crypt cells of infected animals, where it causes structural irregularities and enterocyte proliferation. Abscesses form as the villi and intestinal crypts become branched and fill with inflammatory cells.

Current control of PPE relies on the use of antibacterial compounds. There is, however, a need for alternative means of controlling *L. intracellularis* infection.

International Patent Application No. PCT/AU96/00767 describes *L. intracellularis* polypeptides and immunogenic compositions that are useful as vaccines. There is, however, a need for additional compositions that confer resistance to *L. intracellularis* infection.

SUMMARY OF THE INVENTION

The present invention relates to an isolated polynucleotide molecule comprising a nucleotide sequence that is selected from the group consisting of:

a) a nucleotide sequence encoding *L. intracellularis* HtrA, PonA, HypC, LysS, YcfW, ABC1, or Omp100 protein;

b) a nucleotide sequence that is a substantial part of the nucleotide sequence encoding the *L. intracellularis* HtrA, PonA, HypC, LysS, YcfW, ABC1, or Omp100 protein; and c) a nucleotide sequence that is homologous to the nucleotide sequence of a) or b).

In another aspect, the invention relates to a recombinant vector comprising these polynucleotide molecules, including those encoding a carrier or fusion partner such that expression of the recombinant vector results in a fusion protein comprising the carrier or fusion partner fused to a protein or polypeptide encoded by the nucleotide sequences described above. The invention also encompasses transformed host cells comprising these recombinant vectors and polypeptides produced by such transformed host cells.

In another aspect, the present invention relates to an isolated polypeptide that is selected from the group consisting of:

(a) *L. intracellularis* HtrA, PonA, HypC, LysS, YcfW, ABC1, or Omp100 protein;

(b) a polypeptide having an amino acid sequence that is homologous to that of the *L. intracellularis* HtrA, PonA, HypC, LysS, YcfW, ABC1, or Omp100 protein;

(c) a polypeptide consisting of a substantial portion of the *L. intracellularis* HtrA, PonA, HypC, LysS, YcfW, ABC1, or Omp100 protein or of the polypeptide having an amino acid sequence that is homologous to that of the *L. intracellularis* HtrA, PonA, HypC, LysS, YcfW, ABC1, or Omp100 protein;

(d) a fusion protein comprising the protein or polypeptide of (a), (b) or (c) fused to another protein or polypeptide; and (e) an analog or derivative of the protein or polypeptide of (a), (b), (c) or (d).

The present invention further provides a polynucleotide molecule comprising a nucleotide sequence of greater than 20 nucleotides having promoter activity and found within SEQ ID NO: 2 from about nt 2691 to about nt 2890.

The present invention further relates to a method of preparing any of these polypeptides, comprising culturing host cells transformed with a recombinant expression vector and recovering the expressed polypeptide from the cell culture. The vector comprises a polynucleotide molecule comprising a nucleotide sequence encoding any of the polypeptides, the nucleotide sequence being in operative association with one or more regulatory elements. Culturing is conducted under conditions conducive to expression of the polypeptide.

In yet another aspect, the invention relates to an isolated antibody that specifically reacts with any of the *L. intracellularis* HtrA, PonA, HypC, LysS, YcfW, ABC1, or Omp100 proteins or polypeptides described above.

The invention also relates to an immunizing composition that comprises an immunologically effective amount of a protein, polypeptide, antibody, or polynucleotide of the invention in combination with a pharmaceutically acceptable carrier. The present invention encompasses a method of immunizing a PPE susceptible animal against *L. intracellularis* infection that comprises administering to the animal the immunizing composition.

The invention also relates to a kit for immunizing a PPE susceptible animal against a disease condition caused or exacerbated by *L. intracellularis* that comprises a container having therein an immunologically effective amount of one of the proteins, polypeptides, antibodies, or polynucleotides described above. The invention also relates to a kit for detecting the presence of *L. intracellularis*, an *L. intracellularis* specific amino acid or nucleotide sequence, or an anti- *L. intracellularis* antibody, comprising a container that has therein a protein, polypeptide, polynucleotide, or antibody of the invention.

BRIEF DESCRIPTION OF DRAWINGS

FIG. 2 shows an alignment of the YcfW amino acid sequence with the most similar sequence found in a search of the GenBank database.

FIG. 3 shows an alignment of the ABC1 amino acid sequence with the most similar sequence found in a search of the GenBank database.

FIG. 4 shows an alignment of the Omp100 amino acid sequence with the most similar sequence found in a search of the GenBank database.

FIG. 5 shows an alignment of the PonA amino acid sequence with the most similar sequence found in a search of the GenBank database.

FIG. 6 shows an alignment of the HtrA amino acid sequence with the most similar sequence found in a search of the GenBank database.

FIG. 7 shows an alignment of the HypC amino acid sequence with the most similar sequence found in a search of the GenBank database.

FIG. 8 shows an alignment of the Orf1 amino acid sequence with the most similar sequence found in a search of the GenBank database.

FIG. 9 shows an alignment of the LysS amino acid sequence with the most similar sequence found in a search of the GenBank database.

DETAILED DESCRIPTION OF THE INVENTION

Figure 1:
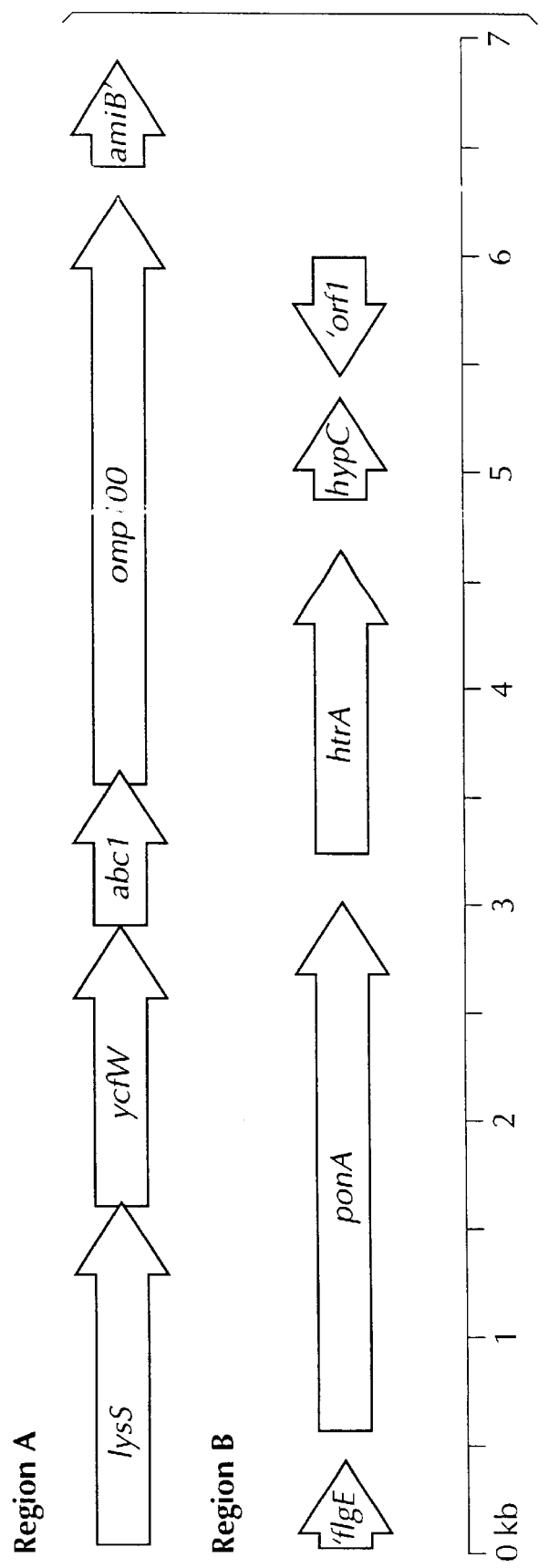
FIG. 1 shows the arrangement of gene cluster A, containing the genes encoding the LysS, YcfW, ABC1 and Omp100 proteins, and the arrangement of gene cluster B, encoding the PonA, HtrA, and HypC proteins.

All patents, patent applications, and publications cited herein are hereby incorporated by reference in their entireties.

Polynucleotide Molecules

An isolated polynucleotide molecule of the present invention can have a nucleotide sequence derived from any species or strain of Lawsonia, but is preferably from the species intracellularis. Pathogenic strains or species of Lawsonia for use in practicing the present invention can be isolated from organs, tissues or body fluids of infected animals using isolation techniques as described below.

As used herein, the terms "polynucleotide molecule," "polynucleotide sequence," "coding sequence," "open- reading frame (ORF)," and the like, are intended to refer to both DNA and RNA molecules, which can either be single-stranded or double-stranded, and that can include one or more prokaryotic sequences, cDNA sequences, genomic DNA sequences including exons and introns, and chemically synthesized DNA and RNA sequences, and both sense and corresponding anti-sense strands. As used herein, the term "ORF" refers to the minimal nucleotide sequence required to encode a Lawsonia HtrA, PonA, HypC, LysS, YcfW, ABC1, or Omp100 protein, without any intervening termination codons.

Production and manipulation of the polynucleotide molecules and oligonucleotide molecules disclosed herein are within the skill in the art and can be carried out according to recombinant techniques described, among other places, in Maniatis et al., 1989, *Molecular Cloning, A Laboratory Manual*, Cold Spring Harbor Laboratory Press, Cold Spring Harbor, N.Y.; Ausubel et al., 1989, *Current Protocols In Molecular Biology*, Greene Publishing Associates & Wiley Interscience, NY; Sambrook et at, 1989, *Molecular Cloning: A Laboratory Manual*, 2d ed., Cold Spring Harbor Laboratory Press, Cold Spring Harbor, N.Y.; Innis et al. (eds), 1995, *PCR Strategies*, Academic Press, Inc., San Diego; and Erlich (ed), 1992, *PCR Technology*, Oxford University Press, New York and all revisions of these references.

References herein to the nucleotide sequences shown in SEQ ID NOS: 1 AND 2, and to substantial portions thereof, are intended to also refer to the corresponding nucleotide sequences and substantial portions thereof, respectively, as present in the following plasmids contained in *E. coli* Top 10 cells deposited by Pfizer Inc. at Central Research, Eastern Point Road, Groton, Conn., 06340 with the American Type Culture Collection, P.O. Box 1549, Manassas, Va. 20108:

pER132 containing the ponA gene and accorded ATCC accession number PTA-635, deposited on Sep. 9, 1999;

pER434 containing the htrA gene and accorded ATCC accession number PTA-636, deposited on Sep. 9, 1999;

pER436 containing the hypC gene and accorded ATCC accession number PTA-637, deposited on Sep. 9, 1999;

pER438 containing the ycfW and abc1 genes and accorded ATCC accession number PTA-638, deposited on Sep. 9, 1999;

pER440 containing the omp100 gene and accorded ATCC accession number PTA-639, deposited on Sep. 9, 1999; and pT068 containing the lysS and ycfW genes and accorded ATCC accession number PTA-2232, deposited on Jul. 14, 2000.

In adition, references herein to the amino acid sequences show in SEQ ID NO: 3–9, and SEQ ID NO: 102, and to substantial portion and peptide fragments thereof, are intended to also refer to the corresponding amino acid sequences, and substantion portions and peptide fragments thereof, respectively, encoded by the corresponding portion encoding nucleotide sequences present in the plasmids listed above, unless otherwise indicated.

HtrA-Related Polynucleotide Molecules

The present invention provides an isolated polynucleotide molecule comprising a nucleotide sequence encoding the HtrA protein from *L. intracellularis*. In a preferred embodiment, the HtrA protein has the amino acid sequence of SEQ ID NO: 7. In a further preferred embodiment, the isolated HtrA-encoding polynucleotide molecule of the present invention comprises a nucleotide sequence selected from the group consisting of the nucleotide sequence of SEQ ID NO: 2 from about nt 2891 to about nt 4315, which is the nucleotide sequence of the open reading frame (ORF) of the htrA gene, and the nucleotide sequence of the HtrA-encoding ORF of plasmid pER434 (ATCC accession number PTA-636).

The present invention further provides an isolated polynucleotide molecule having a nucleotide sequence that is homologous to the nucleotide sequence of a HtrA-encoding polynucleotide molecule of the present invention. The term "homologous" when used to refer to a HtrA-related polynucleotide molecule means a polynucleotide molecule having a nucleotide sequence: (a) that encodes the same protein as one of the aforementioned HtrA-encoding polynucleotide molecules of the present invention, but that includes one or more silent changes to the nucleotide sequence according to the degeneracy of the genetic code; or (b) that hybridizes to the complement of a polynucleotide molecule having a nucleotide sequence that encodes the amino acid sequence of the *L. intracellularis* HtrA protein under at least moderately stringent conditions, i.e., hybridization to filter-bound DNA in 0.5 M $NaHPO_4$, 7% sodium dodecyl sulfate (SDS), 1 mM EDTA at 65° C., and washing in 0.2×SSC/0.1% SDS at 42° C. (see Ausubel et al. (eds.), 1989, *Current Protocols in Molecular Biology*, Vol. 1, Green Publishing Associates, Inc., and John Wiley & Sons, Inc., New York, at p. 2.10.3), and that is useful in practicing the present invention. In a preferred embodiment, the homologous polynucleotide molecule hybridizes to the complement of a polynucleotide molecule having a nucleotide sequence that encodes the amino acid sequence of the *L. intracellularis* HtrA protein under highly stringent conditions, i.e., hybridization to filter-bound DNA in 0.5 M $NaHPO_4$, 7% SDS, 1 mM EDTA at 65° C., and washing in 0.1×SSC/0.1% SDS at 68° C. (Ausubel et al., 1989, above), and is useful in practicing the present invention. In a more preferred embodiment, the homologous polynucleotide molecule hybridizes under highly stringent conditions to the complement of a polynucleotide molecule consisting of a nucleotide sequence selected from the group consisting of the HtrA encoding ORF of SEQ ID NO: 2, which is from about nt 2891 to about nt 4315. As noted above, reference to homologous polynucleotide molecules herein is also intended to refer to the complements of such molecules.

As used herein, a polynucleotide molecule is "useful in practicing the present invention" where the polynucleotide molecule can be used to amplify a Lawsonia-specific polynucleotide molecule using a standard amplification technique, such as the polymerase chain reaction, or as a diagnostic reagent to detect the presence of a Lawsonia-specific polynucleotide in a fluid or tissue sample from a Lawsonia-infected animal, or where the polynucleotide molecule encodes a polypeptide that is useful in practicing the invention, as described below.

Polynucleotide molecules of the present invention having nucleotide sequences that are homologous to the nucleotide sequence of a HtrA-encoding polynucleotide molecule of the present invention do not include polynucleotide molecules that have been described from bacteria such as *E. coli*, *S. typhimunum*, *C. jejuni*, *H. influenzae*, *B. melitensis*, *B. abortus*, *C. trachomatis*, *Y. enterocolitia*, *Rickettsia*, *B. burgdorferi*, and *B. subtilis*. The *L. intracellularis* HtrA protein encoded by SEQ ID NO: 2 has 39.6% identity of amino acid sequence with the *B. abortus* HtrA protein. The *L. intracellularis* protein is 474 residues in length and the *B. abortus* protein is 513 residues in length. The *L. intracellularis* protein is 35.4% identical to that of *H. influenzae*.

The homologous nucleotide sequence of the molecule of the invention preferably comprises a sequence that has more than 50%, more preferably more than about 90%, even more preferably more than about 95%, and most preferably more than about 99% sequence identity to the molecule of SEQ ID NO: 2, which is from about nt 2891 to about nt 4315, wherein sequence identity is determined by use of the BLASTN algorithm (GenBank, National Center for Biotechnology Information).

In another embodiment, the polynucleotide has a homologous sequence that is more than about 50% of the length of the nucleotide sequence encoding the *L. intracellularis* HtrA protein. In another embodiment the sequence is more than 70%, in another embodiment the sequence is more than 90%, and in another embodiment more than about 98%, of the length of the nucleotide sequence encoding the *L. intracellularis* protein. In yet another embodiment, the isolated polynucleotide that has a homologous sequence is equal in length to the sequence encoding the *L. intracellularis* HtrA protein.

In yet another embodiment, the nucleotide sequence that is homologous to the *L. intracellularis* HtrA protein encoding sequence has between 1 and 50, more preferably between 1 and 25, and most preferably between 1 and 5 nucleotides inserted, deleted, or substituted with respect to the sequence of SEQ ID NO: 2 which is from about nt 2891 to about nt 4315.

The present invention further provides an isolated polynucleotide molecule comprising a nucleotide sequence that encodes a polypeptide that is homologous to the *L. intracellularis* HtrA protein. As used herein to refer to polypeptides that are homologous to the *L. intracellularis* HtrA protein, the term "homologous" refers to a polypeptide otherwise having the amino acid sequence of the *L. intracellularis* HtrA protein, but in which one or more amino acid residues has been substituted with a different amino acid residue, where the resulting polypeptide is useful in practicing the present invention. Conservative amino acid substitutions are well-known in the art. Rules for making such substitutions include those described by Dayhof, M. D., 1978, Nat. Biomed. Res. Found., Washington, D.C., Vol. 5, Sup. 3, among others. More specifically, conservative amino acid substitutions are those that generally take place within a family of amino acids that are related in acidity, polarity, or bulkiness of their side chains. Genetically encoded amino acids are generally divided into four groups: (1) acidic=aspartate, glutamate; (2) basic lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, and tyrosine. Phenylalanine, tryptophan and tyrosine are also jointly classified as aromatic amino acids. One or more replacements within any particular group, e.g., of a leucine with an isoleucine or valine, or of an aspartate with a glutamate, or of a threonine with a serine, or of any other amino acid residue with a structurally related amino acid residue, e.g., an amino acid residue with similar acidity, polarity, bulkiness of side chain, or with similarity in some combination thereof, will generally have an insignificant effect on the function or immunogenicity of the polypeptide. In a preferred embodiment, the homologous polypeptide has at least about 50%, more preferably at least about 70%, and even more preferably at least about 90% sequence identity, and most preferably at least 95% sequence identity to SEQ ID NO: 7.

In another embodiment, the polynucleotide encodes an isolated polypeptide consisting of the *L. intracellularis* HtrA protein having between 1 and 10, and more preferably between 1 and 5, amino acids inserted, deleted, or substituted, including combinations thereof. In a more particular example of this embodiment, the polynucleotide encodes an isolated polypeptide having between 1 and 5 amino acids conservatively substituted for the HtrA sequence of SEQ ID NO: 7.

As used herein, a polypeptide is "useful in practicing the present invention" where the polypeptide can be used as a diagnostic reagent to detect the presence of Lawsonia-specific antibodies in a blood, serum, or other biological fluid sample from an animal that has developed an immune response to Lawsonia. The polypeptide is also useful if it can be used to induce an immune response in an animal against Lawsonia.

The present invention further provides a polynucleotide molecule consisting of a substantial portion of any of the aforementioned Lawsonia HtrA-related polynucleotide molecules of the present invention. As used herein, a "substantial portion" of a HtrA-related polynucleotide molecule means a polynucleotide molecule consisting of less than the complete nucleotide sequence of the HtrA-related polynucleotide molecule, but comprising at least about 5%, more preferably at least about 10%, and even more preferably at least about 20%, and most preferably at least about 50% of the nucleotide sequence of the HtrA-related polynucleotide molecule; and that is useful in practicing the present invention. Such polynucleotide molecules include, for example polynucleotide molecules encoding peptide fragments of the HtrA protein.

In addition to the nucleotide sequences of any of the aforementioned HtrA-related polynucleotide molecules, polynucleotide molecules of the present invention can further comprise, or alternatively may consist of, nucleotide sequences selected from those that naturally flank thee HtrA ORF or gene in situ in *L. intracellularis*, and include the nucleotide sequences shown in SEQ ID NO: 2 from about nt 2691 to about nt 2890 and from about nt 4316 to about nt 4580, or substantial portions thereof.

PonA-Related Polynucleotide Molecules

The present invention provides an isolated polynucleotide molecule comprising a nucleotide sequence encoding the PonA protein from *L. intracellularis*. In a preferred, embodiment, the PonA protein has the amino acid sequence of SEQ ID NO: 6. In a further preferred embodiment, the isolated PonA-encoding polynucleotide molecule of the present invention comprises a nucleotide sequence selected from the group consisting of the nucleotide sequence of SEQ ID NO: 2 from about nt 252 to about nt 2690 (the nucleotide sequence of the open reading frame (ORF) of the PonA gene) and the nucleotide sequence of the PonA-encoding ORF of plasmid pER432 (ATCC accession number PTA-635).

The present invention further provides an isolated polynucleotide molecule having a nucleotide sequence that is "homologous" to the nucleotide sequence of a PonA-encoding polynucleotide molecule of the present invention, as that term is correspondingly defined above with respect to HtrA related polynucleotide molecules. In a preferred embodiment, the homologous polynucleotide molecule hybridizes to the complement of a polynucleotide molecule having a nucleotide sequence that encodes the amino acid sequence of the *L. intracellularis* PonA protein under highly stringent conditions. In a more preferred embodiment, the homologous polynucleotide molecule hybridizes under highly stringent conditions to the complement of a polynucleotide molecule consisting of a nucleotide sequence of SEQ ID NO: 2 from about nt 252 to about nt 2690.

Polynucleotide molecules of the present invention having nucleotide sequences that are homologous to the nucleotide sequence of a PonA-encoding polynucleotide molecule of the present invention do not include known polynucleotide molecules encoding PonA proteins of *Neisseria flavescens, N. gonorrhoeae*, and *N. meningitidis*.

The homologous nucleotide sequence of the molecule of the invention preferably comprises a sequence that has more than 50%, more preferably more than about 90%, even more preferably more than about 95%, and most preferably more than about 99% sequence identity to the molecule of SEQ ID NO: 2, which is from about nt 252 to about nt 2690, wherein sequence identity is determined by use of the BLASTN algorithm (GenBank, National Center for Biotechnology Information).

In another embodiment, the polynucleotide has a homologous sequence that is more than about 50% of the length of the nucleotide sequence encoding the *L. intracellularis* PonA protein. In another embodiment, the sequence is more than 90%, and in another embodiment more than about 98%, of the length of the nucleotide sequence encoding the *L. intracellularis* protein. In yet another embodiment, the isolated polynucleotide that has a homologous sequence is equal in length to the sequence encoding the *L. intracellularis* PonA protein.

In yet another embodiment, the nucleotide sequence that is homologous to the *L. intracellularis* PonA protein encoding sequence has between 1 and 50, more preferably between 1 and 25, and most preferably between 1 and 5 nucleotides inserted, deleted, or substituted with respect to the sequence of SEQ ID NO: 2.

The present invention further provides an isolated polynucleotide molecule comprising a nucleotide sequence that encodes a polypeptide that is "homologous" to the L. intracellularisPonA protein, as that term is correspondingly described with respect to the HtrA protein above. In a preferred embodiment, the homologous polypeptide has at least about 50%, more preferably at least about 70%, and even more preferably at least about 90% sequence identity, and most preferably at least 95% sequence identity to SEQ ID NO: 6.

In another embodiment, the polynucleotide encodes an isolated polypeptide consisting of the *L. intracellularis* PonA protein having between 1 and 10, and more preferably between 1 and 5, amino acids inserted, deleted, or substituted, including combinations thereof. In a more particular example of this embodiment, the polynucleotide encodes an isolated polypeptide having between 1 and 5 amino acids conservatively substituted for the PonA sequence of SEQ ID NO: 6.

The present invention further provides a polynucleotide molecule consisting of a "substantial portion" of any of the aforementioned Lawsonia PonA-related polynucleotide molecules of the present invention, as that term is correspondingly described above with respect to the HtrA protein.

In addition to the nucleotide sequences of any of the aforementioned PonA-related polynucleotide molecules, polynucleotide molecules of the present invention can further comprise, or alternatively may consist of, nucleotide sequences selected from those that naturally flank the ponA ORF or gene in situ in *L. intracellularis*, and include the nucleotide sequences shown in SEQ ID NO: 2 from about nt 126 to about nt 251 and from about nt 2691 to about nt 2890, or substantial portions thereof.

HypC-Related Polynucleotide Molecules

The present invention provides an isolated polynucleotide molecule comprising a nucleotide sequence encoding the HypC protein from *L. intracellularis*. In a preferred embodiment, the HypC protein has the amino acid sequence of SEQ ID NO: 8. In a further preferred embodiment, the isolated HypC-encoding polynucleotide molecule of the present invention comprises a nucleotide sequence selected from the group consisting of the nucleotide sequence of SEQ ID NO: 2 from about nt 4581 to about nt 4829, and the nucleotide sequence of the HypC-encoding ORF of plasmid pER436 (ATCC accession number PTA-637).

The present invention further provides an isolated polynucleotide molecule having a nucleotide sequence that is "homologous" to the nucleotide sequence of a HypC-encoding polynucleotide molecule of the present invention, as that term is correspondingly defined above with respect to HtrA related polynucleotide molecules. In a preferred embodiment, the homologous polynucleotide molecule hybridizes to the complement of a polynucleotide molecule having a nucleotide sequence that encodes the amino acid sequence of the *L. intracellularis* HypC protein under highly stringent conditions. In a more preferred embodiment, the homologous polynucleotide molecule hybridizes under highly stringent conditions to the complement of a polynucleotide molecule consisting of a nucleotide sequence selected from the group consisting of the ORF of SEQ ID NO: 2 from about nt 4581 to about nt 4829

Polynucleotide molecules of the present invention having nucleotide sequences that are homologous to the nucleotide sequence of a HypC-encoding polynucleotide molecule of the present invention do not include polynucleotide molecules encoding HypC or HypD proteins of *Desulfovibrio gigas* and *Rizobium leguminosarum*.

The homologous nucleotide sequence of the molecule of the invention preferably comprises a sequence that has more than 50%, more preferably more than about 90%, even more preferably more than about 95%, and most preferably more than about 99% sequence identity to the molecule of SEQ ID NO: 2, which is from about nt 4581 to about nt 4829, wherein sequence identity is determined by use of the BLASTN algorithm (GenBank, National Center for Biotechnology Information).

In another embodiment, the polynucleotide has a homologous sequence that is more than about 50% of the length of the nucleotide sequence encoding the *L. intracellularis* HypC protein. In another embodiment, the sequence is more than 90%, and in another embodiment more than about 98%, of the length of the nucleotide sequence encoding the *L. intracellularis* HypC protein. In yet another embodiment, the isolated polynucleotide that has a homologous sequence is equal in length to the sequence encoding the *L. intracellularis* HypC protein.

In yet another embodiment, the nucleotide sequence that is homologous to the *L. intracellularis* HypC protein encoding sequence has between 1 and 50, more preferably between 1 and 25, and most preferably between 1 and 5 nucleotides inserted, deleted, or substituted with respect to the sequence of SEQ ID NO: 2.

The present invention further provides an isolated polynucleotide molecule comprising a nucleotide sequence that encodes a polypeptide that is "homologous" to the *L. intracellularis* HypC protein, as that term is correspondingly described with respect to the HtrA protein above. In a preferred embodiment, the homologous polypeptide has at least about 50%, more preferably at least about 70%, and even more preferably at least about 90% sequence identity, and most preferably at least 95% sequence identity to SEQ ID NO: 8.

In another embodiment, the polynucleotide encodes an isolated polypeptide consisting of the *L. intracellularis* HypC protein having between 1 and 10, and more preferably between 1 and 5, amino acids inserted, deleted, or substituted, including combinations thereof. In a more particular example of this embodiment, the polynucleotide encodes an isolated polypeptide having between 1 and 5 amino acids conservatively substituted for the HypC sequence of SEQ ID NO: 8.

The present invention further provides a polynucleotide molecule consisting of a "substantial portion" of any of the aforementioned Lawsonia HypC-related polynucleotide molecules of the present invention, as that term is correspondingly described above with respect to the HtrA protein.

In addition to the nucleotide sequences of any of the aforementioned HypC-related polynucleotide molecules, polynucleotide molecules of the present invention can further comprise, or alternatively may consist of, nucleotide sequences selected from those that naturally flank the hypC ORF or gene in situ in *L. intracellularis*, and include the nucleotide sequences shown in SEQ ID NO: 2 from about nt 4316 to about nt 4580 and from about nt 4830 to about nt 4911, or substantial portions thereof.

LysS-Related Polynucleotide Molecules

The present invention provides an isolated polynucleotide molecule comprising a nucleotide sequence encoding a LysS protein from *L. intracellularis*. In a preferred embodiment, the LysS protein has the amino acid sequence of SEQ ID NO: 102. In a further preferred embodiment, the isolated LysS-encoding polynucleotide molecule of the present invention comprises a nucleotide sequence selected from the group consisting of the nucleotide sequence of SEQ ID NO: 1 from about nt 165 to about nt 1745 of the nucleotide sequence of the lysS gene, and the nucleotide sequence of the LysS-encoding ORF of plasmid pT068 (ATCC accession number PTA-2232).

The present invention further provides an isolated polynucleotide molecule having a nucleotide sequence that is "homologous" to the nucleotide sequence of a LysS-encoding polynucleotide molecule of the present invention, as that term is correspondingly defined above with respect to HtrA related polynucleotide molecules. In a preferred embodiment, the homologous polynucleotide molecule hybridizes to the complement of a polynucleotide molecule having a nucleotide sequence that encodes the amino acid sequence of the *L. intracellularis* LysS protein under highly stringent conditions. In a more preferred embodiment, the homologous polynucleotide molecule hybridizes under highly stringent conditions to the complement of a polynucleotide molecule consisting of a nucleotide sequence of SEQ ID NO. 1 from about nt 165 to about nt 1745.

The homologous nucleotide sequence of the molecule of the invention preferably comprises a sequence that has more than 50%, more preferably more than about 90%, even more preferably more than about 95%, and most preferably more than about 99% sequence identity to the molecule of SEQ ID NO: 1 from about nt 165 to about nt 1745, wherein sequence identity is determined by use of the BLASTN algorithm (GenBank, National Center for Biotechnology Information).

In another embodiment, the polynucleotide has a homologous sequence that is more than about 50% of the length of the nucleotide sequence encoding the *L. intracellularis* LysS protein. In another embodiment, the sequence is more than 90%, and in another embodiment more than about 98%, of the length of the nucleotide sequence encoding the *L. intracellularis* LysS protein. In yet another embodiment, the isolated polynucleotide that has a homologous sequence is equal in length to the sequence encoding the *L. intracellularis* LysS protein.

In yet another embodiment, the nucleotide sequence that is homologous to the *L. intracellularis* LysS protein encoding sequence has between 1 and 50, more preferably between 1 and 25, and most preferably between 1 and 5 nucleotides inserted, deleted, or substituted with respect to the sequence of SEQ ID NO: 1.

The present invention further provides an isolated polynucleotide molecule comprising a nucleotide sequence that encodes a polypeptide that is "homologous" to the *L. intracellularis* LysS protein, as that term is correspondingly described with respect to the HtrA protein above. In a preferred embodiment, the homologous polypeptide has at least about 50%, more preferably at least about 70%, and even more preferably at least about 90% sequence identity, and most preferably at least 95% sequence identity to SEQ ID NO: 102.

In another embodiment, the polynucleotide encodes an isolated polypeptide consisting of the *L. intracellularis* LysS protein having between 1 and 10, and more preferably between 1 and 5, amino acids inserted, deleted, or substituted, including combinations thereof. In a more particular example of this embodiment, the polynucleotide encodes an isolated polypeptide having between 1 and 5 amino acids conservatively substituted for the LysS sequence of SEQ ID NO: 102.

The present invention further provides a polynucleotide molecule consisting of a "substantial portion" of any of the aforementioned Lawsonia lysS-related polynucleotide molecules of the present invention, as that term is correspondingly described above with respect to the HtrA protein.

In addition to the nucleotide sequences of any of the aforementioned lysS-related polynucleotide molecules, polynucleotide molecules of the present invention can further comprise, or alternatively may consist of, nucleotide sequences selected from those that naturally flank the lysS ORF or gene in situ in *L. intracellularis*.

YcfW-Related Polynucleotide Molecules

The present invention provides an isolated polynucleotide molecule comprising a nucleotide sequence encoding the YcfW protein from *L. intracellularis*. In a preferred embodiment, the YcfW protein has the amino acid sequence of SEQ ID NO: 3. In a further preferred embodiment, the isolated YcfW-encoding polynucleotide molecule of the present invention comprises a nucleotide sequence selected from the group consisting of the nucleotide sequence of SEQ ID NO: 1 from about nt 1745 to about nt 3028 of the nucleotide sequence of the YcfW gene, and the nucleotide sequence of the YcfW-encoding ORF of plasmids pER438 (ATCC accession number PTA-638) and pT068 (ATCC accession number PTA-2232). The present invention further provides an isolated polynucleotide molecule having a nucleotide sequence that is "homologous" to the nucleotide sequence of a YcfW-encoding polynucleotide molecule of the present invention, as that term is correspondingly defined above with respect to HtrA related polynucleotide molecules. In a preferred embodiment, the homologous polynucleotide molecule hybridizes to the complement of a polynucleotide molecule having a nucleotide sequence that encodes the amino acid sequence of the *L. intracellularis* YcfW protein under highly stringent conditions. In a more preferred embodiment, the homologous polynucleotide molecule hybridizes under highly stringent conditions to the complement of a polynucleotide molecule consisting of a nucleotide sequence of SEQ ID NO: 1 from about nt 1745 to about nt 3028.

The homologous nucleotide sequence of the molecule of the invention preferably comprises a sequence that has more than 50%, more preferably more than about 90%, even more preferably more than about 95%, and most preferably more than about 99% sequence identity to the molecule of SEQ ID NO: 1 from about nt 1745 to about nt 3028, wherein sequence identity is determined by use of the BLASTN algorithm (GenBank, National Center for Biotechnology Information).

In another embodiment, the polynucleotide has a homologous sequence that is more than about 50% of the length of the nucleotide sequence encoding the *L. intracellularis* YcfW protein. In another embodiment, the sequence is more than 90%, and in another embodiment more than about 98%, of the length of the nucleotide sequence encoding the *L. intracellularis* YcfW protein. In yet another embodiment, the isolated polynucleotide that has a homologous sequence is equal in length to the sequence encoding the *L. intracellularis* YcfW protein.

In yet another embodiment, the nucleotide sequence that is homologous to the *L. intracellularis* YcfW protein encoding sequence has between 1 and 50, more preferably between 1 and 25, and most preferably between 1 and 5 nucleotides inserted, deleted, or substituted with respect to the sequence of SEQ ID NO: 1.

The present invention further provides an isolated polynucleotide molecule comprising a nucleotide sequence that encodes a polypeptide that is "homologous" to the *L. intracellularis* YcfW protein, as that term is correspondingly described with respect to the HtrA protein above. In a preferred embodiment, the homologous polypeptide has at least about 50%, more preferably at least about 70%, and even more preferably at least about 90% sequence identity, and most preferably at least 95% sequence identity to SEQ ID NO: 3.

In another embodiment, the polynucleotide encodes an isolated polypeptide consisting of the *L. intracellularis* YcfW protein having between 1 and 10, and more preferably between 1 and 5, amino acids inserted, deleted, or substituted, including combinations thereof. In a more particular example of this embodiment, the polynucleotide encodes an isolated polypeptide having between 1 and 5 amino acids conservatively substituted for the YcfW sequence of SEQ ID NO: 3.

The present invention further provides a polynucleotide molecule consisting of a "substantial portion" of any of the aforementioned Lawsonia YcfW-related polynucleotide molecules of the present invention, as that term is correspondingly described above with respect to the HtrA protein.

In addition to the nucleotide sequences of any of the aforementioned YcfW-related polynucleotide molecules, polynucleotide molecules of the present invention can further comprise, or alternatively may consist of, nucleotide sequences selected from those that naturally flank the ycfW ORF or gene in situ in *L. intracellularis*.

ABC1-Related Polynucleotide Molecules

The present invention provides an isolated polynucleotide molecule comprising a nucleotide sequence encoding the ABC1 protein from *L. intracellularis*. In a preferred embodiment, the ABC1 protein has the amino acid sequence of SEQ ID NO: 4. In a further preferred embodiment, the isolated ABC1-encoding polynucleotide molecule of the present invention comprises a nucleotide sequence selected from the group consisting of the nucleotide sequence of SEQ ID NO: 1 from about nt 3031 to about nt 3738 (the nucleotide sequence of the open reading frame (ORF) of the ABC1 gene) and the nucleotide sequence of the ABC1-encoding ORF of plasmid pER438 (ATCC accession number PTA-638).

The present invention further provides an isolated polynucleotide molecule having a nucleotide sequence that is "homologous" to the nucleotide sequence of an ABC1-encoding polynucleotide molecule of the present invention, as that term is correspondingly defined above with respect to HtrA related polynucleotide molecules. In a preferred embodiment, the homologous polynucleotide molecule hybridizes to the complement of a polynucleotide molecule having a nucleotide sequence that encodes the amino acid sequence of the *L. intracellularis* ABC1 protein under highly stringent conditions. In a more preferred embodiment, the homologous polynucleotide molecule hybridizes under highly stringent conditions to the complement of a polynucleotide molecule consisting of a nucleotide sequence selected from the group consisting of the ORF of SEQ ID NO: 1, which is from about nt 3031 to about nt 3738.

Polynudeotide molecules of the present invention having nucleotide sequences that are homologous to the nucleotide sequence of a ABC1-encoding polynucleotide molecule of the present invention do not include polynucleotide molecules encoding ABC1 proteins of *Neisseria flavescens, N. gonorrhoeae*, and *N. meningitudis*.

The nucleotide sequence of the molecule of the invention preferably comprises a sequence that has more than 50%, more preferably more than about 90%, even more preferably more than about 95%, and most preferably more than about 99% sequence identity to the molecule of SEQ ID NO: 1 from about nt 3031 to about nt 3738, wherein sequence identity is determined by use of the BLASTN algorithm (GenBank, National Center for Biotechnology Information).

In another embodiment, the polynucleotide has a homologous sequence that is more than about 50% of the length of the nucleotide sequence encoding the *L. intracellularis* ABC1 protein. In another embodiment, the sequence is more than 90%, and in another embodiment more than about 98%, of the length of the nucleotide sequence encoding the *L. intracellularis* ABC1 protein. In yet another embodiment, the isolated polynucleotide that has a homologous sequence is equal in length to the sequence encoding the *L. intracellularis* ABC1 protein.

In yet another embodiment, the nucleotide sequence that is homologous to the *L. intracellularis* ABC1 protein encoding sequence has between 1 and 50, more preferably between 1 and 25, and most preferably between 1 and 5 nucleotides inserted, deleted, or substituted with respect to the sequence of SEQ ID NO: 1.

The present invention further provides an isolated polynucleotide molecule comprising a nucleotide sequence that encodes a polypeptide that is "homologous" to the *L. intracellularis* ABC1 protein, as that term is correspondingly described with respect to the HtrA protein above. In a preferred embodiment, the homologous polypeptide has at least about 50%, more preferably at least about 70%, and even more preferably at least about 90% sequence identity, and most preferably at least 95% sequence identity to SEQ ID NO: 1.

In another embodiment, the polynucleotide encodes an isolated polypeptide consisting of the *L. intracellularis* ABC1 protein having between 1 and 10, and more preferably between 1 and 5, amino acids inserted, deleted, or substituted, including combinations thereof. In a more particular example of this embodiment, the polynucleotide encodes an isolated polypeptide having between 1 and 5 amino acids conservatively substituted for the ABC1 sequence of SEQ ID NO: 4.

The present invention further provides a polynucleotide molecule consisting of a "substantial portion" of any of the aforementioned Lawsonia ABC1-related polynucleotide molecules of the present invention, as that term is correspondingly described above with respect to the HtrA protein.

In addition to the nucleotide sequences of any of the aforementioned ABC1-related polynucleotide molecules, polynucleotide molecules of the present invention can further comprise, or alternatively may consist of, nucleotide sequences selected from those that naturally flank the abc1 ORF or gene in situ in *L. intracellularis*, and include the flanking nucleotide sequences shown in SEQ ID NO: 1.

Omp100-Related Polynucleotide Molecules

The present invention provides an isolated polynucleotide molecule comprising a nucleotide sequence encoding the Omp100 protein from *L. intracellularis*. In a preferred embodiment, the Omp100 protein has the amino acid sequence of SEQ ID NO: 5. In a further preferred embodiment, the isolated Omp100-encoding polynucleotide molecule of the present invention comprises a nucleotide sequence selected from the group consisting of the nucleotide sequence of SEQ ID NO: 1 from about nt 3695 to about nt 6385 (the nucleotide sequence of the open reading frame (ORF) of the Omp100 gene), and the nucleotide sequence of the Omp100-encoding ORF of plasmid pER440 (ATCC accession number PTA-639).

The present invention further provides an isolated polynucleotide molecule having a nucleotide sequence that is "homologous" to the nucleotide sequence of a Omp100-encoding polynucleotide molecule of the present invention, as that term is correspondingly defined above with respect to HtrA related polynucleotide molecules. In a preferred embodiment, the homologous polynucleotide molecule hybridizes to the complement of a polynucleotide molecule having a nucleotide sequence that encodes the amino acid sequence of the *L. intracellularis* Omp100 protein under highly stringent conditions. In a more preferred embodiment, the homologous polynucleotide molecule hybridizes under highly stringent conditions to the complement of a polynucleotide molecule consisting of a nucleotide sequence selected from the group consisting of the ORF of SEQ ID NO: 1, which is from about nt 3695 to about nt 6385.

Polynucleotide molecules of the present invention having nucleotide sequences that are homologous to the nucleotide sequence of a Omp100-encoding polynucleotide molecule of the present invention do not include polynucleotide molecules encoding any of the following proteins listed in the GenBank database: YaeT (Accn. U70214 or AE000127) of *E. coli*; Oma90 (Accn. AF120927) of *Shigella flexneri*, Omp85 (Accn. AF021245) of *Neisseria meningitidis*, D15 (Accn. U60834) of *Haemophilus influenzae* (D15), and Oma87 (Accn. U60439) of *Pasteurella multocida*.

The nucleotide sequence of the molecule of the invention preferably comprises a homologous sequence that has more than 50%, more preferably more than about 90%, even more preferably more than about 95%, and most preferably more than about 99% sequence identity to the molecule of SEQ ID NO: 1 from about nt 3695 to about nt 6385, wherein sequence identity is determined by use of the BLASTN algorithm (GenBank, National Center for Biotechnology Information).

In another embodiment, the polynucleotide has a homologous sequence that is more than about 50% of the length of the nucleotide sequence encoding the L. intracellularis Omp100 protein. In another embodiment, the sequence is more than 90%, and in another embodiment more than about 98%, of the length of the nucleotide sequence encoding the L. intracellularis Omp100 protein. In yet another embodiment, the isolated polynucleotide that has a homologous sequence is equal in length to the sequence encoding the L. intracellularis Omp100 protein.

In yet another embodiment, the nucleotide sequence that is homologous to the L. intracellularis Omp100 protein encoding sequence has between 1 and 50, more preferably between 1 and 25, and most preferably between 1 and 5 nucleotides inserted, deleted, or substituted with respect to the sequence of SEQ ID NO: 5.

The present invention further provides an isolated polynucleotide molecule comprising a nucleotide sequence that encodes a polypeptide that is "homologous" to the L. intracellularis Omp100 protein, as that term is correspondingly described with respect to the HtrA protein above. In a preferred embodiment, the homologous polypeptide has at least about 50%, more preferably at least about 70%, and even more preferably at least about 90% sequence identity, and most preferably at least 95% sequence identity to SEQ ID NO: 5.

In another embodiment, the polynucleotide encodes an isolated polypeptide consisting of the L. intracellularis Omp100 protein having between 1 and 10, and more preferably between 1 and 5, amino acids inserted, deleted, or substituted, including combinations thereof. In a more particular example of this embodiment, the polynucleotide encodes an isolated polypeptide having between 1 and 5 amino acids conservatively substituted for the Omp100 sequence of SEQ ID NO: 5.

The present invention further provides a polynucleotide molecule consisting of a "substantial portion" of any of the aforementioned Lawsonia Omp100-related polynucleotide molecules of the present invention, as that term is correspondingly described above with respect to the HtrA protein.

In addition to the nucleotide sequences of any of the aforementioned Omp100-related polynucleotide molecules, polynucleotide molecules of the present invention can further comprise, or alternatively may consist of, nucleotide sequences selected from those that naturally flank the omp100 ORF or gene in situ in L. intracellularis, and include the nucleotide sequences shown in SEQ ID NO: 1.

Promoter Sequences

The present invention also relates to a polynucleotide molecule comprising a nucleotide sequence greater than 20 nucleotides having promoter activity and found within SEQ ID NO: 2 from about nt 2691 to about nt 2890, or its complement. As further discussed below in the Examples, it has been determined that this region of the Lawsonia sequence contains a temperature responsive promoter for the htrA gene. In a preferred embodiment, the polynucleotide comprises the sequence of about nt 2797 to nt 2829.

The present invention also relates to oligonucleotides having promoter activity that hybridize under moderately stringent, and more preferably under highly stringent conditions, to the complement of the nucleotide sequence greater than 20 nucleotides having promoter activity and found within SEQ ID NO: 2 from about nt 2691 to about nt 2890. Preferably the oligonucleotide having promoter activity hybridizes under moderately stringent or highly stringent conditions to the complement of the polynucleotide comprising the sequence from about nt 2797 to nt 2829. In another embodiment, the invention encompasses an oligonucleotide having promoter activity having between 1 and 25, and most preferably between 1 and 5 nucleotides inserted, deleted, or substituted with respect to the sequence of SEQ ID NO: 2 which is from about nt 2691 to about nt 2890.

The functional sequences having promoter activity of the present invention are useful for a variety of purposes including for controlling the recombinant expression of any of the genes of the present invention, or of other genes or coding sequences, in host cells of L. intracellularis or in host cells of any other species of Lawsonia, or in any other appropriate host cell. Such other genes or coding sequences can either be native or heterologous to the recombinant host cell. The promoter sequence can be fused to the particular gene or coding sequence using standard recombinant techniques as known in the art so that the promoter sequence is in operative association therewith, as "operative association" is defined below. By using the promoter, recombinant expression systems can, for example, be constructed and used to screen for compounds and transcriptional factors that can modulate the expression of the genes of Lawsonia or other bacteria. In addition, such promoter constructs can be used to express heterologous polypeptides in Lawsonia, E. coli, or other appropriate host cells.

Oligonucleotide Molecules

The present invention further provides oligonucleotide molecules that hybridize to any one of the aforementioned polynucleotide molecules of the present invention, or that hybridize to a polynucleotide molecule having a nucleotide sequence that is the complement of any one of the aforementioned polynucleotide molecules of the present invention. Such oligonucleotide molecules are preferably at least about 10 nucleotides in length, and more preferably from about 15 to about 30 nucleotides in length, and hybridize to one or more of the aforementioned polynucleotide molecules under highly stringent conditions, i.e., washing in 6×SSC/0.5% sodium pyrophosphate at about 37° C. for ~14-base oligos, at about 48° C. for ~17-base oligos, at about 55° C. for ~20-base oligos, and at about 60° C. for ~23-base oligos. Other hybridization conditions for longer oligonucleotide molecules of the present invention can be determined by the skilled artisan using standard techniques. In a preferred embodiment, an oligonucleotide molecule of the present invention is complementary to a portion of at least one of the aforementioned polynucleotide molecules of the present invention.

The oligonucleotide molecules of the present invention are useful for a variety of purposes, including as primers in amplification of a Lawsonia-specific polynucleotide molecule for use, e.g., in differential disease diagnosis, or to act as antisense molecules useful in gene regulation. Suitably designed primers can also be used to detect the presence of Lawsonia-specific polynucleotide molecules in a sample of animal tissue or fluid, including brain tissue, lung tissue, intestinal tissue, placental tissue, blood, cerebrospinal fluid, feces, mucous, urine, amniotic fluid, etc. The oligonucleotide molecule specifically reacts with the Lawsonia organism; this is generally accomplished by employing a sequence of sufficient length. The production of a specific amplification product can support a diagnosis of Lawsonia infection, while lack of an amplified product can point to a lack of infection. Methods for conducting amplifications, such as the polymerase chain reaction (PCR), are described, among other places, in Innis et al. (eds), 1995, above, and Erlich (ed), 1992, above. Other amplification techniques known in the art, e.g., the ligase chain reaction, can alternatively be used. The sequences of the polynucleotide molecules disclosed herein can also be used to design primers for use in isolating homologous genes from other species or strains of Lawsonia or other bacterial cells.

Specific though non-limiting embodiments of oligonucleotide molecules useful in practicing the present invention include oligonucleotide molecules selected from the group consisting of SEQ ID NOS: 10–101 and the complements thereof.

Recombinant Expression Systems Cloning and Expression Vectors

The present invention further encompasses methods and compositions for cloning and expressing any of the polynucleotide molecules of the present invention, including cloning vectors, expression vectors, transformed host cells comprising any of said vectors, and novel strains or cell lines derived therefrom. In a preferred embodiment, the present invention provides a recombinant vector comprising a polynucleotide molecule having a nucleotide sequence encoding the HtrA, PonA, HypC, LysS, YcfW, ABC1, or Omp100 protein of L. intracellularis. In specific embodiments, the present invention provides plasmid pER432 containing the ponA gene (ATCC accession number PTA-635), plasmid pER434 containing the htrA gene. (ATCC accession number PTA-636), plasmid pER436 containing the hypC gene (ATCC accession number PTA-637), plasmid pT068 containing the lysS and ycfW genes (ATCC accession number PTA-2232), plasmid pER438 containing the ycfW and abc1 genes (ATCC accession number PTA-638), and plasmid pER440 containing the Omp100 gene (ATCC accession number PTA-639). The invention also encompasses recombinant vectors and transformed cells employed to obtain polypeptides of the invention.

Recombinant vectors of the present invention, particularly expression vectors, are preferably constructed so that the coding sequence for the polynucleotide molecule of the invention is in operative association with one or more regulatory elements necessary for transcription and translation of the coding sequence to produce a polypeptide. As used herein, the term "regulatory element" includes but is not limited to nucleotide sequences that encode inducible and non-inducible promoters, enhancers, operators, ribosome-binding sites, and other elements known in the art that serve to drive and/or regulate expression of polynucleotide coding sequences. Also, as used herein, the coding sequence is in "operative association" with one or more regulatory elements where the regulatory elements effectively regulate and allow for the transcription of the coding sequence or the translation of its mRNA, or both.

Methods are well-known in the art for constructing recombinant vectors containing particular coding sequences in operative association with appropriate regulatory elements, and these can be used to practice the present invention. These methods include in vitro recombinant techniques, synthetic techniques, and in vivo genetic recombination. See, e.g., the techniques described in Maniatis et al., 1989, above; Ausubel et al., 1989, above; Sambrook et al., 1989, above; Innis et al., 1995, above; and Erlich, 1992, above.

A variety of expression vectors are known in the art which can be utilized to express the HtrA, PonA, HypC, LysS, YcfW, ABC1, or Omp100 coding sequences of the present invention, including recombinant bacteriophage DNA, plasmid DNA, and cosmid DNA expression vectors containing the particular coding sequences. Typical prokaryotic expression vector plasmids that can be engineered to contain a polynucleotide molecule of the present invention include pUC8, pUC9, pBR322 and pBR329 (Biorad Laboratories, Richmond, Calif.), pPL and pKK223 (Pharmacia, Piscataway, N.J.), pQE50 (Qiagen, Chatsworth, Calif.), and pGEM-T EASY (Promega, Madison, Wis.), among many others. Typical eukaryotic expression vectors that can be engineered to contain a polynucleotide molecule of the present invention include an ecdysone-inducible mammalian expression system (Invitrogen, Carlsbad, Calif.), cytomegalovirus promoter-enhancer-based systems (Promega, Madison, Wis.; Stratagene, La Jolla, Calif.; Invitrogen), and baculovirus-based expression systems (Promega), among others.

The regulatory elements of these and other vectors can vary in their strength and specificities. Depending on the host/vector system utilized, any of a number of suitable transcription and translation elements can be used. For instance, when cloning in mammalian cell systems, promoters isolated from the genome of mammalian cells, e.g., mouse metallothionein promoter, or from viruses that grow in these cells, e.g., vaccinia virus 7.5K promoter or Moloney murine sarcoma virus long terminal repeat, can be used. Promoters obtained by recombinant DNA or synthetic techniques can also be used to provide for transcription of the inserted sequence. In addition, expression from certain promoters can be elevated in the presence of particular inducers, e.g., zinc and cadmium ions for metallothionein promoters. Non-limiting examples of transcriptional regulatory regions or promoters include for bacteria, the β-gal promoter, the T7 promoter, the TAC promoter, λ left and right promoters, trp and lac promoters, trp-lac fusion promoters, etc.; for yeast, glycolytic enzyme promoters, such as ADH-I and -II promoters, GPK promoter, PGI promoter, TRP promoter, etc.; and for mammalian cells, SV40 early and late promoters, adenovirus major late promoters, among others. The present invention further provides a polynucleotide molecule comprising the nucleotide sequence of the promoter of the htrA gene of L. intracellularis, which can be used to express any of the coding sequences of the present invention in Lawsonia, E. coli, or other suitable hosts.

Specific initiation signals are also required for sufficient translation of inserted coding sequences. These signals typically include an ATG initiation codon and adjacent sequences. In cases where the polynucleotide molecule of the present invention including its own initiation codon and adjacent sequences are inserted into the appropriate expression vector, no additional translation control signals may be needed. However, in cases where only a portion of a coding sequence is inserted, exogenous translational control signals, including the ATG initiation codon, may be required. These exogenous translational control signals and initiation codons can be obtained from a variety of sources, both natural and synthetic. Furthermore, the initiation codon must be in phase with the reading frame of the coding regions to ensure in-frame translation of the entire insert.

Expression vectors can also be constructed that will express a fusion protein comprising a protein or polypeptide of the present invention. Such fusion proteins can be used, e.g., to raise antisera against a Lawsonia protein, to study the biochemical properties of the Lawsonia protein, to engineer a Lawsonia protein exhibiting different immunological or functional properties, or to aid in the identification or purification, or to improve the stability, of a recombinantly-expressed Lawsonia protein. Possible fusion protein expression vectors include but are not limited to vectors incorporating sequences that encode β-galactosidase and trpE fusions, maltose-binding protein fusions (pMal series; New England Biolabs), glutathione-S-transferase fusions (pGEX series; Pharmacia), polyhistidine fusions (pET series; Novagen Inc., Madison, Wis.), and thioredoxin fusions (pTrxFus; Invitrogen, Carlsbad, Calif.). Methods are well-known in the art for constructing expression vectors encoding these and other fusion proteins.

The fusion protein can be useful to aid in purification of the expressed protein. In non-limiting embodiments, e.g., a HtrA, PonA, HypC, LysS, YcfW, ABC1, or Omp100-maltose-binding fusion protein can be purified using amylose resin; a HtrA, PonA, HypC, LysS, YcfW, ABC1, or Omp100-glutathione-S-transferase fusion protein can be purified using glutathione-agarose beads; and a HtrA, PonA, HypC, LysS, YcfW, ABC1, or Omp100-polyhistidine fusion protein can be purified using divalent nickel resin. Alternatively, antibodies against a carrier protein or peptide can be used for affinity chromatography purification of the fusion protein. For example, a nucleotide sequence coding for the target epitope of a monoclonal antibody can be engineered into the expression vector in operative association with the regulatory elements and situated so that the expressed epitope is fused to a Lawsonia protein of the present invention. In a non-limiting embodiment, a nucleotide sequence coding for the FLAG™ epitope tag (International Biotechnologies Inc.), which is a hydrophilic marker peptide, can be inserted by standard techniques into the expression vector at a point corresponding to the amino or carboxyl terminus of the HtrA, PonA, HypC, LysS, YcfW, ABC1, or Omp100 protein. The expressed HtrA, PonA, HypC, LysS, YcfW, ABC1, or Omp100 protein-FLAG™ epitope fusion product can then be detected and affinity-purified using commercially available anti-FLAG™ antibodies.

The expression vector can also be engineered to contain polylinker sequences that encode specific protease cleavage sites so that the expressed Lawsonia protein can be released from the carrier region or fusion partner by treatment with a specific protease. For example, the fusion protein vector can include a nucleotide sequence encoding a thrombin or factor Xa cleavage site, among others.

A signal sequence upstream from and in the same reading frame with the Lawsonia coding sequence can be engineered into the expression vector by known methods to direct the trafficking and secretion of the expressed protein. Non-limiting examples of signal sequences include those from α-factor, immunoglobulins, outer membrane proteins, penicillinase, and T-cell receptors, among others.

To aid in the selection of host cells transformed or transfected with a recombinant vector of the present invention, the vector can be engineered to further comprise a coding sequence for a reporter gene product or other selectable marker. Such a coding sequence is preferably in operative association with the regulatory elements, as described above. Reporter genes that are useful in practicing the invention are well-known in the art and include those encoding chloramphenicol acetyltransferase (CAT), green fluorescent protein, firefly luciferase, and, human growth hormone, among others. Nucleotide sequences encoding selectable markers are well-known in the art, and include those that encode gene products conferring resistance to antibiotics or anti-metabolites, or that supply an auxotrophic requirement. Examples of such sequences include those that encode thymidine kinase activity, or resistance to methotrexate, ampicillin, kanamycin, chloramphenicol, zeocin, pyrimethamine, aminoglycosides, or hygromycin, among others.

Transformation of Host Cells

The present invention further provides transformed host cells comprising a polynucleotide molecule or recombinant vector of the present invention, and cell lines derived therefrom. Host cells useful in practicing the invention can be eukaryotic or prokaryotic cells. Such transformed host cells include but are not limited to microorganisms, such as bacteria transformed with recombinant bacteriophage DNA, plasmid DNA or cosmid DNA vectors, or yeast transformed with a recombinant vector, or animal cells, such as insect cells infected with a recombinant virus vector, e.g., baculovirus, or mammalian cells infected with a recombinant virus vector, e.g., adenovirus or vaccinia virus, among others. For example, a strain of E. coli can be used, such as, e.g., the DH5α strain available from the ATCC, Rockville, Md., USA (Accession No. 31343), or from GIBCO BRL, Gaithersburg, Md. Eukaryotic host cells include yeast cells, although mammalian cells, e.g., from a mouse, hamster, cow, monkey, or human cell line, among others, can also be utilized effectively. Examples of eukaryotic host cells that can be used to express a recombinant protein of the invention include Chinese hamster ovary (CHO) cells (e.g., ATCC Accession No. CCL-61), NIH Swiss mouse embryo cells NIH/3T3 (e.g., ATCC Accession No. CRL-1658), and Madin-Darby bovine kidney (MDBK) cells (ATCC Accession No. CCL-22). Transfected cells can express the polynucleotide of the invention by chromosomal integration, or episomally.

The recombinant vector of the invention is preferably transformed or transfected into one or more host cells of a substantially homogeneous culture of cells. The vector is generally introduced into host cells in accordance with known techniques, such as, e.g., by protoplast transformation, calcium phosphate precipitation, calcium chloride treatment, microinjection, electroporation, transfection by contact with a recombined virus, liposome-mediated transfection, DEAE-dextran transfection, transduction, conjugation, or microprojectile bombardment, among others. Selection of transformants can be conducted by standard procedures, such as by selecting for cells expressing a selectable marker, e.g., antibiotic resistance, associated with the recombinant expression vector.

Once an expression vector is introduced into the host cell, the integration and maintenance of the polynucleotide molecule of the present invention, either in the host cell genome or episomally, can be confirmed by standard techniques, e.g., by Southern hybridization analysis, restriction enzyme analysis, PCR analysis including reverse transcriptase PCR (rt-PCR), or by immunological assay to detect the expected protein product. Host cells containing and/or expressing a polynucleotide molecule of the present invention can be identified by any of at least four general approaches that are well-known in the art, including: (i) DNA-DNA, DNA-RNA, or RNA-antisense RNA hybridization; (ii) detecting the presence of "marker" gene functions; (iii) assessing the level of transcription as measured by the expression of specific mRNA transcripts in the host cell; or (iv) detecting the presence of mature polypeptide product, e.g., by immunoassay, as known in the art.

Expression and Purification of Recombinant Polypeptides

Once a polynucleotide molecule of the present invention has been stably introduced into an appropriate host cell, the transformed host cell is clonally propagated, and the resulting cells are grown under conditions conducive to the maximum production of the encoded polypeptide. Such conditions typically include growing transformed cells to high density. Where the expression vector comprises an inducible promoter, appropriate induction conditions such as, e.g., temperature shift, exhaustion of nutrients, addition of gratuitous inducers (e.g., analogs of carbohydrates, such as isopropyl-β-D-thiogalactopyranoside (IPTG)), accumulation of excess metabolic by-products, or the like, are employed as needed to induce expression.

Where the polypeptide is retained inside the host cells, the cells are harvested and lysed, and the product is substantially purified or isolated from the lysate under extraction conditions known in the art to minimize protein degradation such as, e.g., at 4° C., or in the presence of protease inhibitors, or both. Where the polypeptide is secreted from the host cells, the exhausted nutrient medium ban simply be collected and the polypeptide substantially purified or isolated therefrom.

The polypeptide can be substantially purified or isolated from cell lysates or culture medium, as necessary, using standard methods, including but not limited to one or more of the following methods: ammonium sulfate precipitation, size fractionation, ion exchange chromatography, HPLC, density centrifugation, and affinity chromatography. If the polypeptide lacks biological activity, it can be detected as based, e.g., on size, or reactivity with a polypeptide-specific antibody, or by the presence of a fusion tag. For use in practicing the present invention, the polypeptide can be in an unpurified state as secreted into the culture fluid or as present in a cell lysate, but is preferably substantially purified or isolated therefrom. As used herein, a polypeptide is "substantially purified" where the polypeptide constitutes at least about 20 wt % of the protein in a particular preparation. Also, as used herein, a polypeptide is "isolated" where the polypeptide constitutes at least about 80 wt % of the protein in a particular preparation. In another embodiment of the invention, the protein is present in a preparation in at least about a 1000×higher concentration than its natural counterpart is normally found in a preparation of *L. intracellularis* cell lysate.

Polypeptides

Thus, the present invention encompasses a substantially purified or isolated polypeptide encoded by a polynucleotide of the present invention. In a non-limiting embodiment, the polypeptide is a HtrA, PonA, HypC, LysS, YcfW, ABC1, or Omp100 *L. intracellularis* protein. In a preferred embodiment, the *L. intracellularis* HtrA, PonA, HypC, LysS, YcfW, ABC1, and Omp100 proteins have the amino acid sequences of SEQ ID NOS: 3–8 or SEQ ID NO: 102. In another embodiment, the polypeptides are substantially free of other Lawsonia proteins.

The present invention further provides polypeptides that are homologous to any of the aforementioned *L. intracellularis* proteins, as the term "homologous" is defined above for polypeptides. Polypeptides of the present invention that are homologous to the proteins of the invention do not include polypeptides having the amino acid sequences of non-Lawsonia proteins described herein. The polypeptide of the invention, in one embodiment, has more than 70%, preferably more than about 90%, and most preferably more than about 95% amino acid sequence identity to the Lawsonia proteins, wherein sequence identity is determined by use of the BLASTP algorithm (GenBank, NCBI).

In another embodiment, the polypeptide consists of the *L. intracellularis* HtrA, PonA, HypC, LysS, YcfW, ABC1, or Omp100 protein having between 1 and 10, and more preferably between 1 and 5, amino acids inserted, deleted, or substituted, including combinations thereof. In a more particular example of this embodiment, the isolated polypeptide has between 1 and 5 amino acids conservatively substituted in the amino acid sequence of the HtrA, PonA, HypC, LysS, YcfW, ABC1, or Omp100 protein.

The present invention further provides polypeptides consisting of a substantial portion of any one of the aforementioned polypeptides of the present invention. As used herein, a "substantial portion" of a polypeptide of the present invention, or "peptide fragment," means a polypeptide consisting of less than the complete amino acid sequence of the corresponding full-length polypeptide, but comprising at least about 5%, more preferably at least about 20%, even more preferably at least about 50%, and most preferably at least about 95% of the amino acid sequence thereof, and that is useful in practicing the present invention. Particularly preferred are peptide fragments that are immunogenic, i.e., capable of inducing an immune response which results in production of antibodies that react specifically against the corresponding full-length Lawsonia polypeptide.

In another embodiment, the polypeptide of the invention comprises an epitope of HtrA, PonA, HypC, LysS, YcfW, ABC1, or Omp100 protein that is specifically reactive with anti-Lawsonia antibodies. The epitope is preferably more than 8, more preferably more than 12, and most preferably, more than 20 amino acids of the protein sequence.

The present invention further provides fusion proteins comprising any of the polypeptides of the invention fused to a carrier or fusion partner as known in the art.

The present invention further provides a method of preparing any of the polypeptides described above, comprising culturing a host cell transformed with a recombinant expression vector, said recombinant expression vector comprising a polynucleotide molecule comprising a nucleotide sequence encoding the particular polypeptide, which polynucleotide molecule is in operative association with one or more regulatory elements, under conditions conducive to the expression of the polypeptide, and recovering the expressed polypeptide from the cell culture.

Use of Polypeptides

Once a polypeptide of the present invention of sufficient purity has been obtained, it can be characterized by standard methods, including by SDS-PAGE, size exclusion chromatography, amino acid sequence analysis, immunological activity, biological activity, etc. The polypeptide can be further characterized using hydrophilicity analysis (see, e.g., Hopp and Woods, 1981, Proc. Natl. Acad. Sci. USA 78:3824), or analogous software algorithms, to identify hydrophobic and hydrophilic regions. Structural analysis can be carried out to identify regions of the polypeptide that assume specific secondary structures. Biophysical methods such as X-ray crystallography (Engstrom, 1974, Biochem. Exp. Biol. 11: 7–13), computer modeling (Fletterick and Zoller (eds), 1986, in: *Current Communications in Molecular Biology*, Cold Spring Harbor Laboratory, Cold Spring Harbor, N.Y.), and nuclear magnetic resonance (NMR) can be used to map and study potential sites of interaction between the polypeptide and other putative interacting proteins/receptors/molecules. Information obtained from these studies can be used to design deletion mutants and vaccine compositions, and to design or select therapeutic or pharmacologic compounds that can specifically block the biological function of the polypeptide in vivo.

Polypeptides of the present invention are useful for a variety of purposes, including as components of vaccine compositions to protect PPE susceptible animals against PPE; or as diagnostic reagents, e.g., using standard techniques such as ELISA assays, to screen for Lawsonia-specific antibodies in blood or serum samples from animals; or as antigens to raise polyclonal or monoclonal antibodies, as described below, which antibodies are useful as diagnostic reagents, e.g., using standard techniques such as Western blot assays, to screen for Lawsonia-specific proteins in cell, tissue or fluid samples from an animal.

Analogs and Derivatives of Polypeptides

A polypeptide of the present invention can be modified at the protein level to improve or otherwise alter its biological or immunological characteristics. One or more chemical modifications of the polypeptide can be carried out using known techniques to prepare analogs therefrom, including but not limited to any of the following: substitution of one or more L-amino acids of the polypeptide with corresponding D-amino acids, amino acid analogs, or amino acid mimics, so as to produce, e.g., carbazates or tertiary centers; or specific chemical modification, such as, e.g., proteolytic cleavage with trypsin, chymotrypsin, papain or V8 protease, or treatment with $NaBH_4$ or cyanogen bromide, or acetylation, formylation, oxidation or reduction, etc. Alternatively or additionally, polypeptides of the present invention can be modified by genetic recombination techniques.

A polypeptide of the present invention can be derivatized by conjugation thereto of one or more chemical groups, including but not limited to acetyl groups, sulfur bridging groups, glycosyl groups, lipids, and phosphates, and/or by conjugation to a second polypeptide of the present invention, or to another protein, such as, e.g., serum albumin, keyhole limpet hemocyanin, or commercially activated BSA, or to a polyamino acid (e.g., polylysine), or to a polysaccharide, (e.g., sepharose, agarose, or modified or unmodified celluloses), among others. Such conjugation is preferably by covalent linkage at amino acid side chains and/or at the N-terminus or C-terminus of the polypeptide. Methods for carrying out such conjugation reactions are well-known in the field of protein chemistry.

Derivatives useful in practicing the claimed invention also include those in which a water-soluble polymer such as, e.g., polyethylene glycol, is conjugated to a polypeptide of the present invention, or to an analog or derivative thereof, thereby providing additional desirable properties while retaining, at least in part, the immunogenicity of the polypeptide. These additional desirable properties include, e.g., increased solubility in aqueous solutions, increased stability in storage, increased resistance to proteolytic dehydration, and increased in vivo half-life. Water-soluble polymers suitable for conjugation to a polypeptide of the present invention include but are not limited to polyethylene glycol homopolymers, polypropylene glycol homopolymers, copolymers of ethylene glycol with propylene glycol, wherein said homopolymers and copolymers are unsubstituted or substituted at one end with can alkyl group, polyoxyethylated polyols, polyvinyl alcohol, polysaccharides, polyvinyl ethyl ethers, and $\alpha,\beta$-poly[2-hydroxyethyl]-DL-aspartamide. Polyethylene glycol is particularly preferred. Methods for making water-soluble polymer conjugates of polypeptides are known in the art and are described in, among other places, U.S. Pat. No. 3,788,948; U.S. Pat. No. 3,960,830; U.S. Pat. No. 4,002,531; U.S. Pat. No. 4,055,635; U.S. Pat. No. 4,179,337; U.S. Pat. No. 4,261,973; U.S. Pat. No. 4,412,989; U.S. Pat. No. 4,414,147; U.S. Pat. No. 4,415,665; U.S. Pat. No. 4,609,546; U.S. Pat. No. 4,732,863; U.S. Pat. No. 4,745,180; European Patent (EP) 152,847; EP 98,110; and Japanese Patent 5,792,435, which patents are incorporated herein by reference.

Antibodies

The present invention further provides isolated antibodies directed against a polypeptide of the present invention. In a preferred embodiment, antibodies can be raised against a HtrA, PonA, HypC, LysS, YcfW, ABC1, or Omp100 protein from *L. intracellularis* using known methods. Various host animals selected from pigs, cows, horses, rabbits, goats, sheep, or mice, can be immunized with a partially or substantially purified, or isolated, *L. intracellularis* protein, or with a homolog, fusion protein, substantial portion, analog or derivative thereof, as these are described above. An adjuvant, such as described below, can be used to enhance antibody production.

Polyconal antibodies can be obtained and isolated from the serum of an immunized animal and tested for specificity against the antigen using standard techniques. Alternatively, monoclonal antibodies can be prepared and isolated using any technique that provides for the production of antibody molecules by continuous cell lines in culture. These include but are not limited to the hybridoma technique originally described by Kohler and Milstein (Nature, 1975, 256: 495–497); the human B-cell hybridoma technique (Kosbor et al., 1983, Immunology Today 4:72; Cote et al., 1983, Proc. Natl. Acad. Sci. USA 80: 2026–2030); and the EBV-hybridoma technique (Cole et al., 1985, *Monoclonal Antibodies and Cancer Therapy*, Alan R. Liss, Inc., pp. 77–96). Alternatively, techniques described for the production of single chain antibodies (see, e.g., U.S. Pat. No. 4,946,778) can be adapted to produce *L. intracellularis* antigen-specific single chain antibodies. These publications are incorporated herein by reference.

Antibody fragments that contain specific binding sites for a polypeptide of the present invention are also encompassed within the present invention, and can be generated by known techniques. Such fragments include but are not limited to $F(ab')_2$ fragments, which can be generated by pepsin digestion of an intact antibody molecule, and Fab fragments, which can be generated by reducing the disulfide bridges of the $F(ab')_2$ fragments. Alternatively, Fab expression libraries can be constructed (Huse et al., 1989, Science 246: 1275–1281) to allow rapid identification of Fab fragments having the desired specificity to the *L. intracellularis* protein.

Techniques for the production and isolation of monoclonal antibodies and antibody fragments are well-known in the art, and are additionally described, among other places, in Harlow and Lane, 1988, *Antibodies: A Laboratory Manual*, Cold Spring Harbor Laboratory, and in J. W. Goding, 1986, *Monoclonal Antibodies: Principles and Practice*, Academic Press, London, which are incorporated herein by reference.

Targeted Mutation of Lawsonia Genes

Based on the disclosure of the polynucleotide molecules of the present invention, genetic constructs can be prepared for use in disabling or otherwise mutating a Lawsonia htrA, ponA, lysS, ycfW, hypC, abc1, or omp100 gene (which gene is hereinafter referred to as the "Lawsonia gene"). The Lawsonia gene can be mutated using an appropriately designed genetic construct. For example, the Lawsonia gene can be mutated using a genetic construct of the present invention that functions to: (a) delete all or a portion of the coding sequence or regulatory sequence of the Lawsonia gene; or (b) replace all or a portion of the coding sequence or regulatory sequence of the Lawsonia gene with a different nucleotide sequence; or (c) insert into the coding sequence or regulatory sequence of the Lawsonia gene one or more nucleotides, or an oligonucleotide molecule, or polynucleotide molecule, which can comprise a nucleotide sequence from Lawsonia or from a heterologous source; or (d) carry out some combination of (a), (b) and (c). Alternately, constructs can be employed to alter the expression of the Lawsonia gene or the stability of its encoded protein.

Lawsonia cells in which a Lawsonia gene has been mutated are, for example, useful in practicing the present invention where mutating the gene reduces the pathogenicity of the Lawsonia cells carrying the mutated gene compared to cells of the same strain of Lawsonia where the gene has not been so mutated, and where such Lawsonia cells carrying the disabled gene can be used in a vaccine composition, particularly in a modified live vaccine, to induce or contribute to the induction of, a protective response in an animal against PPE. In a preferred embodiment, the mutation serves to partially or completely disable the Lawsonia gene, or partially or completely disable the protein encoded by the Lawsonia gene. In this context, a Lawsonia gene or protein is considered to be partially or completely disabled if either no protein product is made (for example, the gene is deleted), or a protein product is made that can no longer carry out its normal biological function or can no longer be transported to its normal cellular location, or a product is made that carries out its normal biological function but at a significantly reduced rate. Lawsonia cells in which the Lawsonia gene has been mutated are also useful to increase expression of that gene or the stability of its encoded protein. Mutations are particularly useful that result in a detectable decrease in the pathogenicity of cells of a pathogenic strain of Lawsonia. The invention also encompasses cells expressing proteins and polypeptides of the invention where such cells are constitutive mutants.

In a non-limiting embodiment, a genetic construct of the present invention is used to mutate a wild-type Lawsonia gene by replacement of the coding sequence of the wild-type gene, or a promoter or other regulatory region thereof, or a portion thereof, with a different nucleotide sequence such as, e.g., a mutated coding sequence or mutated regulatory region, or portion thereof. Mutated Lawsonia gene sequences for use in such a genetic construct can be produced by any of a variety of known methods, including by use of error-prone PCR, or by cassette mutagenesis. For example, oligonucleotide-directed mutagenesis can be employed to alter the coding sequence or promoter sequence of a wild-type Lawsonia gene in a defined way, e.g., to introduce a frame-shift or a termination codon at a specific point within the sequence. Alternatively or additionally, a mutated nucleotide sequence for use in the genetic construct of the present invention can be prepared by insertion or deletion of the coding sequence or promoter sequence of one or more nucleotides, oligonucleotide molecules or polynucleotide molecules, or by replacement of a portion of the coding sequence or promoter sequence with one or more different nucleotides, oligonucleotide molecules or polynucleotide molecules. Such oligonucleotide molecules or polynucleotide molecules can be obtained from any naturally occurring source or can be synthetic. The inserted or deleted sequence can serve simply to disrupt the reading frame of the Lawsonia gene, or can further encode a heterologous gene product such as a selectable marker.

Alternatively or additionally, random mutagenesis can be used to produce a mutated Lawsonia gene sequence for use in a genetic construct of the present invention. Random mutagenesis can be carried out by any suitable techniques such as, e.g., by exposing cells carrying a Lawsonia gene to ultraviolet radiation or x-rays, or to chemical mutagens such as N-methyl-N'-nitrosoguanidine, ethyl methane sulfonate, nitrous acid or nitrogen mustards, and then selecting for cells carrying a mutation in the particular gene. See, e.g., Ausubel, 1989, above, for a review of mutagenesis techniques.

Mutations to produce modified Lawsonia cells that are useful in practicing the present invention can occur anywhere in the Lawsonia gene, including in the ORF, or in the promoter or other regulatory region, or in any other sequences that naturally comprise the gene or ORF, or that alter expression of the gene or the stability of its encoded protein. Such Lawsonia cells include mutants in which a modified form of the protein normally encoded by the Lawsonia gene is produced, or in which no protein normally encoded by the Lawsonia gene is produced, and can be null, conditional, constitutive, or leaky mutants.

Alternatively, a genetic construct of the present invention can comprise nucleotide sequences that naturally flank the Lawsonia gene or ORF in situ, with only a portion or no nucleotide sequences from the coding region of the gene itself. Such a genetic construct would be useful, e.g., to delete the entire Lawsonia gene or ORF.

In one embodiment, a genetic construct of the present invention comprises a polynucleotide molecule that can be used to disable a Lawsonia gene, comprising: (a) a polynucleotide molecule having a nucleotide sequence that is otherwise the same as a nucleotide sequence encoding a HtrA, PonA, HypC, LysS, YcfW, ABC1, or Omp100 protein from *L. intracellularis*, but which nucleotide sequence further comprises one or more disabling mutations; or (b) a polynucleotide molecule comprising a nucleotide sequence that naturally flanks the ORF of a Lawsonia gene in situ. Once transformed into cells of a strain of Lawsonia, the polynucleotide molecule of the genetic construct is specifically targeted to the particular Lawsonia gene by homologous recombination, and thereby either replaces the gene or portion thereof or inserts into the gene. As a result of this recombination event, the Lawsonia gene otherwise native to that particular strain of Lawsonia is disabled.

In another embodiment, a genetic construct employs a mutation that alters expression, e.g., by constitutively expressing or overexpressing the HtrA, PonA, HypC, LysS, YcfW, ABC1, or Omp100 protein. Such a mutation can be useful, for example, to weaken the host cells. The construct can also employ a mutation that increases stability of the protein to, e.g., attenuate the host cell.

For targeted gene mutation through homologous recombination, the genetic construct is preferably a plasmid, either circular or linearized, comprising a mutated nucleotide sequence as described above. In a non-limiting embodiment, at least about 200 nucleotides of the mutated sequence are used to specifically direct the genetic construct of the present invention to the particular targeted Lawsonia gene for homologous recombination, although shorter lengths of nucleotides can also be effective. In addition, the plasmid preferably comprises an additional nucleotide sequence encoding a reporter gene product or other selectable marker that is constructed so that it will insert into the Lawsonia genome in operative association with the regulatory element sequences of the native Lawsonia gene to be disrupted. Reporter genes that can be used in practicing the invention are well-known in the art and include those encoding CAT, green fluorescent protein, and β-galactosidase, among others. Nucleotide sequences encoding selectable markers are also well-known in the art, and include those that encode gene products conferring resistance to antibiotics or anti-metabolites, or that supply an auxotrophic requirement. Examples of such sequences include those that encode pyrimethamine resistance, or neomycin phosphotransferase (which confers resistance to aminoglycosides), or hygromycin phosphotransferase (which confers resistance to hygromycin).

Methods that can be used for creating the genetic constructs of the present invention are well-known in the art, and include in vitro recombinant techniques, synthetic techniques, and in vivo genetic recombination, as described, among other places, in Maniatis et al., 1989, above; Ausubel et al., 1989, above; Sambrook et al., 1989, above; Innis et al., 1995, above; and Erlich, 1992, above.

Lawsonia cells can be transformed or transfected with a genetic construct of the present invention in accordance with known techniques, such as, e.g., by electroporation. Selection of transformants can be carried out using standard techniques, such as by selecting for cells expressing a selectable marker associated with the construct. Identification of transformants in which a successful recombination event has occurred and the particular target gene has been altered can be carried out by genetic analysis, such as by Southern blot analysis, or by Northern analysis to detect a lack of mRNA transcripts encoding the particular protein, or cells lacking the particular protein, as determined, e.g., by immunological analysis, by the appearance of a novel phenotype, such as reduced pathogenicity, by PCR assay, or by some combination thereof.

In a further non-limiting embodiment, the genetic construct of the present invention can additionally comprise a different gene or coding region from Lawsonia or from a different pathogen that infects the animal, which gene or coding region encodes an antigen useful to induce, or contribute to the induction of, a separate and distinct protective immune response in the animal upon vaccination with the modified live Lawsonia cells of the present invention. This additional gene or coding region can be further engineered to contain a signal sequence that leads to secretion of the encoded antigen from the modified live Lawsonia cell, thereby allowing for the antigen to be displayed to the immune system of the vaccinated animal.

The present invention thus provides modified live Lawsonia cells in which the htrA, ponA, hypC, lysS, ycfW, abc1, or omp100 gene has been mutated. In addition, the present invention provides a method of preparing modified live Lawsonia cells, comprising: (a) transforming cells of Lawsonia with a genetic construct of the invention; (b) selecting transformed cells in which the htrA, ponA, hypC, lysS, ycfW, abc1, or omp100 gene has been mutated by the genetic construct; and (c) selecting from among the cells of step (b) those cells that can be used in a vaccine to protect a PPE susceptible animal against PPE. The invention also encompasses killed cell compositions prepared from such modified Lawsonia cells.

Culturing Lawsonia Bacteria

Lawsonia bacterium for use in the present invention can be cultured and maintained in vitro using methods described e.g. by Joens et al., 1997, Am. J. Vet Res. 58:1125–1131; Lawson et al., 1993, Journal of Clinical Microbiology 31:1136–1142; and McOrist et al., 1995, supra.

Anti-Lawsonia Vaccines

The present invention further provides a vaccine against PPE, comprising an immunologically effective amount of a protein or polypeptide of the present invention, and a pharmaceutically acceptable carrier. In a preferred embodiment, the vaccine comprises a HtrA, PonA, HypC, LysS, YcfW, ABC1, or Omp100 L. intracellularis protein.

The present invention further provides a vaccine against PPE, comprising an immunologically effective amount of one or more polynucleotide molecules of the present invention, and a pharmaceutically acceptable carrier. In a preferred embodiment, the vaccine comprises a polynucleotide molecule having a nucleotide sequence encoding L. intracellularis HtrA, PonA, HypC, LysS, YcfW, ABC1, or Omp100.

The present invention further provides a vaccine against PPE, comprising an immunologically effective amount of modified Lawsonia bacteria of the present invention, and a pharmaceutically acceptable carrier. In one embodiment, the modified Lawsonia cells for use in the vaccine of the present invention are live L. intracellularis bacteria which express a HtrA$^-$, PonA$^-$, HypC$^-$, LysS$^-$, YcfW$^-$, ABC1$^-$, or Omp100$^-$ phenotype. Alternatively, the vaccine of the present invention can comprise any of such modified Lawsonia cells of the present invention that have been inactivated. Inactivation of modified Lawsonia cells can be carried out using any techniques known in the art, including by chemical treatment, such as with binary ethylenimine (BEI), or beta-propiolactone, or formaldehyde, or by freeze-thawing or heat treatment, or by homogenization of cells, or by a combination of these types of techniques. Vaccines prepared from homogenized, modified Lawsonia cells can consist of either the entire unfractionated cell homogenate, or an immunologically effective subfraction thereof.

As used herein, the term "immunologically effective amount" refers to that amount of antigen, e.g., protein, polypeptide, polynucleotide molecule, or modified cells, capable of inducing a protective response against PPE when administered to a member of a PPE susceptible animal species after either a single administration, or after multiple administrations.

The phrase "capable of inducing a protective response" is used broadly herein to include the induction or enhancement of any immune-based response in the animal in response to vaccination, including either an antibody or cell-mediated immune response, or both, that serves to protect the vaccinated animal against PPE. The terms "protective response" and "protect" as used herein to refer not only to the absolute prevention of PPE or absolute prevention of infection by Lawsonia, but also to any detectable reduction in the degree or rate of infection by such a pathogen, or any detectable reduction in the severity of the disease or any symptom or condition resulting from infection by the pathogen, including, e.g., any detectable reduction in the rate of formation, or in the absolute number, of lesions formed in one or more tissues, or the transmission of infection to other animals, in the vaccinated animal as compared to an unvaccinated infected animal of the same species.

In a further preferred embodiment, the vaccine of the present invention is a combination vaccine for protecting a PPE susceptible animal against PPE and, optionally, one or more other diseases or pathological conditions that can afflict the animal, which combination vaccine comprises an immunologically effective amount of a first component comprising a polypeptide, polynucleotide molecule, or modified Lawsonia cells of the present invention; an immunologically effective amount of a second component that is different from the first component, and that is capable of inducing, or contributing to the induction of, a protective response against a disease or pathological condition that can afflict the PPE susceptible animal; and a pharmaceutically acceptable carrier.

The second component of the combination vaccine is selected based on its ability to induce, or contribute to the induction of, a protective response against either PPE or another disease or pathological condition that can afflict members of the relevant species, as known in the art. Any antigenic component that is useful in a vaccine composition in the particular species can be used as the second component of the combination vaccine. Such antigenic components include but are not limited to those that provide protection against pathogens selected from the group consisting of Leptospira spp., Campylobacter spp., *Staphylococcus aureus, Streptococcus agalactiae, Streptococcus suis,* Mycoplasma spp., Klebsiella spp., Salmonella spp., rotavirus, coronavirus, rabies, *Pasteurella hemolytica, Pasteurella multocida,* Clostridia spp., Tetanus toxoid, *E. coli,* Cryptosporidium spp., Eimeria spp., Trichomonas spp:, Serpulina (Brachyspira) hyodysenteriae, *Actinobacillus pleuropneumoniae, Actinobacillus suis, Salmonella cholerasuis, Erysipelothrix rhusiopathiae,* Leptospira sp., *Staphylococcus hyicus, Haemophilus parasuis, Bordetella bronchiseptica, Mycoplasma hyopneumoniae,* porcine reproductive and respiratory syndrome virus, swine influence virus, porcine immunodeficiency virus, transmissible gastroenteritis virus, porcine parvovirus, encephalomyocarditis virus, coronavirus, pseudorabies virus, circovirus and other eukaryotic parasites.

In one embodiment, the combination vaccine of the present invention comprises a combination of two or more components selected from the group consisting of an immunologically effective amount of a protein or polypeptide of the present invention, an immunologically effective amount of a polynucleotide molecule of the present invention, and an immunologically effective amount of modified Lawsonia cells of the present invention.

The vaccines of the present invention can further comprise one or more additional immunomodulatory components including, e.g., an adjuvant or cytokine, as described below.

The present invention further provides a method of preparing a vaccine against PPE, comprising combining an immunologically effective amount of a *L. intracellularis* protein or polypeptide, or polynucleotide molecule, or modified Lawsonia cells, of the present invention, with a pharmaceutically acceptable carrier, in a form suitable for administration to a PPE susceptible animal. In a preferred embodiment, the protein is *L. intracellularis* HtrA, PonA, HypC, LysS, YcfW, ABC1, or Omp100, the polynucleotide molecule preferably comprises a nucleotide sequence encoding *L. intracellularis* HtrA, PonA, HypC, LysS, YcfW, ABC1, or Omp100 protein and the modified Lawsonia bacteria has an HtrA$^-$, PonA$^-$, HypC$^-$, LysS$^-$, YcfW$^-$, ABC1$^-$, or Omp100$^-$ phenotype.

A vaccine comprising modified live Lawsonia cells of the present invention can be prepared using an aliquot of culture fluid containing said Lawsonia cells, either free in the medium or residing in mammalian host cells, or both, and can be administered directly or in concentrated form to the PPE susceptible animal. Alternatively, modified live Lawsonia cells can be combined with a pharmaceutically acceptable carrier, with or without an immunomodulatory agent, selected from those known in the art and appropriate to the chosen route of administration, preferably where at least some degree of viability of the modified live Lawsonia cells in the vaccine composition is maintained.

Vaccine compositions of the present invention can be formulated following accepted convention to include pharmaceutically acceptable carriers, such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Suitable other vaccine vehicles and additives, including those that are particularly useful in formulating modified live vaccines, are known or will be apparent to those skilled in the art,. See, e.g., Remington's *Pharmaceutical Science*, 18th ed., 1990, Mack Publishing, which is incorporated herein by reference.

The vaccine of the present invention can further comprise one or more additional immunomodulatory components such as, e.g., an adjuvant or cytokine, among others. Non-limiting examples of adjuvants that can be used in the vaccine of the present invention include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block co polymer (CytRx, Atlanta Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, Avridine lipid-amine adjuvant, and protein adjuvants such as *Vibrio cholera* toxin and *E. coli* labile toxin. Specific non-limiting examples of oil-in-water emulsions useful in the vaccine of the invention include modified SEAM62 and SEAM 1/2 formulations. Modified SEAM62 is an oil-in-water emulsion containing 5% (v/v) squalene (Sigma), 1% (v/v) SPAN® 85 detergent (ICI Surfactants), 0.7% (v/v) TWEEN® 80 detergent (ICI Surfactants), 2.5% (v/v) ethanol, 200 μg/ml Quil A, 100 μg/ml cholesterol, and 0.5% (v/v) lecithin. Modified SEAM 1/2 is an oil-in-water emulsion comprising 5% (v/v) squalene, 1% (v/v) SPAN®85 detergent, 0.7% (v/v) Tween 80 detergent, 2.5% (v/v) ethanol, 100 μg/ml Quil A, and 50 μg/ml cholesterol. Other immunomodulatory agents that can be included in the vaccine include, e.g., one or more interleukins, interferons, or other known cytokines. Where the vaccine comprises modified live Lawsonia cells, the adjuvant is preferably selected based on the ability of the resulting vaccine formulation to maintain at least some degree of viability of the modified live Lawsonia cells.

Where the vaccine composition comprises a polynucleotide molecule, the polynucleotide molecule can either be DNA or RNA, although DNA is preferred, and is preferably administered to a PPE susceptible animal to be protected against PPE in an expression vector construct, such as a recombinant plasmid or viral vector, as known in the art. Examples of recombinant viral vectors include recombinant adenovirus vectors and recombinant retrovirus vectors. The vaccine formulation can also comprise a non-viral DNA vector, such as a DNA plasmid-based vector. The polynucleotide molecule may be associated with lipids to form, e.g., DNA-lipid complexes, such as liposomes or cochleates. See, e.g., International Patent Publication WO 93/24640.

An expression vector useful as a vaccinal agent in a DNA vaccine preferably comprises a nucleotide sequence encoding one or more antigenic Lawsonia proteins, or a substantial portion of such a nucleotide sequence, in operative association with one or more transcriptional regulatory elements required for expression of the Lawsonia coding sequence in a eukaryotic cell, such as, e.g., a promoter sequence, as known in the art. In a preferred embodiment, the regulatory element is a strong viral promoter such as, e.g., a viral promoter from RSV or CMV. Such an expression vector also preferably includes a bacterial origin of replication and a prokaryotic selectable marker gene for cloning purposes, and a polyadenylation sequence to ensure appropriate termination of the expressed mRNA. A signal sequence may also be included to direct cellular secretion of the expressed protein.

The requirements for expression vectors useful as vaccinal agents in DNA vaccines are further described in U.S. Pat. No. 5,703,055, U.S. Pat. No. 5,580,859, U.S. Pat. No. 5,589,466, International Patent Publication WO 98/35562, and in various scientific publications, including Ramsay et al., 1997, Immunol. Cell Biol. 75:360–363; Davis, 1997, Cur. Opinion Biotech. 8:635–640; Maniackan et al., 1997, Critical Rev. Immunol. 17:139–154; Robinson, 1997, Vaccine 15(8):785–787; Lai and Bennett, 1998, Critical Rev. Immunol. 18:449–484; and Vogel and Sarver, 1995, Clin. Microbiol. Rev. 8(3):406–410, among others.

Where the vaccine composition comprises modified live Lawsonia cells, the vaccine can be stored cold, frozen, or lyophilized. Where the vaccine composition instead comprises a protein, polypeptide, polynucleotide molecule, or inactivated modified Lawsonia cells of the present invention, the vaccine may be stored cold, frozen, or in lyophilized form to be rehydrated prior to administration using an appropriate diluent.

The vaccine of the present invention can optionally be formulated for sustained release of the antigen. Examples of such sustained release formulations include antigen in combination with composites of biocompatible polymers, such as, e.g., poly(lactic acid), poly(lactic-co-glycolic acid), methylcellulose, hyaluronic acid, collagen and the like. The structure, selection and use of degradable polymers in drug delivery vehicles have been reviewed in several publications, including A. Domb et al., 1992, Polymers for Advanced Technologies 3: 279–292, which is incorporated herein by reference. Additional guidance in selecting and using polymers in pharmaceutical formulations can be found in the text by M. Chasin and R. Langer (eds), 1990, "Biodegradable Polymers as Drug Delivery Systems" in: *Drugs and the Pharmaceutical Sciences*, Vol. 45, M. Dekker, NY, which is also incorporated herein by reference. Alternatively, or additionally, the antigen can be microencapsulated to improve administration and efficacy. Methods for microencapsulating antigens are well-known in the art, and include techniques described, e.g., in U.S. Pat. No. 3,137,631; U.S. Pat. No. 3,959,457; U.S. Pat. No. 4,205,060; U.S. Pat. No. 4,606,940; U.S. Pat. No. 4,744,933; U.S. Pat. No. 5,132,117; and International Patent Publication WO 95/28227, all of which are incorporated herein by reference.

Liposomes can also be used to provide for the sustained release of antigen. Details concerning how to make and use liposomal formulations can be found in, among other places, U.S. Pat. No. 4,016,100; U.S. Pat. No. 4,452,747; U.S. Pat. No. 4,921,706; U.S. Pat. No. 4,927,637; U.S. Pat. No. 4,944,948; U.S. Pat. No. 5,008,050; and U.S. Pat. No. 5,009,956, all of which are incorporated herein by reference.

The present invention further provides a method of vaccinating a PPE susceptible animal against PPE, comprising administering to the animal an immunogenically effective amount of a vaccine of the present invention. The vaccine is preferably administered parenterally, e.g., either by subcutaneous or intramuscular injection. However, the vaccine can also be administered by intraperitoneal or intravenous injection, or by other routes, including, e.g., orally, intranasally, rectally, vaginally, intra-ocularly, or by a combination of routes, and also by delayed release devices as known in the art. The skilled artisan can determine optimal routes of vaccine administration, and recognize acceptable formulations for the vaccine composition according to the chosen route of administration.

An effective dosage can be determined by conventional means, starting with a low dose of antigen, and then increasing the dosage while monitoring its effects. Numerous factors may be taken into consideration when determining an optimal dose per animal. Primary among these is the species, size, age and general condition of the animal, the presence of other drugs in the animal, the virulence of a particular strain of Lawsonia against which the animal is being vaccinated, and the like. The actual dosage is preferably chosen after consideration of the results from other animal studies.

The dose amount of a protein or polypeptide of the present invention in a vaccine of the present invention preferably ranges from about 1 $\mu$g to about 10 mg, more preferably from about 50 $\mu$g to about 1 mg, and most preferably from about 100 $\mu$g to about 0.5 mg. The dose amount of a Lawsonia polynucleotide molecule of the present invention in a vaccine of the present invention preferably ranges from about 50 $\mu$g to about 1 mg. The dose amount of modified Lawsonia cells of the present invention in a vaccine of the present invention preferably ranges from about $1\times10^3$ to about $1\times10^8$ cells/ml, and more preferably from about $1\times10^5$ to about $1\times10^7$ cells/ml. A suitable dosage size ranges from about 0.1 ml to about 10 ml, and more preferably from about 1 ml to about 5 ml. The dose amounts of these antigens are also applicable to combination vaccines of the present invention. Where the second component of the combination vaccine is an antigen other than a Lawsonia protein, polypeptide, polynucleotide or modified cell of the present invention, the dose amount of the second component for use in the combination vaccine can be determined from prior vaccine applications of that second component, as known in the art.

The vaccine of the present invention is useful to protect animals, especially pigs, against PPE. The vaccine can be administered to any suitable animals, including, without limitation, hamsters, ferrets, guinea pigs, deer, and bovine, equine, and avian species. The vaccine of the invention can be administered at any time during the life of a particular animal depending upon several factors including, e.g., the timing of an outbreak of PPE among other animals, etc. The vaccine can be administered to animals of weaning age or younger, or to more mature animals. Effective protection may require only a primary vaccination, or one or more booster vaccinations may also be needed. One method of detecting whether adequate immune protection has been achieved is to determine seroconversion and antibody titer in the animal after vaccination. The timing of vaccination and the number of boosters, if any, is preferably determined by a veterinarian based on analysis of all relevant factors, some of which are described above.

In one embodiment, a protein or polypeptide of the invention, e.g., HtrA, PonA, HypC, LysS, YcfW, ABC1, or Omp100 *L. intracellularis* protein, or combinations thereof, is administered in a formulation containing 100 $\mu$g of polypeptide, and 25 μg of *E. coli* labile toxin as adjuvant, in 1 ml of buffered solution. The formulation is, for example, administered intramuscularly to pigs at between 5 and 7 days of age, and readministered 14 days later.

The present invention further provides a kit for vaccinating a PPE susceptible animal against PPE, comprising a container having an immunologically effective amount of a polypeptide, polynucleotide molecule, or modified Lawsonia cells of the present invention, or a combination thereof. The kit can optionally comprise a second container having a pharmaceutically acceptable carrier or diluent. In a preferred embodiment, the polypeptide is the HtrA, PonA, HypC, LysS, YcfW, ABC1, or Omp100 *L. intracellularis* protein; the polynucleotide molecule preferably has a nucleotide sequence that encodes the HtrA, PonA, HypC, LysS, YcfW, ABC1, or Omp100 *L. intracellularis* protein and the modified Lawsonia cells preferably are live or inactivated cells that express an HtrA⁻, PonA⁻, HypC⁻, LysS⁻, YcfW⁻, ABC1⁻, or Omp100⁻ phenotype.

The invention also relates to a kit for detecting the presence of *L. intracellularis*, an *L. intracellularis* specific amino acid or nucleotide sequence, or an anti-*L. intracellularis* antibody, that contains a protein, polypeptide, polynucleotide, or antibody of the invention. The kit can also contain means for detecting the protein, polypeptide, polynucleotide, or antibody of the invention including, for example, an enzyme, fluorescent, or radioactive label attached to the protein, polypeptide, polynucleotide, or antibody, or attached to a moiety that binds to the protein, polypeptide, polynucleotide, or antibody.

The following examples are illustrative only, and not intended to limit the scope of the present invention.

EXAMPLES

Example 1

Molecular Cloning of *L. Intracellularis* Chromosomal Region A

Isolation of DNA and Construction of DNA Libraries

Template DNA was purified from pig intestinal mucosa isolated from the ileum of pigs experimentally infected with *L. intracellularis*. DNA purification from homogenized intestinal mucosa was performed according to (1) the method of Nollau et al. (Nollau et al., 1996, BioTechniques 20: 784–788) or (2) phenol extraction and sodium acetate-ethanol precipitation of DNA. To facilitate cloning of *L. intracellularis* gene sequences, several genomic libraries were constructed. These libraries were specifically modified by ligation of a known sequence (Vectorette II™, Genosys Biotechnologies, Inc., The Woodlands, Tex.) to the 5' and 3' ends of restricted DNA fragments. Vectorette™ libraries were constructed by separately digesting aliquots of *L. intracellularis*-infected pig mucosal DNA extract with restriction endonucleases HindIII, EcoRI, DraI or HpaI at 37° overnight. The reaction was then spiked with additional fresh restriction enzyme and adjusted to 2 mM ATP, 2 mM DTT final concentration. Vectorette™ tailing was carried out by addition of T₄ DNA Ligase (400 U) plus 3 pMol of the appropriate compatible Vectorette™ linker (HindIII Vectorette™: HindIII digested DNA; EcoRI: EcoRI digested DNA; Blunt: DraI, HpaI digested DNA). The mixture was incubated for three cycles at 20°, 60 min; and 37°, 30 min to complete the tailing reaction then adjusted to 200 μl with water and stored at −20°.

Molecular cloning of genomic Region A encoding LysS, YcfW, ABC1, and Omp100 proteins Identification of genomic Region A (shown in FIG. 1) was accomplished by genomic walking and phage library screening processes. Screening of the HindIII, EcoRI, DraI, and HpaI Vectorette™ libraries was carried out to obtain DNA fragments located adjacent to gene (amiB) from *L. intracellularis* having homology to bacterial N-acetylmuramoyl-L-alanine amidases involved in cell wall autolysis. Oligonucleotide primers ER159 (SEQ ID NO: 37), ER161 (SEQ ID NO: 38), and ER162 (SEQ ID NO: 39) were designed based on the nucleotide sequence of amiB. All three primers were designed to bind the (−) strand within this region to allow amplification of DNA located upstream of the gene encoding AmiB.

For polymerase chain amplification of a fragment of the omp100 gene, oligonucleotides ER159 (SEQ ID NO: 37), ER161 (SEQ ID NO: 38), and ER162 (SEQ ID NO: 39) were used in combination with a Vectorette™ specific primer (ER70) (SEQ ID NO: 33) in 50 μl reactions containing 1×PCR Buffer II (Perkin Elmer), 1.5 mM MgCl₂, 200 μM each deoxy-NTP, 50 pMol each primer, and 2.5 U AmpliTaq™ Gold (Perkin Elmer) thermostable polymerase. Multiple single reactions were performed with 4 μl of the Vectorette™ libraries as DNA template. Amplification was carried out as follows: denaturation (95° 9 min); 40 cycles of denaturation (95° 30 sec), annealing (65° 30 sec), and polymerization (72° 2.5 min); followed by a final extension at 72° for 7 minutes.

The amplified products were visualized by separation on a 1.2% agarose gel (Sigma). An approximately 2.5 kb product resulted from amplification of the HpaI Vectorette™ library when either ER159 or ER162 were used in combination with the Vectorette™-specific primer, ER70. This fragment represented a 1.9 kb region immediately upstream of the *L. intracellularis* gene encoding AmiB. The PCR product was purified following agarose gel electrophoresis using JETsorb™ kit (GENOMED, Inc., Research Triangle Park, N.C.) and cloned into pCR2.1 Topo (Invitrogen, Carlsbad, Calif.) to generate plasmid pER393. The insert was partially sequenced using vector specific primers. The sequence obtained was analyzed by the BLASTx algorithm (Altschul et al., 1990, *J. Mol. Biol.* 215:403–10) and shown to partially encode a protein with similarity to an approximately 85 kDa protein in the GenBank database. The reported proteins from *Neisseria meningitidis, Haemophilus influenzae*, and *Pasteurella multocida* were Omp85, protective surface antigen D15, and Oma87, respectively.

Based on the newly identified sequence of this partial gene fragment (encoding about the C-terminal 2/3 of the Omp100 protein) specific primers ER174 (SEQ ID NO: 46) and ER175 (SEQ ID NO: 47) were designed to obtain additional 5' flanking sequences by a second round of screening the Vectorette™ libraries by PCR amplification. Oligonucleotides ER174 (SEQ ID NO: 46) and ER175 (SEQ ID NO: 47) were used in combination with primer ER70 (SEQ ID NO: 33) in 50 μl reactions containing 1×PCR Buffer II (Perkin Elmer), 1.5 mM MgCl₂, 200 μM each deoxy-NTP, 50 pMol each primer, and 2.5 U AmpliTaq Gold (Perkin Elmer) thermostable polymerase. Multiple single reactions were performed with 2 μl of the Vectorette™ EcoRI and DraI libraries as DNA template. Amplification was carried out as follows: denaturation (95° 9 min); 35 cycles of denaturation (95° 30 sec), annealing (62° 30 sec), and polymerization (72° 2.5 min); followed by a final extension at 72° for 7 minutes.

Screening of the EcoRI and DraI Vectorette™ libraries by PCR (employing either ER174 or ER175 in combination with ER70) resulted in successful amplification of an approximately 1.4 kb fragment from the EcoRI Vectorette™ library. The PCR product was purified following agarose gel electrophoresis using JETsorb™ kit and cloned into pCR2.1 Topo to generate plasmid pER394. Sequence analysis of the insert termini within pER394 using ER175 and a vector specific primer confirmed this fragment was contiguous (e.g. overlapped) with the fragment insert within pER393 and allowed determination of the 5' end of the omp100 gene. This analysis also indicated the presence of an additional partial ORF having homology to the ATP-binding cassette (ABC) superfamily of transporter proteins. Accordingly, the encoded partial protein was designated ABC1.

Based on the newly identified nucleotide sequence of this partial gene fragment (encoding about the C-terminal 1/2 of the ABC1 protein) specific primer ER188 (SEQ ID NO: 55) was designed to obtain additional 5' flanking sequence by a third round of screening the Vectorette™ libraries by PCR amplification. Oligonucleotide ER188 (SEQ ID NO: 55) was used in combination with primer ER70 (SEQ ID NO: 33) in 50 μl reactions containing 1×PCR Buffer II, 1.5 mM MgCl$_2$, 200 μM each deoxy-NTP, 50 pMol each primer, and 2.5 U AmpliTaq™ Gold thermostable polymerase. Multiple single reactions were performed with 4 μl of the Vectorette™ HindIII, DraI, and HpaI libraries as DNA template. Amplification was carried out as follows: denaturation (95° 9 min); 30 cycles of denaturation (95° 30 sec), annealing (60° 30 sec), and polymerization (72° 2.5 min); followed by a final extension at 72° for 7 minutes.

Screening of the HindIII, DraI, and HpaI Vectorette™ libraries by PCR (employing ER188 in combination with ER70) resulted in successful amplification of an approximately 0.8 kb fragment from the HindIII Vectorette™ library. The PCR product was purified following agarose gel electrophoresis using JETsorb™ kit and cloned into pCR2.1 Topo to generate plasmid pER395. Sequence analysis of the insert termini within pER395 using ER188 and vector specific primers confirmed this fragment was contiguous (e.g. overlapped) with the fragment insert within pER394 and allowed determination of the 5' end of the abc1 gene. An additional partial ORF was identified upstream of the abc1 gene. The encoded protein was designated YcfW based on its homology with the conserved protein, YcfW, found in numerous bacteria.

The region encoding the remaining portion of the ycfW ORF was obtained by screening a Lambda ZAP Express™ phage library created by partial Tsp59I digestion of L. intracellularis genomic DNA. The phage library was plated onto XL1-Blue MRF' E. coli cells in the presence of 10 mM MgSO$_4$, IPTG, and X-Gal. Clear plaques were picked and phage inserts were amplified using the Expand Long Template PCR System™ as recommended by the supplier (Boehringer Mannheim, Indianapolis, Ind.). The T3 and T7 phage specific primers were used in PCR conditions consisting of denaturation (94° 2 min); 25 cycles of denaturation (94° 10 sec), annealing (50° 30 sec), and polymerization (68° 6 min); followed by a final extension at 68° for 7 min. Resulting PCR products were end-sequenced using the T3 and T7 primers and compared to genes in the GeneBank database by BLASTx analysis. One phage, designated clone A21, contained an approximately 6.1 kb insert encompassing 2.8 kb which overlapped the previously identified ycfW, ABC1, and omp100 DNA sequence. Accordingly this clone was used to determine the DNA sequence encoding the N-terminus of the YcfW protein. An additional ORF was identified upstream of the ycfW gene. This gene encoded a protein which shares homology with several lysyl-tRNA synthetases and was designated lysS.

The preliminary nucleotide sequence for the omp100 and C-terminal portion of the abc1 genes was obtained by sequencing the inserts within pER393 and pER394. Preliminary nucleotide sequence encoding the C-terminal 141 amino acid portion of YcfW and amino-terminal portion of ABC1 was obtained by sequencing the insert within pER395. Preliminary nucleotide sequence encoding the lysS and N-terminal portion of the ycfW gene was obtained by sequencing the PCR product representing the insert contained in phage clone A21. The primers employed for preliminary sequencing included the vector-specific M13 forward, M13 reverse, phage. T3 and T7 primers in addition to ER159 (SEQ ID NO: 37), ER169 (SEQ ID NO: 41), ER170 (SEQ ID NO: 42), ER176 (SEQ ID NO: 48), and ER177 (SEQ ID NO: 49) for pER393; ER175 (SEQ ID NO: 47), ER185 (SEQ ID NO: 52), ER186 (SEQ ID NO: 53), and ER187 (SEQ ID NO: 54) for pER394; ER188 (SEQ ID NO: 55) for pER395; and ER246 (SEQ ID NO: 97), ER254 (SEQ ID NO: 98), ER255 (SEQ ID NO: 99), ER256 (SEQ ID NO: 100), and ER257 (SEQ ID NO: 101) for phage clone A21. Specific PCR Amplification of Subgenomic DNA Fragments Encompassing L. intracellularis Region A Results of the cloning and preliminary sequencing from the genomic fragments contained in plasmids pER393, pER394, pER395 and phage clone A21 were used to design oligonucleotide primers for the specific amplification of overlapping subgenomic fragments directly from L. intracellularis-infected pig mucosal DNA extracts. DNA extraction was carried out according to the methods described above. This approach was preferred based on the desire to eliminate introduction of sequencing artifacts due to possible mutations arising during the cloning of gene fragments in E. coli. Oligonucleotides ER246 (SEQ ID NO: 97) and ER254 (SEQ ID NO: 98), which flank the lysS and N-terminal ¾ of ycfW, oligonucleotides ER229 (SEQ ID NO: 73) and ER206 (SEQ ID NO: 66), which flank the abc1 gene; and ER231 (SEQ ID NO: 75) and ER232 (SEQ ID NO: 76), which flank the omp100 gene, were used to specifically amplify this region from the mucosal DNA extract. The lysS gene was amplified in a PCR reaction containing 2 pt mucosal DNA extract as template, 1×PC2 buffer (Ab Peptides, Inc.), 200 μM each dNTP, 50 pMol each primer, 7.5 U KlenTaq1 and 0.15 U cloned Pfu thermostable polymerases in a 50 μl final sample volume. Conditions for amplification consisted of denaturation at 94° for 5 minutes followed by 30 cycles of denaturation (94° 1 minute), annealing (55° 30 seconds), and polymerization (72° 3 minutes). A final extension at 72° for 7 minutes completed the amplification of the targeted 2.6 kb region. The abc1 gene was amplified in triplicate PCR reactions containing 1 μl mucosal DNA extract as template, 1×PC2 buffer, 200 μM each dNTP, 50 pMol each primer, 7.5 U KlenTaq1 and 0.15 U cloned Pfu thermostable polymerases in a 50 μl final sample volume. Conditions for amplification consisted of denaturation at 95° for 5 min followed by 33 cycles of denaturation (94° 1 min), annealing (58° 30 sec), and polymerization (72° 80 sec). A final extension at 72° for 10 minutes completed the amplification of the targeted gene region. The omp100 gene was amplified in quadruplicate PCR reactions containing 2 μl mucosal DNA extract as template, 1×PC2 buffer, 200 μM each dNTP, 50 pMol each primer, 7.5 U KlenTaq1 and 0.15 U cloned Pfu thermostable polymerases in a 50 μl final sample volume. Conditions for amplification consisted of denaturation at 94° for 5 min followed by 35 cycles of denaturation (94° 30 sec), annealing (60° 30 sec), and polymerization (72° 3 min). A final extension at 72° for 7 minutes completed the amplification of the targeted gene region. Following amplification, each of the samples were pooled if appropriate and the specific product was purified by agarose gel electrophoresis prior to direct sequence analysis using DyeDeoxy™ termination reactions on an ABI automated DNA sequencer (Lark Technologies, Inc., Houston, Tex.).

Synthetic oligonucleotide primers were used to sequence both DNA strands of the amplified products from *L. intracellularis*. The primers used for sequence analysis included: AP58.1 (SEQ ID NO: 26), AP58.2 (SEQ ID NO: 27), AP59.1 (SEQ ID NO: 28), AP59.2 (SEQ ID NO: 29), AP59.3 (SEQ ID NO: 30), AP59.4 (SEQ ID NO: 31), AP59.5 (SEQ ID NO: 32), ER159 (SEQ ID NO: 37), ER169 (SEQ ID NO: 41), ER170 (SEQ ID NO: 42), ER175 (SEQ ID NO: 47), ER176 (SEQ ID NO: 48), ER177 (SEQ ID NO: 49), ER185 (SEQ ID NO: 52), ER186 (SEQ ID NO: 53), ER187 (SEQ ID NO: 54), ER188 (SEQ ID NO: 55), ER205 (SEQ ID NO: 65), ER206 (SEQ ID NO: 66), ER217 (SEQ ID NO: 71), ER229 (SEQ ID NO: 73), ER230 (SEQ ID NO: 74), RA138 (SEQ ID NO: 79), RA139 (SEQ ID NO: 80), RA140 (SEQ ID NO: 81), AP182.1 (SEQ ID NO: 83), AP182.2 (SEQ ID NO: 84), AP182.3 (SEQ ID NO: 85), AP182.4 (SEQ ID NO: 86), AP182.5 (SEQ ID NO: 87), AP182.6 (SEQ ID NO: 88), AP182.7 (SEQ ID NO: 89), AP182.8 (SEQ ID NO: 90), AP182.9 (SEQ ID NO: 91), AP182.10 (SEQ ID NO: 92), AP182.11 (SEQ ID NO: 93), AP182.12 (SEQ ID NO: 94), AP182.13 (SEQ ID NO: 95), AP182.14 (SEQ ID NO: 96), ER246 (SEQ ID NO: 97), ER254 (SEQ ID NO: 98), ER255 (SEQ ID NO: 99), ER256 (SEQ ID NO: 100), and ER257 (SEQ ID NO: 101).

The nucleotide sequence of the *L. intracellularis* genomic Region A is listed in SEQ ID NO: 1. The deduced amino acid sequences of the encoded LysS, YcfW, ABC1, and Omp100 proteins within this region are presented in SEQ ID NO: 102, SEQ ID NO: 3, SEQ ID NO: 4, and SEQ ID NO: 5, respectively.

Molecular Analysis of the *L. Intracellularis* Genes and Gene Products Specified by Region A The *L. intracellularis* chromosomal Region A identified upstream of the amiB gene encodes proteins designated LysS, YcfW, ABC1, and Omp100 (FIG. 1). These genes are encoded by the same DNA strand and are very closely arranged. This organization suggests these genes may be part of an operon and are likely translationally coupled in the case of LysS/YcfW and ABC1/Omp100. The lysS ORF likely initiates from an atypical TTG initiation codon and would extend from nucleotide 165–1745 of SEQ ID. NO: 1. This gene encodes a deduced 526 amino acid protein, designated LysS (SEQ ID NO: 102), having a theoretical molecular weight of about 60,628 daltons. The ycfW ORF extends from nucleotide 1745–3028 of the reported sequence (SEQ ID NO: 1). This gene encodes a deduced 427 amino acid protein, designated. YcfW (SEQ ID NO: 3), having a theoretical molecular weight of about 46,957 daltons. The abc1 ORF extends from nucleotide 3031–3738 of SEQ ID NO: 1, and encodes a deduced 235 amino acid protein, ABC1 (SEQ ID NO: 4), having a theoretical molecular weight of about 25,618 daltons. Further downstream but overlapping this ORF by 44 nucleotides is an additional large open reading frame. This ORF, which was designated omp100, extends from nucleotide 3695–6388 of SEQ ID NO: 1. The omp100 gene encodes a deduced 896 amino acid protein which was designated Omp100 (SEQ ID NO: 5). The Omp100 protein has a theoretical molecular weight of about 101,178 daltons.

Similarity of *L. Intracellularis* LysS Protein to lysyl-tRNA Synthetases.

The deduced amino acid sequence of the LysS protein (SEQ ID NO: 102) was compared to other proteins reported in GeneBank by the BLASTp algorithm (Altschul, S. F et al., 1997, *Nucleic Acids Res*. 25:3389–3402) and aligned by the CLUSTAL W algorithm (Thompson, J. D. et al., 1994, *Nucleic Acids Res*. 22:4673–4680). As shown in FIG. 9, this analysis indicated that LysS shares similarity with members of the cytoplasmic lysyl-tRNA synthetase family. The *L. intracellularis* LysS protein shares 47% identity with the lysyl-tRNA synthetase protein (Accn. AB012100) from *Bacillus stearothermophilus*. Consistent with its cytoplasmic location no secretion signal sequence was identified near the predicted N-terminus of this protein.

Similarity of *L. Intracellularis* YcfW and ABC1 Proteins to Other Hypothetical Proteins The YcfW protein shares limited homology with a family of conserved hypothetical proteins approximately 4045 kDa in side. Members of this family are reported to be transmembrane or integral membrane proteins. A structural prediction comparison of representative proteins from this family was carried out using TMPred (EMBnet—European Molecular Biology Network; http://www.ch.embnet.org/index.html). The TMpred program makes a prediction of membrane-spanning regions and their orientation. The algorithm is based on the statistical analysis of TMbase, a database of naturally occurring transmembrane proteins. (Hofmann & Stoffel, 1993, *Biol. Chem*. Hoppe-Seyler 347:166). This analysis indicates that homologs within this protein family have three strong transmembrane domains clustered near the C-terminus of the protein. We have noted an extremely well conserved domain at the very carboxyl-terminal four amino acids (LRYE) of representatives from this family. The observation that the C-terminal region contains multiple transmembrane domains while the extreme C-terminus is highly conserved suggests a universal functional requirement associated with this region of the YcfW family of homologous proteins. The *L. intracellularis* YcfW protein presented in SEQ ID NO: 3 also contains three C-terminal transmembrane domains in addition to the extreme C-terminal amino acids (LRYE). In addition to the three-carboxyl domains above, TMPred analysis indicates that residues 1944 of the YcfW protein are likely to form a transmembrane region. The amino terminus of YcfW was also examined by the PSORT (Ver. 6.4) computer algorithm using networks trained on known secretion signal sequences. This analysis indicates that residues 29–45 are likely to form a transmembrane region (P. Klein et al., 1985, *Biochim. Biophys. Acta*, 815:468) which is predicted to act as an uncleavable signal sequence (D. J. McGeoch, Virus Research, 3:271, 1985 and G. von Heijne. *Nucl. Acids Res.*, 14:4683, 1986). As shown in FIG. 2, the 427 amino acid *L. intracellularis* YcfW protein shares 32% identity with a 415 residue hypothetical protein (Accn. AJ235272) from *Rickettsia prowazekii*.

The deduced amino acid sequence of the ABC1 protein (SEQ ID NO: 4) was compared to other known proteins reported in GenBank by the BLASTp algorithm. An especially well conserved region (GASGSGKS) was identified near the amino terminus of ABC1. This region corresponds to the nucleotide-binding motif A (P-loop) present in ABC-type transporters. The ABC-type proteins consist of a very large superfamily of proteins which have a wide variety of cellular functions. The majority of these proteins are classified as ABC-type proteins based on regional homology within the nucleotide-binding motif and are generally thought to be involved in cellular transport functions. FIG. 3 shows an alignment of ABC1 with that of YcfV from *E. coli*, (Accn. AE000212) which shares about 45% identical amino acid residues. The *E. coli* YcfV protein is a probable ABC-type transport protein.

Similarity of *L. Intracellularis* Omp100 Protein to 85 kDa Proteins

Examination of the amino terminus of Omp100 indicates that amino acids 1–25 are hydrophobic and positively charged which is characteristic of signal sequences (von Heijm, 1985, *J. Mol Biol.* 184:99–105). The SignalP (Ver. 1.1) computer algorithm (Nielsen, H., et. al., 1997, *Prot. Engineering*, 10:1–6; http://www.cbs.dtv.dk/services/signalP/), using networks trained on known signal sequences, predicted the most likely cleavage site between amino acids 25 and 26. Thus amino acids 1–25 are predicted to be removed from Omp100 during the outer membrane localization process. The Omp100 C-terminal amino acid is predicted to be a phenylalanine residue, a feature consistent with the correct localization of outer membrane proteins (Struyve, M., 1991, *J. Mol Biol.* 218:141–148).

The deduced amino acid sequence of the Omp100 protein (SEQ ID NO: 5) was compared to other known proteins reported in GenBank by the BLASTp algorithm (Altschul, S. F et al., 1997, *Nucleic Acids Res.* 25:3389–3402) and aligned by the CLUSTAL W algorithm (Thompson, J. D. et al., 1994, *Nucleic Acids Res.* 22:4673–4680). As shown in FIG. 4, this analysis indicated Omp100 shares limited similarity with an approximately 85 kDa protein in the GenBank database (designated U70214). Alignment of the C-terminal ends of Omp100 and this hypothetical protein (YaeT, Accn. U70214 or AE000127) from *E. coli* indicate these proteins share about 23% identical residues. Other reported proteins include those identified from *Shigella flexneri* (Oma90), *Neisseria meningitidis* (Omp85), *Haemophilus influenzae* (D15), and *Pasteurella multocida* (Oma87), among others. The $NH_2$ terminal portion including amino acids 1–139 does not align with any known protein. An additional search of GenBank with the BLASTp algorithm using only the region encompassing amino acids 1–200 of the encoded Omp100 protein failed to detect any known Omp85-like proteins. This data indicates that the amino terminal portion of Omp100 is entirely unique to *L. intracellularis*.

Example 2

Molecular Cloning of *L. Intracellularis* Chromosomal Region B

Molecular Cloning of Genomic Region B encoding PonA, HtrA, HypC, and ORF1 Proteins Identification of genomic Region B (shown in FIG. 1) was accomplished by a genomic walking: process similar to that described for identification of genomic Region A. Screening of the HindIII, EcoRI, DraI, and HpaI Vectorette™ libraries was carried out to obtain DNA fragments located adjacent to gene flgE from *L. intracellularis* which encodes a protein with homology to the flagellar hook protein of other bacteria. Oligonucleotide primers ER142 (SEQ ID NO: 34), ER153 (SEQ ID NO: 35), and ER158 (SEQ ID NO: 36) were designed based on the known nucleotide sequence 3' of flgE. All three primers were designed to bind the (+) strand within this region to allow amplification of DNA located downstream of the gene encoding FlgE.

For polymerase chain amplification of a fragment of the ponA gene, oligonucleotides ER142 (SEQ ID NO: 34), ER153 (SEQ ID NO: 35), and ER158 (SEQ ID NO: 36) were used in combination with a Vectorette™ specific primer (ER70) (SEQ ID NO: 33) in 50 µl reactions containing 1×PCR Buffer II, 1.5 mM $MgCl_2$, 200 µM each deoxy-NTP, 50 pMol each primer, and 2.5 U AmpliTaq™ Gold thermostable polymerase. Multiple single reactions were performed with 4 µl of the Vectorette™ libraries as DNA template. Amplification annealing temperatures, extension times, and number of cycles varied between experiments and were carried out over the following ranges: denaturation (95° 9 min); 35–40 cycles of denaturation (95° 30 sec), annealing (50–60° 30 sec), and polymerization (72° 2.5–3 min); followed by a final extension at 72° for 7 minutes.

The amplified products were visualized by separation on a 1.2% agarose gel. An approximately 1.2 kb product resulted from amplification of the DraI Vectorette™ library when ER158 (SEQ ID NO: 36) was used in combination with the Vectorette™-specific primer, ER70. Conditions leading to specific amplification of this product included denaturation (95° 9 min); 40 cycles of denaturation (95° 30 sec), annealing (60° 30 sec), and polymerization (72° 2.5 min); followed by a final extension at 72° for 7 minutes. This fragment represented a 1.4 kb region immediately downstream of the *L. intracellularis* gene encoding FlgE. The PCR product was purified following agarose gel electrophoresis using a JETsorb™ kit and cloned into pCR2.1 Topo to generate plasmid pER390. The insert was partially sequenced using ER70 and ER158 primers. The sequence obtained was analyzed by the BLASTx algorithm (Altschul, S. F. et al., 1990) and shown to encode a polypeptide with similarity to the amino terminal one half of penicillin-binding proteins in the GenBank database.

Based on the newly identified sequence of this partial gene, primer ER163 (SEQ ID NO: 40) was designed to obtain additional 3' flanking sequences by a second round of screening the Vectorette™ libraries. Oligonucleotide ER163 (SEQ ID NO: 40) was used in combination with primer ER70 (SEQ ID NO: 33) in 50 µl reactions containing 1×PCR Buffer II, 1.5 mM $MgCl_2$, 200 µM each deoxy-NTP, 50 pMol each primer, and 2.5 U AmpliTaq Gold thermostable polymerase; Multiple single reactions were performed with 2 µl of the Vectorette™ HindIII, EcoRI and HpaI libraries as DNA template. Amplification was carried out as follows: denaturation (95° 9 min); 30 cycles of denaturation (95 ° 30 sec), annealing (62° 30 sec), and polymerization (72° 1.5 min); followed by a final extension at 72° for 7 minutes.

A 2.7 kb fragment was amplified from the HindIII Vectorette™ library. The PCR product was purified following agarose gel electrophoresis using JETsorb™ kit and cloned into pCR2.1 Topo to generate plasmid pER392. Sequence analysis of the cloned insert termini using vector specific primers confirmed this fragment was contiguous with the fragment insert within pER390. This analysis also indicated the presence of an additional partial ORF corresponding to approximately the $NH_2$-terminal 400 residues of the HtrA protein family of serine proteases. Accordingly, the encoded partial protein was designated HtrA.

A third round of genomic walking was carried out to identify additional sequence within the htrA ORF. Specific primer ER173 (SEQ ID NO: 45) was designed based on the known sequence near the 3' end of the insert within pER392. Oligonucleotide ER173 (SEQ ID NO: 45) was used in combination with primer ER70 (SEQ ID NO: 33) in 50 µl reactions as above. Multiple single reactions were performed with 2 µl of the Vectorette™ DraI and HpaI libraries as DNA template. Amplification (denaturation (95° 9 min); 35 cycles of denaturation (95° 30 sec), annealing (62° 30 sec), and polymerization (72° 2.5 min); followed by a final extension at 72° for 7 minutes) resulted in production of a 0.3 kb fragment from the: DraI library. The PCR product was purified following agarose gel electrophoresis using a JETsorb™ kit, cloned into pCR2.1 Topo, and the insert sequenced on both strands using vector specific primers. Sequence and BLASTx analysis indicated that the htrA ORF remained open through the 3' end of the cloned fragment and that an additional 10 amino acids would be expected to remain before the end of the encoded HtrA protein.

A final round of genomic walking was carried out to identify the remainder of the htrA ORF and 3' flanking region. Specific primer ER189 (SEQ ID NO: 56) was designed based on the known sequence near the 3' end of the htrA ORF. Oligonucleotide ER189 (SEQ ID NO: 56) was used in combination with primer ER70 (SEQ ID NO: 33) in 50 µl reactions as above. Multiple single reactions were performed with 4 µl of the Vectorette™ HindIII, EcoRI, and HpaI libraries as DNA template. Amplification was carried out as follows: denaturation (95° 9 min); 30 cycles of denaturation (95° 30 sec), annealing (60° 30 sec), and polymerization (72° 2.5 min); followed by a final extension at 72° for 7 minutes. Amplification resulted in production of an approximately 1 kb fragment from the EcoRI library. The PCR product was purified following agarose gel electrophoresis using a JETsorb™ kit and cloned into pCR2.1 Topo to generate. pER3966. Sequence analysis of the insert termini within pER396 using vector specific primers allowed determination of the 3' end of the htrA gene. An additional small ORF was identified downstream of the htrA gene. The encoded protein was designated HypC based on its homology with the HypC protein found, in other bacteria. Further downstream from hypC is an additional partial ORF, designated orf1, which is encoded by the opposite DNA strand. This truncated 177 amino acid polypeptide was designated ORF1.

The preliminary nucleotide sequence for the ponA, htrA, hypC, and C-terminal portion of the orf1 genes was obtained by sequencing the inserts within pER390, pER392 and pER396. The primers employed for preliminary sequencing included the vector-specific M13 forward and M13 reverse primers in addition to ER193 (SEQ ID NO: 59) and ER194 (SEQ ID NO: 60) for pER390; ER171 (SEQ ID NO: 43), ER172 (SEQ ID NO: 44), ER178 (SEQ ID NO: 50), ER179 (SEQ ID NO: 51), ER190 (SEQ ID NO: 57), and ER191 (SEQ ID NO: 58) for pER392; and ER195 (SEQ ID NO: 61) and ER196 (SEQ ID NO: 62) for pER396.

Specific PCR Amplification of Subgenomic DNA Fragments Encompassing L. intracellularis Region B Results of the cloning and preliminary sequencing from the genomic fragments contained in plasmids pER390, pER392, and pER396 were used to design oligonucleotide primers for the specific amplification of overlapping subgenomic fragments directly from L. intracellularis-infected pig mucosal DNA extracts (methods described above for DNA extraction were employed). This approach was preferred based on the desire to eliminate introduction of sequencing artifacts due to possible mutations arising during the cloning of gene fragments in E. coli. Oligonucleotides ER228 (SEQ ID NO: 72) and ER190 (SEQ ID NO: 57), which flank the ponA gene; oligonucleotides ER207 (SEQ ID NO: 67) and RA134 (SEQ ID NO: 78), which flank the htrA gene; and oligonucleotides ER189 (SEQ ID NO: 56) and ER196 (SEQ ID NO: 62), which flank the hypC gene were used to specifically amplify this region from the mucosal DNA extract. The endpoints of these fragments overlap thereby allowing specific amplification of subgenomic DNA fragments which are contiguous followed by subsequent confirmation by comparing the terminal nucleotide sequences present in each unique, overlapping DNA fragment. Accordingly, the final sequence represents the complete L. intracellularis genomic Region B.

The overlapping ponA, htrA, and hypC gene regions were amplified in triplicate PCR reactions each containing 1 µl mucosal DNA extract as template, 1×PC2 buffer (Ab Peptides, Inc.), 200 µM each dNTP, 50 pMol each primer, 7.5 U KlenTaq1 and 0.15 U cloned Pfu thermostable polymerases in a 50 µl final sample volume. Conditions for amplification of ponA consisted of denaturation at 95° for 5 min followed by 33 cycles of denaturation (95° 30 sec), annealing (62° 30 sec), and polymerization (72° 3 min). Conditions for amplification of htrA consisted of denaturation at 94° for 5 min followed by 33 cycles of denaturation (95° 30 sec), annealing (58° 30 sec), and polymerization (72° 3 min). Conditions for amplification of hypC consisted of denaturation at 94° for 5 min followed by 33 cycles of denaturation (95° 30 sec), annealing (62° 30 sec), and polymerization (72° 80 sec). A final extension at 72° for 7 minutes completed the amplification of each of the targeted gene regions. Following amplification, each of the samples were pooled separately and the specific product was purified by agarose gel electrophoresis prior to direct sequence analysis using DyeDeoxy™ termination reactions on an ABI automated DNA sequencer (Lark Technologies, Inc., Houston, Tex.).

Synthetic oligonucleotide primers were used to sequence both DNA strands of the amplified products from L. intracellularis. The primers used for sequence analysis included: AP55.1 (SEQ ID NO: 10), AP55.2 (SEQ ID NO: 11), AP55.3 (SEQ ID NO: 12), AP55.4 (SEQ ID NO: 13), AP55.5 (SEQ ID NO: 14), AP55.6 (SEQ ID NO: 15), AP55.7 (SEQ ID NO: 16), AP55.8 (SEQ ID NO: 17), AP55.9 (SEQ ID NO: 18), AP55.10 (SEQ ID NO: 19), AP55.11 (SEQ ID NO: 20), AP56.1 (SEQ ID NO: 21), AP56.2 (SEQ ID NO: 22), AP56.3 (SEQ ID NO: 23), AP57.1 (SEQ ID NO: 24), AP57.2 (SEQ ID NO: 25), ER158 (SEQ ID NO: 36), ER163 (SEQ ID NO: 40), ER171 (SEQ ID NO: 43), ER172 (SEQ ID NO: 44), ER173 (SEQ ID NO: 45), ER178 (SEQ ID NO: 50), ER179 (SEQ ID NO: 51), ER189 (SEQ ID NO: 56), ER190 (SEQ ID NO: 57), ER191 (SEQ ID NO: 58), ER193 (SEQ ID NO: 59), ER194 (SEQ ID NO: 60), ER195 (SEQ ID NO: 61), ER196 (SEQ ID NO: 62), ER203 (SEQ ID NO: 63), ER204 (SEQ ID NO: 64), ER207 (SEQ ID NO: 67), ER208 (SEQ ID NO: 68), ER213 (SEQ ID NO: 69), ER228 (SEQ ID NO: 72), RA133 (SEQ ID NO: 77), RA134 (SEQ ID NO: 78), and RA171 (SEQ ID NO: 82).

The nucleotide sequence of the L. intracellularis genomic Region B is listed in SEQ ID NO: 2. The deduced amino acid sequences of the encoded PonA, HtrA, HypC, and ORF1 proteins within this region are presented in SEQ ID NO: 6, SEQ ID NO: 7, and SEQ ID NO: 8, and SEQ ID NO: 9, respectively.

Molecular Analysis of the L. intracellularis Genes and Gene Products Specified by Region B The L. intracellularis chromosomal Region B identified downstream of the flgE gene encodes proteins designated PonA, HtrA, HypC, and a partial "ORF1" protein (FIG. 1). A portion of the flgE ORF is presented here and extends from nucleotide 1–125 (SEQ ID NO: 2). The ponA ORF extends from nucleotide 252–2690 of SEQ ID NO: 2, and encodes a deduced 812 amino acid protein, PonA (SEQ ID NO: 6), having a theoretical molecular weight of about 90,263 daltons. An alternative in-frame translation initiation codon is present at nucleotide 276 which, if utilized, would encode a slightly smaller 804 amino acid protein having a theoretical molecular weight of about 89,313 daltons. The htrA ORF extends from nucleotide 2981–4315 of SEQ ID NO: 2, and encodes a deduced 474 amino acid protein, HtrA (SEQ ID NO: 7), having a theoretical molecular weight of about 50,478 daltons. The small hypC ORF extends from nucleotide 4581–4829 of SEQ ID NO: 2, and encodes a deduced 82 amino acid protein, HypC (SEQ ID NO: 8), having a theoretical molecular weight of about 8,888 daltons. Further downstream and transcribed in the opposite orientation is an additional open reading frame. This ORF, which was designated "orf1", extends from nucleotide 4912–5445 at the 3' end of SEQ ID NO: 2. This ORF remains open through the 3' end of SEQ ID NO: 2 and thus encodes the C-terminal 177 amino acids of a truncated protein having a theoretical molecular weight of at least about 20,345 daltons. As shown in FIG. 8, the encoded ORF1 protein (SEQ ID NO: 9) shares limited homology with a 205 amino acid hypothetical protein encoded by gene "MJ1123" (Accn. U67555) from the *Methanococcus jannaschii* genome.

Similarity of *L. intracellularis* HypC Protein to Hydrogenase Maturation Proteins The HypC protein shares homology with the hyp/hup family of hydrogenase maturation proteins. Hydrogenase, which catalyzes the reversible oxidation of molecular hydrogen, is involved in many relevant anaerobic processes where hydrogen is oxidized or produced (Adams, M. W. W., et al., 1980, *Biochem. Biophys. Acta* 594:105–176). The HypC protein is required for the maturation of catalytically active hydrogenase isozymes in *E. coli*. The precise role of HypC in this process is unknown but hydrogenase maturation involves nickel insertion, protein folding, C-terminal proteolytic processing, membrane integration, and reductive activation (Lutz, S., et al., 1991, *Mol. Microbiol.* 5:123–135; Przybyla, A. E., et al., 1992, *FEMS Microbiol. Rev.* 88:109–136). The HypC protein is 41% identical to the Desulfovibrio gigas 82 amino acid HynD protein (Accn. AJ223669, as shown in FIG. 7) and 39% identical to the 75 amino acid HypC protein from *Rizobium leguminosarum*.

Similarity of *L. Intracellularis* PonA Protein to Penicillin Binding Proteins

The ponA ORF encodes a deduced 812 amino acid protein, having a theoretical molecular weight of about 90,263 daltons. An alternative in-frame methionine codon is present which encodes a slightly smaller 804 amino acid protein having a theoretical molecular weight of about 89,313 daltons. Similar in-frame methionine codons have been identified in other characterized ponA ORF's. For example, PonA homologs from *Neisseria flavescens* (Accn. AF087677), *N. gonorrhoeae* (Accn. U72876), and *N. meningitidis* (Accn. U80933) contain amino-terminal in-frame methionine codons separated by 8, 6, and 6 codons, respectively. As with *L. intracellularis*, the neisserial ponA genes are preceded by undiscernable ribosome binding sites thus further complicating prediction of the true initiating methionine. N-terminal sequencing of the *N. gonorrhoeae* FA19 PonA protein indicated the second methionine was the preferred start site in this strain (Ropp et al., 1997, *J. Bacteriol.* 179:2783–2787). The upstream methionine codon was used as the putative initiation site for the encoded PonA protein from *L. intracellularis*.

A structural prediction of the PonA protein was carried out using TMPred. The TMpred program makes a prediction of membrane-spanning regions and their orientation (K. Hofmann & W. Stoffel, 1993. TMbase—A database of membrane spanning proteins segments. *Biol. Chem*. Hoppe-Seyler 347:166). This analysis indicates that PonA has a strong transmembrane domain at the NH$_2$-terminus of the protein. The amino terminus of PonA was examined by the PSORT (Ver. 6.4) computer algorithm using networks trained on known signal sequences. This analysis indicates that residues 16–32 are likely to form a transmembrane region (P. Klein et al., 1985, *Biochim. Biophys. Acta*, 815:468) which is predicted to act as an uncleavable signal sequence (D. J. McGeoch, *Virus Research*, 3:271, 1985 and G. von Heijne, *Nucl. Acids Res.*, 14:4683, 1986). Thus the amino terminus of PonA is predicted to anchor the protein to the bacterial inner membrane, which is similar to the method of localization of other penicillin-binding proteins.

The PonA protein shares homology with Class A high-molecular-mass penicillin-binding proteins (PBP's) identified in other bacteria. Penicillin-binding proteins are bacterial cytoplasmic membrane proteins involved in the final steps of peptidoglycan synthesis. The Class A proteins generally exhibit two types of enzymatic activities: the glycosyltransferase, which polymerizes the glycan strand and the transpeptidase, which cross-links these strands by their peptide side chains. These reactions are catalyzed either on the outer surface of the cytoplasmic membrane or further outside and the major fraction of the proteins involved in peptidoglycan synthesis is therefore localized in the periplasm. The deduced amino acid sequence of the PonA protein (SEQ ID NO: 6) was compared to other known proteins reported in GenBank by the BLASTp algorithm (Altschul, S. F. et al., 1997, supra) and aligned by the CLUSTAL W algorithm (Thompson et al., 1994, supra). As shown in FIG. 5, this analysis indicated PonA is most similar to a penicillin-binding protein from *Neisseria flavescens* (Accn. AF087677). PonA shares features characteristic of class A high-molecular-mass PBPs. The sequence including amino acids 124–134 (RQGGSTITQQV) (SEQ ID NO: 103) corresponds to a highly conserved consensus amino acid sequence known as the QGAST (SEQ ID NO: 109) box (Popham et al., 1994, *J. Bacteriol*. 176:7197–7205) found in all class A high-molecular-mass PBPs. Within the C-terminal half of PonA, three regions can be found that are highly conserved in all members of the penicilloyl serine transferase superfamily. These regions include the SXXK (SEQ ID NO: 110) tetrad containing the active site serine at residues 507–510 (SAFK) (SEQ ID NO: 111), the SXN triad at residues 565–567 (SRN), and the KT(S)G (SEQ ID NO: 108) tetrad at residues 688–691 (KTG). These motifs are thought to be brought close together in the folded protein to form the transpeptidase domain active-site pocket that interacts with β-lactam antibiotics.

Similarity of *L. Intracellularis* HtrA Protein to Periplasmic Serine Protease Proteins Examination of the amino terminus of HtrA indicates that amino acids 1–26 are hydrophobic and positively charged which is characteristic of signal sequences (von Heijm, 1985, *J. Mol. Biol*. 184:99–105). The PSORT computer algorithm (Nakai, K., 1991, *PROTEINS: Structure, Function, and Genetics* 11: 95–110), using networks trained on known signal sequences indicates that residues 1–26 likely function as a typical signal sequence and predicts the most likely cleavage site between amino acids 26 and 27. Thus amino acids 1–26 are predicted to be removed from HtrA during the maturation process.

The deduced amino acid sequence of the HtrA protein (SEQ ID NO: 7) was compared to other known proteins reported in GenBank by the BLASTp algorithm (Altschul, S. F et al., 1997, above) and aligned by the CLUSTAL W algorithm (Thompson, J. D. et al., 1994, supra). This analysis indicated HtrA belongs to the large HtrA/DegP family of periplasmic serine proteases. The reported proteins include those identified from *E. coli, Salmonella typhimurium, Camplylbacter jejuni, Haemophilus influenzae, Brucella melitensis, Brucella abortus, Chlamydia trachomatis, Yersinia enterocolitica, Borrelia burgdorfer,* and *Bacillus subtilis,* among others. In some instances the HtrA homolog is referred to as a heat shock protein and has been shown by deletion analysis to be required for bacterial survival at elevated temperatures or for survival of intracellular pathogens. In other cases an HtrA homolog is not induced by temperature but is expressed in response to other physiological stress. Several HtrA homologs have been shown to possess serine protease activity and in a number of cases is important for bacterial virulence and/or intracellular survival, for example resistance to high temperature, hydrogen peroxide, oxidative and osmotic stress.

Alignment of the *L. intracellularis* HtrA protein with its most similar relative from *Pseudomonas aeruginosa* (Accn. #U32853) indicates the two proteins share 40% identical amino acid residues (as shown in FIG. 6). Based on alignment of the *L. intracellularis* HtrA protein with other serine proteases, especially well conserved residues including Histidine-109, Aspartic acid-143, and the active-site Serine-217 are predicted to form the catalytic triad of residues which are highly conserved in bacterial and mammalian serine proteases. A number of HtrA homologs contain a carboxy-terminal RGD motif while others have been shown to contain an RGN motif. The *L. intracellularis* HtrA protein contains a similar motif at residues 458–460 (RNG). The RGD motif has been identified as a cell attachment site for mammalian adhesion proteins (Ruoslahti, E. et al., 1986, *Cell* 44:517–518). The HtrA/DegP family of serine proteases are induced during a range of stress responses and during infection by *L. intracellularis,* surface expression of HtrA may occur as part of a stress response mechanism. Other intracellular heat shock proteins have been shown to become surface expressed under physiological stress conditions and have been implicated as adhesion factors (Ensgraber, M. et al., 1992, *Infect. Immun.* 60:3072–3078 and Hartmann, E. et al., 1997, *Infect. Immun.* 65:1729–1733).

Analysis of the htrA Promoter Region and Induction in Response to Temperature

The gene arrangement for *L. intracellularis* Region A and Region B differ with regard to the extent of intergenic spacing between the encoded proteins. Unlike Region A the ORF's within Region B are more distantly separated. For example, the flgE, ponA, htrA, and hypC genes are separated by approximately 125, 200, and 265 nucleotides between the respective open reading frames. The 200 bp region immediately upstream of htrA was examined in more detail to find a promoter region, particularly since several HtrA protein homologs have been shown to be induced in response to a number of different environmental signals including temperature, oxidative and osmotic stress. Examination of the nucleotide sequence of SEQ ID NO: 2 upstream of htrA indicated a promoter located about nucleotide 2797–2802 (TTGATA; –35 region) and nucleotide 2824–2829 (TATMT; –10 region). These two hexamers are separated by a 21 nucleotide space and share near perfect homology to consensus sigma 70 type promoters. Other promoter elements may exist in this region which control htrA expression in response to various environmental signals. Plasmid pER434, which contains the htrA ORF and htrA promoter region imparts a temperature-dependent phenotype to *E. coli* host cells grown at either 30° C. or 37° C. Thus, the region upstream of htrA can be recognized as a likely functional promoter in response to temperature. It should therefore be possible to use the htrA promoter to operably control expression of heterologous proteins in *E. coli* and other organisms in response to temperature. The presence of other promoter elements that control expression in response to other environmental signals would allow those other signals to be used to control expression.

Example 3

Preparation of Plasmids and Deposit Materials
Plasmids containing DNA fragments encompassing *L. intracellularis* Region A Plasmids were prepared containing the *L. intracellularis* genomic region representing the lysS, ycfW, abc1, and omp100 genes. A 2.6 kb fragment encompassing the lysS gene and a portion of the ycfW gene was amplified using primers ER246 (SEQ ID NO: 97) and ER254 (SEQ ID NO: 98) while a 0.87 kb fragment encompassing a portion of the ycfW gene and complete abc1 gene fragment was amplified using primers ER229 (SEQ ID NO: 73) and ER206 (SEQ ID NO: 66). These fragments were amplified as described in Example 1 under "Specific PCR amplification of subgenomic DNA fragments encompassing *L. intracellularis* Region A". The 2.6 kb and 0.87 kb DNA fragments were isolated by extraction with spin chromatography (QIAquick™) and inserted into the TA cloning site of pCR2.1 Topo. Single sequence extension reactions utilizing vector-specific sequencing primers confirmed the endpoints of the cloned fragments, and revealed that the genes encoding LysS and YcfW in plasmid pT068 and YcfW and ABC1 in plasmid pER438 were in the opposite orientation relative to the lactose promoter.

A 2.97 kb DNA fragment containing the omp100 gene was amplified by PCR employing specific 5' and 3' primers ER187 (SEQ ID NO: 54) and ER170 (SEQ ID NO: 42). PCR reactions were:carried out in triplicate and contained 1 µl DNA extract as template, 1×PCR Buffer II; 1.5 mM $MgCl_2$, 200 µM each deoxy-NTP, 50 pMol each primer, and 2.5 U AmpliTaq Gold thermostable polymerase in a 50 µl final sample volume. Conditions for amplification consisted of denaturation at 95° for 9 min followed by 33 cycles of denaturation (95° 30 sec), annealing (62° 30 sec), and polymerization (72° 3 min). A final extension at 72° for 7 minutes completed the amplification of the target gene region. Following amplification, each of the triplicate samples were pooled and the specific product was isolated by extraction with spin chromatography (QIAquick™) and inserted into the TA cloning site of pCR2.1 Topo in the opposite orientation relative to the lactose promoter. This plasmid construct was designated pER440.

Plasmids pER438 and pER440 were introduced into *E. coli* TOP10 cells (Invitrogen, Carlsbad, Calif.). The resulting strains, designated Pz438 and Pz440, were deposited with the ATCC (10801 University Blvd, Manassas, Va., 20110, USA) on Sep. 9, 1999 and assigned accession numbers PTA-638 and PTA-640 respectively. Plasmid pT068 was introduced into *E. coli* TOP10 cells and the resulting strain was deposited with the ATCC on Jul. 14, 2000 and assigned accession number PTA-2232.

Plasmids Containing DNA Fragments Encompassing *L. Intracellularis* Region B

Plasmids were prepared containing the *L. intracellularis* genomic region representing the ponA, htrA, and hypC genes. The ponA, htrA, and hypC gene fragments were amplified as described above in Example 2, in the section entitled "Specific PCR amplification of subgenomic DNA fragments encompassing *L. intracellularis* Region B" using primers ER228 (SEQ ID NO: 72) and ER190 (SEQ ID NO: 57), which flank the ponA gene; primers ER207 (SEQ ID NO: 67) and RA134 (SEQ ID NO: 78), which flank the htrA gene; and primers ER189 (SEQ ID NO: 56) and ER196 (SEQ ID NO: 62), which flank the hypC gene. The resulting 2.98 kb fragment containing ponA was purified following agarose gel electrophoresis using a JETsorb™ kit and cloned into pCR2.1 Topo to generate plasmid pER432. The resulting 1.72 kb fragment containing htrA was isolated by extraction with spin chromotography (QIAquickTm) and inserted into the TA cloning site of pCR2.1 Topo to generate plasmid pER434. The resulting 0.98 kb fragment containing hypC and additional flanking nucleotides encoding the C-terminal 94 amino acids of ORF1 was isolated by extraction with spin chromotography (QIAquick™) and inserted into the TA cloning site of pCR2.1 Topo to generate plasmid pER436. Single sequence extension reactions utilizing vector-specific sequencing primers confirmed the endpoints of the cloned fragments, and revealed that the genes encoding PonA and HypC were in the opposite orientation relative to the lactose promoter. The HtrA gene was cloned in the same orientation relative to the lactose promoter and cells containing such plasmids exhibited an unstable phenotype at 37° C. which was relieved when growth was maintained at 30° C.

Plasmids pER432, pER434 and pER436 were introduced into *E. coli* TOP10 cells (Invitrogen, Carlsbad, Calif.). The resulting strains, designated Pz432, Pz434, and Pz436 were deposited with the ATCC (10801 University Blvd, Manassas, Va., 20110, USA) on Sep. 9, 1999 and assigned the accession numbers PTA-635, PTA-636, and PTA-637, respectively.

Example 4

Expression of Recombinant HtrA and Omp100 Proteins in *E. Coli*

Plasmid Expression Vectors

The expression vector used for production of recombinant HtrA and Omp100 was pET-28b (+) (Novagen, Inc., Madison, Wis.). The coding sequences for the HtrA and Omp100 proteins were amplified from *L. intracellularis*-infected pig mucosal DNA extract. The PCR products were purified following agarose gel electrophoresis using a JETsorb™ kit and cloned into pCR2.1 Topo to generate plasmids pRL001 (HtrA) and pER415 (Omp100). Specific PCR primers used to amplify the HtrA ORF included ER208 (SEQ ID NO: 68) and RA133 (SEQ ID NO: 77). Primer ER208 was designed to introduce an NdeI site (CATATG) while deleting the HtrA signal sequence. The HtrA insert present in pRL001 was subcloned into pET-28b (+) following digestion with NdeI and EcoRI. The resulting expression plasmid, designated pER405, was sequenced at both 5' and 3' ends of the inserted fragment and confirmed to encode an in-frame fusion with the vector encoded 6×His leader. Therefore the predicted amino terminal sequence of the encoded protein consisted of the sequence MGSSHHHHHHSSGLVPRGSHM (SEQ ID NO: 104) encoded by the vector followed immediately by the sequence ALPNFVP (SEQ ID NO: 112) beginning at Alanine-27 of the HtrA open reading frame.

Specific PCR primers used to amplify the Omp100 ORF included ER216 (SEQ ID NO: 70) and RA138 (SEQ ID NO: 79). Primer ER216 was designed to introduce an NcoI site (CCATGG) while deleting the Omp100 signal sequence. In addition, ER216 specified a leader peptide, termed a "protective peptide" which protects recombinant proteins from proteolytic degradation, based on information from Sung et al., 1986, Proc. Natl. Acad. Sci. USA 83:561–565; Sung et al., 1987, Meth. Enzymol. 153:385–389; and U.S. Pat. No. 5,460,954, which references are incorporated herein by reference. The protective peptide consisting of the amino acid sequence MGTTTTTTSL (SEQ ID NO: 105) was encoded by the 5' proximal nucleotide sequence of ER216. The Omp100 insert present in pER415 was subcloned into pET-28b (+) following digestion with NcoI and EcoRI. The resulting expression plasmid, designated pRL029, was sequenced at both 5' and 3' ends of the inserted fragment and confirmed to encode an in-frame fusion with the protective peptide leader. Therefore the predicted amino terminal sequence of the encoded protein consisted of the sequence MGTTTTTTSL (SEQ ID NO: 105) specified by the 5' proximal nucleotide sequence of ER216 followed immediately by the sequence ASKDDPSIV (SEQ ID NO: 106) beginning at Alanine-26 of the Omp100 open reading frame.

Expression of Recombinant Proteins

The pET-28b (+) based expression vectors pER405 and pRL029, encoding recombinant HtrA and Omp100, respectively, were introduced into the expression host *E. coli* BL21 (DE3). This expression host has the genotype $F^-$, ompT hsd$S_B$ ($r_a^-m_B^-$) gal dcm (DE3) (Novagen, Inc.) which allows high level transcription of cloned genes driven by the IPTG-inducible phage T7 promoter. The *E. coli* transformants were propagated in SB#2 medium (2.4% yeast extract, 1.2% tryptone, 0.5% $K_2HPO_4$, 0.25% $KH_2PO_4$, 0.014% $MgSO_4$) containing. 50 μg/ml kanamycin sulfate in a 5 L BioFlow™ 3000 fermentor (New Brunswick Scientific, Edison, N.J.) at 30–37 ° C. until $A_{625}$ was 2.5–30.1. Recombinant protein expression was obtained following induction with 1 mM IPTG for 1–4.5 h.

Wet cells of *E. coli* expressing recombinant HtrA were lysed by homogenization at 10,000 psi (2 passes) followed by centrifugation. The pellet, which contained HtrA, was washed with 2×RIPA/TET which was in a 5:4 ratio. 2×RIPA is 20 mM Tris (pH 7.4), 0.3 M NaCl, 2.0% sodium deoxycholate, and 2% (v/v) Igepal CA-630™ (Sigma). TET is 0.1 M Tris (pH 8.0), 50 mM EDTA, and 2% (v/v) Triton X-100. The washed pellet was then solubilized in 8 M Urea, 10 mM Tris, 0.1 M $NaH_2PO_4$, pH 7.0. The solubilized protein was diluted 2 fold in 8 M Urea, 10 mM Tris, 0.1 M $NaH_2PO_4$, pH 7.0 and applied onto a Ni NTA column (QIAGEN, Santa Clarita, Calif.). The desired protein was eluted off this column by reduction of pH into 8 M Urea, 10 mM Tris, 0.1 M $NaH_2PO_4$, pH 4.5. The final pooled fractions were dialyzed against 4 M Guanidine HCl, 50 mM Tris, pH 6.5 and then step dialyzed to 2 M Guanidine HCl, 25 mM Tris, pH 6.5. The final product was filtered by 0.22 μM filtration. The protein concentration was 0.56 mg/ml with an estimated visual purity of 70% by SDS-PAGE.

Wet cells of *E. coli* expressing recombinant Omp100 were lysed with lysozyme and sonication in the presence of Benzonase™ (Benzonase™ (EM Industries Inc, Hawthorne, N.Y.)), to facilitate DNA degradation, followed by centrifugation. The pellet, which contained Omp100, was washed twice with 2 M Urea, 50 mM Tris, 10 mM EDTA, 25 mM DTT, 1% Zwittergent 3–14. The pellet was resuspended with 6 M Urea, 50 mM Tris (pH 8.0) followed by centrifugation. The pellet was washed with 2×RIPA/TET which was in a 5:4 ratio and the washed pellet was then solubilized in 8 M Urea, 50 mM Tris (pH 8.0). 25 mM DTT was added to the solubilized protein and further diluted 2:1 with 8 M Urea, 25 mM DTT, 50 mM Tris (pH 8.0). The diluted solubilized protein was applied onto a Q-Sepharose column equilibrated with 8 M Urea, 25 mM DTT, 50 mM Tris (pH 8.0). Recombinant Omp100 was eluted in a linear gradient of 0–1 M NaCl in 8 M Urea, 25 mM DTT, 50 mM Tris (pH 8.0). The pooled fractions were dialyzed against 6 M Guanidine HCl, 10 mM DTT, 50 mM Tris (pH 8.0) and then step dialyzed to 4 M Guanidine HCl, 6.7 mM DTT, 33.3 mM Tris (pH 8.0). The final product was filtered by 0.22 μM filtration and frozen at 70° C. The purified Omp100 protein was then thawed and centrifuged (16,000 rpm, 60 min) and the supernatant was subjected to 0.22 μM filtration again to remove insoluble particles and aggregates. The protein concentration was 1.08 mg/ml with an estimated visual purity of 80% by SDS-PAGE.

What is claimed is:

1. An isolated polypeptide corresponding to SEQ ID NO: 5 that encodes an *L. intracellularis* Omp100 protein.

2. An isolated polypeptide selected from the group consisting of *L. intracellularis* Omp100 protein corresponding to SEQ ID NO: 5; and a fusion polypeptide encoding the *L. intracellularis* Omp100 protein corresponding to SEQ ID NO: 5 fused to another protein or polypeptide.

3. A substantially pure polypeptide comprising an epitope of an Omp100 protein corresponding to SEQ ID NO: 5 that is specifically reactive with anti-Lawsonia antibodies.

4. An isolated polypeptide comprising an amino acid sequence for an *L. intracellularis* Omp100 protein corresponding to SEQ ID NO: 5.

5. An immunogenic composition comprising a polypeptide of claim 2 in combination with a pharmaceutically acceptable carrier.

* * * * *

SEQUENCE LISTING

<160> NUMBER OF SEQ ID NOS: 112

<210> SEQ ID NO 1
<211> LENGTH: 6617
<212> TYPE: DNA
<213> ORGANISM: Lawsonia intracellularis

<400> SEQUENCE: 1

```
ggggaacgct acttaactta agttggtgtt tatctaaaca aaaccataca gtcaagcttt       60
ttatttttca agactcattt tatcttcttg actatcaagc tcttttggac taccgctaat      120
taaatataga atacgcctta attgtattac tggagaagca ttcattgata cagaaaaaaa      180
aatctcatcc cccaattaaa ttagctacca agtcacctca tgtatcttat tttaaacctc      240
tgcttgagag ccttgcagaa aaaaatgagc ttaatgaagt tatcaaaaac tgtgtagtaa      300
aatcctgtga gcttttagac tcaggaattc ctctctaccc agatgagttc gttaaagagc      360
attatgctgg tatgcttcgt gctgaatatg aagcctatag tgcatctgaa cttgaatcac      420
tagacgaaat ttttgcttgt gctggacgta ttatctctct ccggtcattt ggtaaagtaa      480
tattctttca tatcatggat agaagcggtc gcattcaatg ttatgcatct cgtgaaaata      540
tgggagaaga agcatttagt acattcaaaa agtttgtatt tggtgacatt gttggtgtta      600
atggaaaact tttccgtaca aaaatgggag aattaactct caactgctcc actatcacat      660
tattagctaa gtccttccgt tctttaccag aaaaacataa tggccttact aacatagaac      720
ttaggtatcg ccagcgatat atagatctta ttgttaatcc taaaacaaga gatatcttta      780
gaaagcgtag taaaattatt catgaaatta gagcattctt agaagaaaat ggctttatag      840
aagtagaaac acctattctt caacctattc caggtggtgc aatggcgcgt ccatttacta      900
cacataataa tgcaatggat atgacccttt atatgcgcat tgctcctgaa ctctatttaa      960
agcggcttct tgttggtggt tttgaaaaac tatttgaatt aaatcgtagc ttccgtaatg     1020
aaggaatctc tatccaacat aatccagaat ttaccatgtg tgaattttac tgggcctatg     1080
caacatatct agatcttatg gaacttacag aagaaatgtt tgcatacctt acaaaaaaaa     1140
tctgtggtac tatgactata tcttaccaag gaaatacaat cgattttaca cctgggacat     1200
ggcaaaaata tacatttcat gagtctcttg aaaaaattgg tgggcattct ccagagtttt     1260
ataataactt tgaaaaagtt agtgaatata ttaaagaaca tggagaaaaa gttctgacaa     1320
ctgacaaaat aggaaaactt caagctaaac tctttgacct tgacgtagaa aacaaactga     1380
ttcaacccac atttatctat cactatccta ctgatatctc tccactctcc aaaaaaaata     1440
aagataaccc agaagtaaca gatcgttttg agcttttttat tgcaggaaaa gaaattgcta     1500
atgcattttc agaacttaat gatcctattg atcaacgtct gcgttttgaa gaacaagttc     1560
ttgagaaagc acgtggagac gaagaagcat gtcccatgga tgaagattat cttcgtgcat     1620
tagaatatgg aatgccacca gcagcagggg aaggtattgg aattgatcga ctcgttatgc     1680
ttcttacaga ctctccttcc atacgagagg ttatccttttt ccctctatta cgaacagaac     1740
```

```
gctaatgaag tttgaactttt ttattgctct acattatctc tttgcaagac gaaaacaagc    1800
tttcatttat cttatttcat taatgtcaat tttaggagtt gctattggtg ttgcctctct    1860
tgtagttgta ttaggggttt ataatgggtt tactatagat atccgtgaca aaattcttgg    1920
agctaatgca catattatta ttacaggaaa ctttgattca cctatagaag aacctacaag    1980
ttttactcag ctgtcaacta cttctatgct gtcccaaaat gctcttatta tcctaaataa    2040
acttcaacaa acttctgcga taataggtgc tactcccttt atttatgcag aatgtatgat    2100
atcctctcct catggagtaa aaggtcttat tttaaggggg atagatccct catcagcaca    2160
aaatgtcatt tctatgcttt ctcatctaac aaaaggaaat cttgaagatc ttatccctaa    2220
agttttaggg actccagacg gtattattat tggtaatgag cttgcccaaa gactcaatgt    2280
aacaataggt agtcgtgtaa acttactctc accaacagga caaaaaacat cttcaggatt    2340
tcagccacgg atacgaccac ttattgtaac aggaatcttt catacaggta tgtttgaata    2400
tgacacttct cttgcatttta cttctcttaa tgcagcaaga aacttcttg gactacctca     2460 caattatatt tctggaatag aagtcagtat tcatgatgtg tatcaagcaa attatatcac    2520
aaaccaactg caacaagagt taggtcataa ttttttctgta cgaagctgga tggatatgaa    2580
tgcaaattta tttgcagcac ttaagcttga aaaaattgga atgtttatta tattagctat    2640
ggttgttctc attggttctt tttctattgt tacaacatta attatgcttg taatggaaaa    2700
aacaagagat attgctattc taacctccat gggggctaca agccaaatga tccgtcgtat    2760
tttcatttta caaggaacta ttattggtat tgtaggaact ttgctaggtt atctacttgg    2820
aattactctt gcacttttat tgcagaaata tcaattcatt aaacttcccc ctggggtata    2880
tacaatagat cacttgccag tattacttaa ttggctagat atattcatta ttggtacttc    2940
tgccatgcta ctatgttttt ttgctactct ctaccctgcc catcaagcgg ctcgactaca    3000
gcctattgaa ggattaaggt acgagtaaaa atgtcacaat atcattaga aaatatagta    3060 aaacagtatg acagtccttc tgaacctatt tgtgtcttac ataaaataaa tctttctata    3120
gctcacggag aatcattagc tattattggt gcatctggtt ctgggaaatc aaccctattg    3180
catatccttg gagcattaga tataccatct tctggcactg tgttatttaa taataaaaat    3240
ttaagtcata tgggcccaaa tgaaaaagca tgctttcgta ataaactact gggatttatt    3300
ttccaatttc acaacttact tccagaattc tctgctgaag aaaatgttgc aatgaaagct    3360
cttattgctg gtataccaaa aaagaaagct cttctgcttg cacgagaagc acttggtagt    3420
gtaggacttg aaaataaata ccatcacaga ataacaatgt tgtcaggagg tgaacgtcaa    3480
cgtgtagcca tagctagagc tattttatta gaaccccaag ttcttcttgc agatgaacca    3540
acaggcaacc ttgatcaaaa aacaggtgaa cacattgcca atcttctaat ctcacttaat    3600
aaaactttta atataactct tattgtagtc acacataata atgatattgc ccattctatg    3660
ggacgctgcc ttgagctgaa gtccggagat ctacatgaca aaacgcctga atatatttct    3720
tctactgtta ctgtgtaata tactttattg taatataata gccaatgctg cttcaaaaga    3780
cgatccttct attgtggttc tcccatttca aattaatggc tcatcaaatg atgaagagtt    3840
acaaacagaa ctaccaatgc ttcttgcaac tgcattaaag aataagggat tcgtgtcat    3900 ccctaataaa tctgcattaa atcttctata aaacaaaat atctcccaac ttaatatttc    3960
tactgcaaaa aaggtagctc aacaactcca tgctgactat gtagtatacg gcagtttcaa    4020
tcaaacaggt gaaaatttta gtattgatag taggcttatt gatagtacag gtgtagcatc    4080
```

```
tgcacgtcca ttatacatag aaaaaccaaa atttaatgag ctaaatattg ctgtaacaga      4140
acttgctgaa cgtataagta atggcattat aaagaaaaac actattgctg atgtacgtat      4200
tcatgggctt aaagttcttg atcctgatgt aatccttaca cgactcacta ttaataaggg      4260
agatcatact gatcatgcca aaattaatgc agaaatcaaa aaaatatggg aattaggata      4320
ttttagtgat gtctctgcaa gtattgaaga agcggggaa ggacgattac ttgtatttac       4380
tgtacaagaa aagcctaaaa ttacagatgt tgttgttcaa ggctcaaaag ctgtaagtat      4440
cgataacatt cttgctgcaa tgagttctaa aaaaggatca gttattagtg atagactatt      4500
gtcccaagat attcaaaaaa ttaccgacct ctatagaaaa gaaggctact atctcgctga      4560
agttaattat gaaataaaag agaaagaaaa tacttcttct gcaacactat tgttaacagt      4620
aaatgaaggg aaaaaacttt atattaaaga tgtccgaatt gaaggacttg aaacaataaa      4680
agctaaaact ttaaaaaaag agttagcatt aacagaacgt aatttttat catggtttac       4740 tggaacaggt gtattacgtg aagaatatct tgaacgtgac tctatagcaa tctctgccta      4800
tgccatgaat catggctatg tagatattca agttgcttca cctgaagtaa cattcaatga      4860
aaaaggaatt gttattacat ttagagtaaa agaaggtaag cgctataaaa taggaaaaat      4920
agactttaaa ggagatctta ttgagacaaa tgaacaactc cttaaagtaa caaaaattga      4980
tgatcataaa aactatgagc agtattttc tctttctgtt atgcaagatg atgtaaaagc       5040
attaacagat ttattcag attatggtta tgcatttgct gaagtagatc ttgaaacaac        5100
caaaaatgaa gaagatgcaa caattgatgt tactttcctt attgataaaa aacaaaaagt      5160
ctttcttcgt agaataattg ttgaaggaaa tactcgtact agagataatg ttatcctccg      5220
tgaattacgc cttgctgatg gagatctttt taatggtcaa catctccgac gctctaatga      5280
atgccttaac cgccttggct attttaacca agtagataca gatacactgc ctacagggaa      5340
agatgatgaa gttgatctac ttgtaaaagt tcaagaagct cgaacaggtg caatcacagg      5400
tggtgttggt tactcaacac attctaaatt tggtgtttca ggaagtatct cagaaagaaa      5460
cttatgggga aaaggttata ttttaagtat tgaaggtttt atttctagta agtcatcttc      5520
tcttgatctt tctttacca atcctcgtgt ttatgataca gactttggct ttagtaataa       5580
catttatacg ctacgagatg aatgggatga cttccgtaaa aaaacttatg gagataccat      5640
acgtctattt caccctatag gagaatattc atctatcttt gttggctatc gaattgatca      5700
atatcgtcta tatgatattc catctacagc accacgctct tatcttgact atcaagggaa      5760
aaatatttct agtgtagtaa gtggtggttt tactttgat tctacagaca gtcgtgagag       5820
accatctaaa gggcatattg caaaactaat tgttgaatat ggaggtggtg gtcttggtgg      5880
taatgataac ttcttcaagc caattgctga actacaagga ttttactcaa tttcaagaag      5940
taaaaaccat ataatacatt ggcgtacacg tgcaggtgca gcttataaga atagtaaaaa      6000
acctgtgcca gtatttgacc gatttttttat tggtggtata gatagtatta gaggatatga     6060
tacagaagat cttgcaccaa agatcctcg ctttggagat gaaattggtg gtgataggat       6120
ggcttttctt aacctagagt atatttggac attccagcca gagctaggtc ttgcattagt      6180
tccattctat gacataggat tccaaacaga ttctgtacaa acttctaacc cattctctaa      6240
actcaaacaa tcatatggcc ttgaacttcg ctggcgttca ccaatgggag atttgcgatt      6300
tgcctatggt ataccactca ataaaaatgt tagtggcaaa aaactcgtg gtagatttga      6360 attttcaatg gggcaattct tctaataaca taatataact cataaaataa gagatactat      6420
aaatttaaag atgagaggtg cagggagccg ccccataaaa atgttgttat gccataacta      6480
```

```
ctgcactagg aaatagatga atataacata ttctcttcaa tgcaagcatg agcaacatca    6540
tttgtcgaca agccattgca attttatcca attatattta ttggaaaaaa ctgttatgga    6600
tacctatcct agcttac                                                   6617

<210> SEQ ID NO 2
<211> LENGTH: 5445
<212> TYPE: DNA
<213> ORGANISM: Lawsonia intracellularis

<400> SEQUENCE: 2
ctaacgtaga catgagcaga gaaatggtta atatgattat tattcaacgt ggttttcaga      60
tgaatagtaa atctgttaca acagcagaca caatgctaca aaaagcactt gaactaaagc     120
gttaatatgt attttattgt taattttgta ttttttaatc tattgtaatc ttagtatgta     180
ttatatatta atagtatttc aacttataat tatttatttt gatatgttac tacttttttct    240 ttacgtcaag gatgaaacag gttatcagct ttgacatgaa aaagttttt ctgaatattg     300 ttatttttg ttttggtatt attttactat ctattatagg actaataggt ctttattttt     360
gggttagtag agatcttcct aatattacaa agcttaatga ctatagacca gctttagtaa     420
caacagttct tgctagagat ggaacactta ttgggtatat atcgagag aagcgttttc      480 ttatcccatt aagcgaaatg tctccttttt tgcctaaggc attttagct gcagaagatg      540 ctgagtttta tgaacatgaa ggtgttaatc cgcttgctat tatccgggct tttttaataa    600
atcttcaatc agggacaaca cgccaaggtg gaagtacgat tactcaacaa gtcattaaac    660
gtcttttgtt aagccctgaa agaagttatg agcgtaagat aaaagaggca attcttgcct    720
accgtctaga gaaatatctt tctaaagatg aaatttttaac tatatactta aatcagacat    780
ttttaggtgc tcattcttat ggggttgagg cagccgcaag gacttatttt gctaagcatg    840
ctaaagatct ttcattagct gaatgtgctc ttcttgcagg acttccacaa gcaccttctc    900
ggtataatcc ctataaagat cctgaggctg caaaaattag acaacgttat gctcttcgta    960
ggctacatga tgttggttgg attacccagg ctgaatatga ggaggctctt caagaaccac   1020 tatattttc ttcaatgaaa gaagggttag gagctgaatc aagttggtat atggaagaag    1080
tccgtaagca gcttgtttcc tttcttagta agaaaatat ttctcagtat ggaattgtgc     1140
tccctttata tggagaagat gcactttatg aacttgggtt tactatccag acagcaatgg    1200
atcctcaggc acaacttgtg gcatatgatg ttttaagaaa tggacttgaa aattttagta    1260
aacgacaagg ttggaaagga cctattgagc acatttcttc aacaatgatt cagcattacc    1320
tagaaaatgc tacatttaca cctgaaaaac ttgatggtgg tgcatgggct aaagcaattg    1380
ttagtaaagt tagtcaagaa ggtgcagaag tattccttag tagcatttat aaagggtttg    1440
ttagtgtaga gactatgggt tgggcacgta aacctaatcc agaagttcga tcagcttatt    1500
gtgctcctat caaagatgca cgtagtgttt taaatcctgg agatattata tgggtatctg    1560
gagttggccc agactctaca cataggtata gttctaaaac actagatact tctaaaccta   1620
ttcctttagc tcttcaacag ttaccacaaa tccaaggagc attaatttct atagagccaa    1680
atacaggcga tgtgatagct atgattgtg gttatgagtt tggaaagagc caatttaata    1740
gagctgtaca ggcaatgagg caaccaggtt ctgcatttaa gccaattgta tactctgcag    1800
cacttgatca tgattataca tctgcaacta tggtgcttga tgcacctata gtagaattta    1860
tggaaagtgg ggatatttgg agaccaggta attacgaaaa aaatttttaaa ggaccaatgt    1920
```

```
tatttagcaa tgctcttgca ctttcaagaa atttatgtac agtaagaatt gcacagtcta    1980
taggattacc tgctgttatt gaaagagcta aggctttagg atttaatggt aatttccctg    2040
aatttttttc tattagttta ggtgcagttg aagtaactcc tattcgtctt gtaaatgcct    2100
atacagcatt tgcaaatggt ggtaacttag ccacgccacg gtttattctt tctattaaag    2160
attctaataa tactgttatt taccgccagg aaatagaaca acatcctgtt atttcaccac    2220
agaatgcgta tattatggct tcactattaa aaatgttgt taatattggt acagcaagaa     2280
aagcaaaagt acttgagcgt cctctagcag gaaagacagg aactacaaat ggggagcatg    2340
atgcatggtt tattggattt acaccctatc ttgttacagg tgtttatgtt ggtaatgatc    2400
atccacagac attaggtaaa gatggcacag gtgctgttgc tgctcttcct atttttacag    2460
aatattcaaa agtagtattg aaaaaatatc ctgaaagtga cttcctgtt cctgatggga     2520
ttacttttgc ttcaatagat actcagacag ggaatagagc aactgctaat agtaccaata    2580
gtgttgtatt accttttat gtaggtacag ttccagaata ttttgatagt aaagataatg     2640
aggtgaatac tattgaacgt ggtgaggatt tattaaaaca attttttta ccatttttat      2700
gtagctgatt ataaaaatgg agtttgttac atatttttg ttatcattat cataagttat      2760
atttatatac tcaaatattg aggcaagtta gtatccttga taatatttca taagagctag    2820
atttataata tacgtttatc ttattttta tccctaatta ttcaaggttg atagttttaa      2880
ggagagttat atgttttgta agttaaaggt gataatatgc ataactctta tgtttattat    2940
aactgtggtt ccaacaattg cagaaagtgc cttaccaaac tttgtacccc ttgtaaaaga    3000
tgctagtaaa gctgttgtca atattagtac agaaaaaaaa attcctcgtg gtcgtacaga    3060
gttccctatg gaaatgtttc gtggtcttcc cccaggtttt gaacgctttt ttgaacaatt    3120
tgaacctaaa gggcctgata gtcagataca taaacaacgt tcattaggaa ctggttttat    3180
catttcttca gatggatata ttgttaccaa taatcatgtg atagaaggag cagattctgt    3240
tagagtaaat cttgaaggta cctcaggcaa agaagaatca ctacctgcag aagtgatagg    3300
tagagatgaa gaaacagatc ttgctttatt aaaagttaaa agtaaagact cattacctta    3360
tcttatatt ggaaattcag atactatgga agttggtgaa tgggtgctag ctattggtaa     3420
tccttttggg ttaggccata cagttacagc aggtatatta agtgctaaag acgtgatat      3480
tcatgctgga ccatttgata actttttaca aactgatgca tctatcaatc tgggaatag     3540
tggtggtcca ttaatcaata tgtcaggaca agttgtaggc attaacacag ctattatggc    3600
aagtgggcaa ggtattggtt tcgctatccc aagtagtatg gcagatcgta ttatagagca    3660
gttaaagaca aataaaaagg taagtagagg ttggataggt gtaacaattc aggatgtaga    3720
tactaataca gctaaagctc ttggattatc tcaggcaaaa ggtgcgcttg taggttctgt    3780
tgttcctgga gatcctgctg ataaggctgg tcttaaagtt ggcgatattg taacacaagc    3840
tgatggtaaa caaattgata gtgcaagctc attgttaaaa gctattgcta ctaaacctcc    3900
tttttctgtt gtgaaattaa agtttggccg tgatggaaag agtaaagata tatccattac    3960
actaggagag cgtaagacaa cttcaagtca aaaacaaagc tcaccagaat ctttaccagg    4020
tgctcttgga ttatctgtac gtcctttaac acaagaagta tctaaatctt ttgatgttaa    4080
gcttggtata ggcttgttag ttgtaagcgt tgagcctaat aagccagcgt cagaagctgg    4140
tatcagagag caagatataa tcctttctgc taacttaaaa cctcttcaat cggctgatga    4200
ccttgcaaat attatttgtg gagatgctaa gaagaaaggg gttattatgt tacaattaca    4260
aagaaatgga caaacgtttt ttaaaacatt gtctttaact gaagatagca actaactctt    4320
```

-continued

```
ccttatttat taaacttata acaagtataa agaatactct ttacttttgt aaggagtatt   4380 ctttttttata gtttgagctt gttagaggta tattaatact atttttatct atcaatttta   4440
taaataatat gttaggatat aagaaaagga taaaatgatt ttcatagata tagttattgt   4500
attccatata gttactaatt attatgtgat acaagagggt aaaagtttgt ttaaaataat   4560
atagaataaa ggataagttg atgtgtcatg ctatccctgt aaaagttatt gaactgttgg   4620
ataatgatat tattcgtgct acggttggcg atagtacaac aatattgact gtttcaggta   4680
tgttacttcc agaaccagta actgttggag attatattat tgtgcatgct ggatttgcta   4740
tacataaact ggaggcaact gaagctgaag aaagtttacg gttattcaga gagctttcta   4800
ttgccgttgg tgatacacct aatttttaat tattaatcta attaatagat aaagtagtta   4860
gatacagtaa aagaaaaata ctagataggt gcaatgaatt tttagttatt attatttgtt   4920
agttctatta tgttgaatag tgcttgttgc ttcaggactt aatgcattat atacatttac   4980
tgcttgttct tttgctttga gaagtaaagg agtcagtgtg ggctttgggc gtttttcaat   5040
acgcattcca acgtatgtcc ctataggaaa agaaagaata atacggttaa gtttagacca   5100
tgaagaggtt acatcccaag tacgcttagg acctagtaaa gtagagcgac aataaattct   5160
acattcagga taaagctgct ttgttagacg aataagttgc caaggactca cccattgact   5220
gtcttttttt ggttttttat gaagcagctg taatgtacta ttaatgatat gatttataga   5280
ccatttattt gtgaatccaa caataatacc atcagatgca acacgaaatg cttctgctaa   5340 aattttttt ggatcttcaa catattctaa aatagtcact aatgatgcgt agttaaaact   5400
ttcatcttca aatggaagat catctaaggc acctaattgg aattc                  5445
```

<210> SEQ ID NO 3
<211> LENGTH: 427
<212> TYPE: PRT
<213> ORGANISM: Lawsonia intracellularis

<400> SEQUENCE: 3

```
Met Lys Phe Glu Leu Phe Ile Ala Leu His Tyr Leu Phe Ala Arg Arg
1               5                   10                  15

Lys Gln Ala Phe Ile Tyr Leu Ile Ser Leu Met Ser Ile Leu Gly Val
            20                  25                  30

Ala Ile Gly Val Ala Ser Leu Val Val Val Leu Gly Val Tyr Asn Gly
        35                  40                  45

Phe Thr Ile Asp Ile Arg Asp Lys Ile Leu Gly Ala Asn Ala His Ile
    50                  55                  60

Ile Ile Thr Gly Asn Phe Asp Ser Pro Ile Glu Glu Pro Thr Ser Phe
65                  70                  75                  80

Thr Gln Leu Ser Thr Thr Ser Met Leu Ser Gln Asn Ala Leu Ile Ile
                85                  90                  95

Leu Asn Lys Leu Gln Gln Thr Ser Ala Ile Ile Gly Ala Thr Pro Phe
            100                 105                 110

Ile Tyr Ala Glu Cys Met Ile Ser Ser Pro His Gly Val Lys Gly Leu
        115                 120                 125

Ile Leu Arg Gly Ile Asp Pro Ser Ser Ala Gln Asn Val Ile Ser Met
    130                 135                 140

Leu Ser His Leu Thr Lys Gly Asn Leu Glu Asp Leu Ile Pro Lys Val
145                 150                 155                 160

Leu Gly Thr Pro Asp Gly Ile Ile Ile Gly Asn Glu Leu Ala Gln Arg
                165                 170                 175
```

-continued

```
Leu Asn Val Thr Ile Gly Ser Arg Val Asn Leu Leu Ser Pro Thr Gly
            180                 185                 190

Gln Lys Thr Ser Ser Gly Phe Gln Pro Arg Ile Arg Pro Leu Ile Val
        195                 200                 205

Thr Gly Ile Phe His Thr Gly Met Phe Glu Tyr Asp Thr Ser Leu Ala
    210                 215                 220

Phe Thr Ser Leu Asn Ala Ala Arg Glu Leu Leu Gly Leu Pro His Asn
225                 230                 235                 240

Tyr Ile Ser Gly Ile Glu Val Ser Ile His Asp Val Tyr Gln Ala Asn
                245                 250                 255

Tyr Ile Thr Asn Gln Leu Gln Gln Glu Leu Gly His Asn Phe Ser Val
            260                 265                 270

Arg Ser Trp Met Asp Met Asn Ala Asn Leu Phe Ala Ala Leu Lys Leu
        275                 280                 285

Glu Lys Ile Gly Met Phe Ile Ile Leu Ala Met Val Val Leu Ile Gly
    290                 295                 300

Ser Phe Ser Ile Val Thr Thr Leu Ile Met Leu Val Met Glu Lys Thr
305                 310                 315                 320

Arg Asp Ile Ala Ile Leu Thr Ser Met Gly Ala Thr Ser Gln Met Ile
                325                 330                 335

Arg Arg Ile Phe Ile Leu Gln Gly Thr Ile Gly Ile Val Gly Thr
            340                 345                 350

Leu Leu Gly Tyr Leu Leu Gly Ile Thr Leu Ala Leu Leu Gln Lys
        355                 360                 365

Tyr Gln Phe Ile Lys Leu Pro Pro Gly Val Tyr Thr Ile Asp His Leu
    370                 375                 380

Pro Val Leu Leu Asn Trp Leu Asp Ile Phe Ile Ile Gly Thr Ser Ala
385                 390                 395                 400

Met Leu Leu Cys Phe Phe Ala Thr Leu Tyr Pro Ala His Gln Ala Ala
                405                 410                 415

Arg Leu Gln Pro Ile Glu Gly Leu Arg Tyr Glu
            420                 425

<210> SEQ ID NO 4
<211> LENGTH: 235
<212> TYPE: PRT
<213> ORGANISM: Lawsonia intracellularis

<400> SEQUENCE: 4

Met Ser Gln Tyr Leu Leu Glu Asn Ile Val Lys Gln Tyr Asp Ser Pro
1               5                   10                  15

Ser Glu Pro Ile Cys Val Leu His Lys Ile Asn Leu Ser Ile Ala His
            20                  25                  30

Gly Glu Ser Leu Ala Ile Ile Gly Ala Ser Gly Ser Gly Lys Ser Thr
        35                  40                  45

Leu Leu His Ile Leu Gly Ala Leu Asp Ile Pro Ser Ser Gly Thr Val
    50                  55                  60

Leu Phe Asn Asn Lys Asn Leu Ser His Met Gly Pro Asn Glu Lys Ala
65                  70                  75                  80

Cys Phe Arg Asn Lys Leu Leu Gly Phe Ile Phe Gln Phe His Asn Leu
                85                  90                  95

Leu Pro Glu Phe Ser Ala Glu Glu Asn Val Ala Met Lys Ala Leu Ile
            100                 105                 110

Ala Gly Ile Pro Lys Lys Lys Ala Leu Leu Leu Ala Arg Glu Ala Leu
```

-continued

```
        115                 120                 125

Gly Ser Val Gly Leu Glu Asn Lys Tyr His His Arg Ile Thr Met Leu
    130                 135                 140

Ser Gly Gly Glu Arg Gln Arg Val Ala Ile Ala Arg Ala Ile Leu Leu
145                 150                 155                 160

Glu Pro Gln Val Leu Leu Ala Asp Glu Pro Thr Gly Asn Leu Asp Gln
                165                 170                 175

Lys Thr Gly Glu His Ile Ala Asn Leu Leu Ile Ser Leu Asn Lys Thr
            180                 185                 190

Phe Asn Ile Thr Leu Ile Val Val Thr His Asn Asn Asp Ile Ala His
        195                 200                 205

Ser Met Gly Arg Cys Leu Glu Leu Lys Ser Gly Asp Leu His Asp Lys
    210                 215                 220

Thr Pro Glu Tyr Ile Ser Ser Thr Val Thr Val
225                 230                 235

<210> SEQ ID NO 5
<211> LENGTH: 896
<212> TYPE: PRT
<213> ORGANISM: Lawsonia intracellularis

<400> SEQUENCE: 5

Met Thr Lys Arg Leu Asn Ile Phe Leu Leu Leu Leu Leu Cys Asn Ile
1               5                   10                  15

Leu Tyr Cys Asn Ile Ile Ala Asn Ala Ala Ser Lys Asp Asp Pro Ser
            20                  25                  30

Ile Val Val Leu Pro Phe Gln Ile Asn Gly Ser Ser Asn Asp Glu Glu
        35                  40                  45

Leu Gln Thr Glu Leu Pro Met Leu Leu Ala Thr Ala Leu Lys Asn Lys
    50                  55                  60

Gly Phe Arg Val Ile Pro Asn Lys Ser Ala Leu Asn Leu Leu Tyr Lys
65                  70                  75                  80

Gln Asn Ile Ser Gln Leu Asn Ile Ser Thr Ala Lys Lys Val Ala Gln
                85                  90                  95

Gln Leu His Ala Asp Tyr Val Val Tyr Gly Ser Phe Asn Gln Thr Gly
            100                 105                 110

Glu Asn Phe Ser Ile Asp Ser Arg Leu Ile Asp Ser Thr Gly Val Ala
        115                 120                 125

Ser Ala Arg Pro Leu Tyr Ile Glu Lys Pro Lys Phe Asn Glu Leu Asn
    130                 135                 140

Ile Ala Val Thr Glu Leu Ala Glu Arg Ile Ser Asn Gly Leu Ile Lys
145                 150                 155                 160

Lys Asn Thr Ile Ala Asp Val Arg Ile His Gly Leu Lys Val Leu Asp
                165                 170                 175

Pro Asp Val Ile Leu Thr Arg Leu Thr Ile Asn Lys Gly Asp His Thr
            180                 185                 190

Asp His Ala Lys Ile Asn Ala Glu Ile Lys Lys Ile Trp Glu Leu Gly
        195                 200                 205

Tyr Phe Ser Asp Val Ser Ala Ser Ile Glu Glu Ser Gly Glu Gly Arg
    210                 215                 220

Leu Leu Val Phe Thr Val Gln Glu Lys Pro Lys Ile Thr Asp Val Val
225                 230                 235                 240

Val Gln Gly Ser Lys Ala Val Ser Ile Asp Asn Ile Leu Ala Ala Met
                245                 250                 255
```

-continued

Ser Ser Lys Lys Gly Ser Val Ile Ser Asp Arg Leu Leu Ser Gln Asp
        260                 265                 270

Ile Gln Lys Ile Thr Asp Leu Tyr Arg Lys Glu Gly Tyr Tyr Leu Ala
        275                 280                 285

Glu Val Asn Tyr Glu Ile Lys Glu Lys Glu Asn Thr Ser Ser Ala Thr
        290                 295                 300

Leu Leu Leu Thr Val Asn Glu Gly Lys Lys Leu Tyr Ile Lys Asp Val
305                 310                 315                 320

Arg Ile Glu Gly Leu Glu Thr Ile Lys Ala Lys Thr Leu Lys Lys Glu
                325                 330                 335

Leu Ala Leu Thr Glu Arg Asn Phe Leu Ser Trp Phe Thr Gly Thr Gly
                340                 345                 350

Val Leu Arg Glu Glu Tyr Leu Glu Arg Asp Ser Ile Ala Ile Ser Ala
                355                 360                 365

Tyr Ala Met Asn His Gly Tyr Val Asp Ile Gln Val Ala Ser Pro Glu
        370                 375                 380

Val Thr Phe Asn Glu Lys Gly Ile Val Ile Thr Phe Arg Val Lys Glu
385                 390                 395                 400

Gly Lys Arg Tyr Lys Ile Gly Lys Ile Asp Phe Lys Gly Asp Leu Ile
                405                 410                 415

Glu Thr Asn Glu Gln Leu Leu Lys Val Thr Lys Ile Asp Asp His Lys
        420                 425                 430

Asn Tyr Glu Gln Tyr Phe Ser Leu Ser Val Met Gln Asp Asp Val Lys
        435                 440                 445

Ala Leu Thr Asp Phe Tyr Ser Asp Tyr Gly Tyr Ala Phe Ala Glu Val
        450                 455                 460

Asp Leu Glu Thr Thr Lys Asn Glu Glu Asp Ala Thr Ile Asp Val Thr
465                 470                 475                 480

Phe Leu Ile Asp Lys Lys Gln Lys Val Phe Leu Arg Arg Ile Ile Val
                485                 490                 495

Glu Gly Asn Thr Arg Thr Arg Asp Asn Val Ile Leu Arg Glu Leu Arg
                500                 505                 510

Leu Ala Asp Gly Asp Leu Phe Asn Gly Gln His Leu Arg Arg Ser Asn
                515                 520                 525

Glu Cys Leu Asn Arg Leu Gly Tyr Phe Asn Gln Val Asp Thr Asp Thr
        530                 535                 540

Leu Pro Thr Gly Lys Asp Asp Glu Val Asp Leu Leu Val Lys Val Gln
545                 550                 555                 560

Glu Ala Arg Thr Gly Ala Ile Thr Gly Gly Val Gly Tyr Ser Thr His
                565                 570                 575

Ser Lys Phe Gly Val Ser Gly Ser Ile Ser Glu Arg Asn Leu Trp Gly
        580                 585                 590

Lys Gly Tyr Ile Leu Ser Ile Gly Phe Ile Ser Ser Lys Ser Ser
        595                 600                 605

Ser Leu Asp Leu Ser Phe Thr Asn Pro Arg Val Tyr Asp Thr Asp Phe
        610                 615                 620

Gly Phe Ser Asn Asn Ile Tyr Thr Leu Arg Asp Glu Trp Asp Asp Phe
625                 630                 635                 640

Arg Lys Lys Thr Tyr Gly Asp Thr Ile Arg Leu Phe His Pro Ile Gly
                645                 650                 655

Glu Tyr Ser Ser Ile Phe Val Gly Tyr Arg Ile Asp Gln Tyr Arg Leu
                660                 665                 670

Tyr Asp Ile Pro Ser Thr Ala Pro Arg Ser Tyr Leu Asp Tyr Gln Gly

-continued

```
                675                 680                 685
Lys Asn Ile Ser Ser Val Val Ser Gly Gly Phe Thr Phe Asp Ser Thr
            690                 695                 700

Asp Ser Arg Glu Arg Pro Ser Lys Gly His Ile Ala Lys Leu Ile Val
705                 710                 715                 720

Glu Tyr Gly Gly Gly Leu Gly Gly Asn Asp Asn Phe Phe Lys Pro
                725                 730                 735

Ile Ala Glu Leu Gln Gly Phe Tyr Ser Ile Ser Arg Ser Lys Asn His
            740                 745                 750

Ile Ile His Trp Arg Thr Arg Ala Gly Ala Ala Tyr Lys Asn Ser Lys
            755                 760                 765

Lys Pro Val Pro Val Phe Asp Arg Phe Phe Ile Gly Gly Ile Asp Ser
770                 775                 780

Ile Arg Gly Tyr Asp Thr Glu Asp Leu Ala Pro Lys Asp Pro Arg Phe
785                 790                 795                 800

Gly Asp Glu Ile Gly Gly Asp Arg Met Ala Phe Leu Asn Leu Glu Tyr
                805                 810                 815

Ile Trp Thr Phe Gln Pro Glu Leu Gly Leu Ala Leu Val Pro Phe Tyr
            820                 825                 830

Asp Ile Gly Phe Gln Thr Asp Ser Val Gln Thr Ser Asn Pro Phe Ser
            835                 840                 845

Lys Leu Lys Gln Ser Tyr Gly Leu Glu Leu Arg Trp Arg Ser Pro Met
850                 855                 860

Gly Asp Leu Arg Phe Ala Tyr Gly Ile Pro Leu Asn Lys Asn Val Ser
865                 870                 875                 880

Gly Lys Lys Thr Arg Gly Arg Phe Glu Phe Ser Met Gly Gln Phe Phe
                885                 890                 895

<210> SEQ ID NO 6
<211> LENGTH: 812
<212> TYPE: PRT
<213> ORGANISM: Lawsonia intracellularis

<400> SEQUENCE: 6

Met Lys Gln Val Ile Ser Phe Asp Met Lys Lys Phe Leu Asn Ile
1               5                   10                  15

Val Ile Phe Cys Phe Gly Ile Ile Leu Leu Ser Ile Ile Gly Leu Ile
                20                  25                  30

Gly Leu Tyr Phe Trp Val Ser Arg Asp Leu Pro Asn Ile Thr Lys Leu
            35                  40                  45

Asn Asp Tyr Arg Pro Ala Leu Val Thr Thr Val Leu Ala Arg Asp Gly
    50                  55                  60

Thr Leu Ile Gly Tyr Ile Tyr Arg Glu Lys Arg Phe Leu Ile Pro Leu
65                  70                  75                  80

Ser Glu Met Ser Pro Phe Leu Pro Lys Ala Phe Leu Ala Ala Glu Asp
                85                  90                  95

Ala Glu Phe Tyr Glu His Glu Gly Val Asn Pro Leu Ala Ile Ile Arg
            100                 105                 110

Ala Phe Leu Ile Asn Leu Gln Ser Gly Thr Thr Arg Gln Gly Gly Ser
        115                 120                 125

Thr Ile Thr Gln Gln Val Ile Lys Arg Leu Leu Ser Pro Glu Arg
    130                 135                 140

Ser Tyr Glu Arg Lys Ile Lys Glu Ala Ile Leu Ala Tyr Arg Leu Glu
145                 150                 155                 160
```

```
Lys Tyr Leu Ser Lys Asp Glu Ile Leu Thr Ile Tyr Leu Asn Gln Thr
            165                 170                 175

Phe Leu Gly Ala His Ser Tyr Gly Val Glu Ala Ala Arg Thr Tyr
            180                 185             190

Phe Ala Lys His Ala Lys Asp Leu Ser Leu Ala Glu Cys Ala Leu Leu
            195                 200                 205

Ala Gly Leu Pro Gln Ala Pro Ser Arg Tyr Asn Pro Tyr Lys Asp Pro
210                 215                 220

Glu Ala Ala Lys Ile Arg Gln Arg Tyr Ala Leu Arg Arg Leu His Asp
225                 230                 235                 240

Val Gly Trp Ile Thr Gln Ala Glu Tyr Glu Ala Leu Gln Glu Pro
                245                 250                 255

Leu Tyr Phe Ser Ser Met Lys Glu Gly Leu Gly Ala Glu Ser Ser Trp
            260                 265                 270

Tyr Met Glu Glu Val Arg Lys Gln Leu Val Ser Phe Leu Ser Lys Glu
            275                 280                 285

Asn Ile Ser Gln Tyr Gly Ile Val Leu Pro Leu Tyr Gly Glu Asp Ala
290                 295                 300

Leu Tyr Glu Leu Gly Phe Thr Ile Gln Thr Ala Met Asp Pro Gln Ala
305                 310                 315                 320

Gln Leu Val Ala Tyr Asp Val Leu Arg Asn Gly Leu Glu Asn Phe Ser
            325                 330                 335

Lys Arg Gln Gly Trp Lys Gly Pro Ile Glu His Ile Ser Ser Thr Met
            340                 345                 350

Ile Gln His Tyr Leu Glu Asn Ala Thr Phe Thr Pro Glu Lys Leu Asp
            355                 360                 365

Gly Gly Ala Trp Ala Lys Ala Ile Val Ser Lys Val Ser Gln Glu Gly
            370                 375                 380

Ala Glu Val Phe Leu Ser Ser Ile Tyr Lys Gly Phe Val Ser Val Glu
385                 390                 395                 400

Thr Met Gly Trp Ala Arg Lys Pro Asn Pro Glu Val Arg Ser Ala Tyr
            405                 410                 415

Cys Ala Pro Ile Lys Asp Ala Arg Ser Val Leu Asn Pro Gly Asp Ile
            420                 425                 430

Ile Trp Val Ser Gly Val Gly Pro Asp Ser Thr His Arg Tyr Ser Ser
            435                 440                 445

Lys Thr Leu Asp Thr Ser Lys Pro Ile Pro Leu Ala Leu Gln Gln Leu
            450                 455                 460

Pro Gln Ile Gln Gly Ala Leu Ile Ser Ile Glu Pro Asn Thr Gly Asp
465                 470                 475                 480

Val Ile Ala Met Ile Gly Gly Tyr Glu Phe Gly Lys Ser Gln Phe Asn
            485                 490                 495

Arg Ala Val Gln Ala Met Arg Gln Pro Gly Ser Ala Phe Lys Pro Ile
            500                 505                 510

Val Tyr Ser Ala Ala Leu Asp His Asp Tyr Thr Ser Ala Thr Met Val
            515                 520                 525

Leu Asp Ala Pro Ile Val Glu Phe Met Glu Ser Gly Asp Ile Trp Arg
530                 535                 540

Pro Gly Asn Tyr Glu Lys Asn Phe Lys Gly Pro Met Leu Phe Ser Asn
545                 550                 555                 560

Ala Leu Ala Leu Ser Arg Asn Leu Cys Thr Val Arg Ile Ala Gln Ser
            565                 570                 575

Ile Gly Leu Pro Ala Val Ile Glu Arg Ala Lys Ala Leu Gly Phe Asn
```

```
                    580                 585                 590
Gly Asn Phe Pro Glu Phe Phe Ser Ile Ser Leu Gly Ala Val Glu Val
                595                 600                 605
Thr Pro Ile Arg Leu Val Asn Ala Tyr Thr Ala Phe Ala Asn Gly Gly
            610                 615                 620
Asn Leu Ala Thr Pro Arg Phe Ile Leu Ser Ile Lys Asp Ser Asn Asn
625                 630                 635                 640
Thr Val Ile Tyr Arg Gln Glu Ile Glu Gln His Pro Val Ile Ser Pro
                645                 650                 655
Gln Asn Ala Tyr Ile Met Ala Ser Leu Leu Lys Asn Val Val Asn Ile
                660                 665                 670
Gly Thr Ala Arg Lys Ala Lys Val Leu Glu Arg Pro Leu Ala Gly Lys
                675                 680                 685
Thr Gly Thr Thr Asn Gly Glu His Asp Ala Trp Phe Ile Gly Phe Thr
            690                 695                 700
Pro Tyr Leu Val Thr Gly Val Tyr Val Gly Asn Asp His Pro Gln Thr
705                 710                 715                 720
Leu Gly Lys Asp Gly Thr Gly Ala Val Ala Ala Leu Pro Ile Phe Thr
                725                 730                 735
Glu Tyr Ser Lys Val Val Leu Lys Lys Tyr Pro Glu Ser Asp Phe Pro
                740                 745                 750
Val Pro Asp Gly Ile Thr Phe Ala Ser Ile Asp Thr Gln Thr Gly Asn
                755                 760                 765
Arg Ala Thr Ala Asn Ser Thr Asn Ser Val Val Leu Pro Phe Tyr Val
770                 775                 780
Gly Thr Val Pro Glu Tyr Phe Asp Ser Lys Asp Asn Glu Val Asn Thr
785                 790                 795                 800
Ile Glu Arg Gly Glu Asp Leu Leu Lys Gln Phe Phe
                805                 810

<210> SEQ ID NO 7
<211> LENGTH: 474
<212> TYPE: PRT
<213> ORGANISM: Lawsonia intracellularis

<400> SEQUENCE: 7

Met Phe Cys Lys Leu Lys Val Ile Ile Cys Ile Thr Leu Met Phe Ile
1               5                   10                  15
Ile Thr Val Val Pro Thr Ile Ala Glu Ser Ala Leu Pro Asn Phe Val
                20                  25                  30
Pro Leu Val Lys Asp Ala Ser Lys Ala Val Val Asn Ile Ser Thr Glu
            35                  40                  45
Lys Lys Ile Pro Arg Gly Arg Thr Glu Phe Pro Met Glu Met Phe Arg
        50                  55                  60
Gly Leu Pro Pro Gly Phe Glu Arg Phe Phe Gln Phe Glu Pro Lys
65                  70                  75                  80
Gly Pro Asp Ser Gln Ile His Lys Gln Arg Ser Leu Gly Thr Gly Phe
                85                  90                  95
Ile Ile Ser Ser Asp Gly Tyr Ile Val Thr Asn Asn His Val Ile Glu
                100                 105                 110
Gly Ala Asp Ser Val Arg Val Asn Leu Glu Gly Thr Ser Gly Lys Glu
            115                 120                 125
Glu Ser Leu Pro Ala Glu Val Ile Gly Arg Asp Glu Glu Thr Asp Leu
        130                 135                 140
```

-continued

```
Ala Leu Leu Lys Val Lys Ser Lys Asp Ser Leu Pro Tyr Leu Ile Phe
145                 150                 155                 160

Gly Asn Ser Asp Thr Met Glu Val Gly Glu Trp Val Leu Ala Ile Gly
            165                 170                 175

Asn Pro Phe Gly Leu Gly His Thr Val Thr Ala Gly Ile Leu Ser Ala
                180                 185                 190

Lys Gly Arg Asp Ile His Ala Gly Pro Phe Asp Asn Phe Leu Gln Thr
            195                 200                 205

Asp Ala Ser Ile Asn Pro Gly Asn Ser Gly Pro Leu Ile Asn Met
210                 215                 220

Ser Gly Gln Val Val Gly Ile Asn Thr Ala Ile Met Ala Ser Gly Gln
225                 230                 235                 240

Gly Ile Gly Phe Ala Ile Pro Ser Ser Met Ala Asp Arg Ile Ile Glu
                245                 250                 255

Gln Leu Lys Thr Asn Lys Lys Val Ser Arg Gly Trp Ile Gly Val Thr
            260                 265                 270

Ile Gln Asp Val Asp Thr Asn Thr Ala Lys Ala Leu Gly Leu Ser Gln
            275                 280                 285

Ala Lys Gly Ala Leu Val Gly Ser Val Pro Gly Asp Pro Ala Asp
290                 295                 300

Lys Ala Gly Leu Lys Val Gly Asp Ile Val Thr Gln Ala Asp Gly Lys
305                 310                 315                 320

Gln Ile Asp Ser Ala Ser Ser Leu Leu Lys Ala Ile Ala Thr Lys Pro
            325                 330                 335

Pro Phe Ser Val Val Lys Leu Lys Val Trp Arg Asp Gly Lys Ser Lys
            340                 345                 350

Asp Ile Ser Ile Thr Leu Gly Glu Arg Lys Thr Thr Ser Ser Gln Lys
            355                 360                 365

Gln Ser Ser Pro Glu Ser Leu Pro Gly Ala Leu Gly Leu Ser Val Arg
            370                 375                 380

Pro Leu Thr Gln Glu Glu Ser Lys Ser Phe Asp Val Lys Leu Gly Ile
385                 390                 395                 400

Gly Leu Leu Val Val Ser Val Glu Pro Asn Lys Pro Ala Ser Glu Ala
                405                 410                 415

Gly Ile Arg Glu Gln Asp Ile Ile Leu Ser Ala Asn Leu Lys Pro Leu
            420                 425                 430

Gln Ser Ala Asp Asp Leu Ala Asn Ile Ile Cys Gly Asp Ala Lys Lys
            435                 440                 445

Lys Gly Val Ile Met Leu Gln Leu Gln Arg Asn Gly Gln Thr Phe Phe
450                 455                 460

Lys Thr Leu Ser Leu Thr Glu Asp Ser Asn
465                 470
```

<210> SEQ ID NO 8
<211> LENGTH: 82
<212> TYPE: PRT
<213> ORGANISM: Lawsonia intracellularis

<400> SEQUENCE: 8

```
Met Cys His Ala Ile Pro Val Lys Val Ile Glu Leu Leu Asp Asn Asp
1               5                   10                  15

Ile Ile Arg Ala Thr Val Gly Asp Ser Thr Thr Ile Leu Thr Val Ser
            20                  25                  30

Gly Met Leu Leu Pro Glu Pro Val Thr Val Gly Asp Tyr Ile Ile Val
            35                  40                  45
```

-continued

His Ala Gly Phe Ala Ile His Lys Leu Glu Ala Thr Glu Ala Glu Glu
        50                  55                  60

Ser Leu Arg Leu Phe Arg Glu Leu Ser Ile Ala Val Gly Asp Thr Pro
65                  70                  75                  80

Asn Phe

<210> SEQ ID NO 9
<211> LENGTH: 177
<212> TYPE: PRT
<213> ORGANISM: Lawsonia intracellularis

<400> SEQUENCE: 9

Glu Phe Gln Leu Gly Ala Leu Asp Asp Leu Pro Phe Glu Asp Glu Ser
1               5                   10                  15

Phe Asn Tyr Ala Ser Leu Val Thr Ile Leu Glu Tyr Val Glu Asp Pro
            20                  25                  30

Lys Lys Ile Leu Ala Glu Ala Phe Arg Val Ala Ser Asp Gly Ile Ile
        35                  40                  45

Val Gly Phe Thr Asn Lys Trp Ser Ile Asn His Ile Ile Asn Ser Thr
    50                  55                  60

Leu Gln Leu Leu His Lys Lys Pro Lys Lys Asp Ser Gln Trp Val Ser
65                  70                  75                  80

Pro Trp Gln Leu Ile Arg Leu Thr Lys Gln Leu Tyr Pro Glu Cys Arg
                85                  90                  95

Ile Tyr Cys Arg Ser Thr Leu Leu Gly Pro Lys Arg Thr Trp Asp Val
            100                 105                 110

Thr Ser Ser Trp Ser Lys Leu Asn Arg Ile Ile Leu Ser Phe Pro Ile
        115                 120                 125

Gly Thr Tyr Val Gly Met Arg Ile Glu Lys Arg Pro Lys Pro Thr Leu
    130                 135                 140

Thr Pro Leu Leu Leu Lys Ala Lys Glu Gln Ala Val Asn Val Tyr Asn
145                 150                 155                 160

Ala Leu Ser Pro Glu Ala Thr Ser Thr Ile Gln His Asn Arg Thr Asn
                165                 170                 175

Lys

<210> SEQ ID NO 10
<211> LENGTH: 20
<212> TYPE: DNA
<213> ORGANISM: Lawsonia intracellularis

<400> SEQUENCE: 10
agagtctggg ccaactccag                                            20

<210> SEQ ID NO 11
<211> LENGTH: 20
<212> TYPE: DNA
<213> ORGANISM: Lawsonia intracellularis

<400> SEQUENCE: 11
tacaccctat cttgttacag                                            20

<210> SEQ ID NO 12
<211> LENGTH: 20
<212> TYPE: DNA
<213> ORGANISM: Lawsonia intracellularis

<400> SEQUENCE: 12

-continued aacttgcctc aatatttgag    20

<210> SEQ ID NO 13
<211> LENGTH: 20
<212> TYPE: DNA
<213> ORGANISM: Lawsonia intracellularis

<400> SEQUENCE: 13
tccatctcta gcaagaactg    20

<210> SEQ ID NO 14
<211> LENGTH: 20
<212> TYPE: DNA
<213> ORGANISM: Lawsonia intracellularis

<400> SEQUENCE: 14
ttcttgccta ccgtctagag    20

<210> SEQ ID NO 15
<211> LENGTH: 20
<212> TYPE: DNA
<213> ORGANISM: Lawsonia intracellularis

<400> SEQUENCE: 15
ataccaactt gattcagctc    20

<210> SEQ ID NO 16
<211> LENGTH: 20
<212> TYPE: DNA
<213> ORGANISM: Lawsonia intracellularis

<400> SEQUENCE: 16
aacttgggtt tactatccag    20

<210> SEQ ID NO 17
<211> LENGTH: 20
<212> TYPE: DNA
<213> ORGANISM: Lawsonia intracellularis

<400> SEQUENCE: 17
aatgaggcaa ccaggttctg    20

<210> SEQ ID NO 18
<211> LENGTH: 20
<212> TYPE: DNA
<213> ORGANISM: Lawsonia intracellularis

<400> SEQUENCE: 18
attaccaaca taaacacctg    20

<210> SEQ ID NO 19
<211> LENGTH: 20
<212> TYPE: DNA
<213> ORGANISM: Lawsonia intracellularis

<400> SEQUENCE: 19
caaggatact aacttgcctc    20

<210> SEQ ID NO 20
<211> LENGTH: 20
<212> TYPE: DNA
<213> ORGANISM: Lawsonia intracellularis

```
<400> SEQUENCE: 20
atttcttgaa agtgcaagag                                                 20

<210> SEQ ID NO 21
<211> LENGTH: 20
<212> TYPE: DNA
<213> ORGANISM: Lawsonia intracellularis

<400> SEQUENCE: 21
tcctgctgat aaggctggtc                                                 20

<210> SEQ ID NO 22
<211> LENGTH: 20
<212> TYPE: DNA
<213> ORGANISM: Lawsonia intracellularis

<400> SEQUENCE: 22
aaatcttgaa ggtacctcag                                                 20

<210> SEQ ID NO 23
<211> LENGTH: 20
<212> TYPE: DNA
<213> ORGANISM: Lawsonia intracellularis

<400> SEQUENCE: 23
tgtcttacgc tctcctagtg                                                 20

<210> SEQ ID NO 24
<211> LENGTH: 20
<212> TYPE: DNA
<213> ORGANISM: Lawsonia intracellularis

<400> SEQUENCE: 24
tccaacagtt actggttctg                                                 20

<210> SEQ ID NO 25
<211> LENGTH: 19
<212> TYPE: DNA
<213> ORGANISM: Lawsonia intracellularis

<400> SEQUENCE: 25
acaaagcagc tttatcctg                                                  19

<210> SEQ ID NO 26
<211> LENGTH: 20
<212> TYPE: DNA
<213> ORGANISM: Lawsonia intracellularis

<400> SEQUENCE: 26
ttcatttggg cccatatgac                                                 20

<210> SEQ ID NO 27
<211> LENGTH: 20
<212> TYPE: DNA
<213> ORGANISM: Lawsonia intracellularis

<400> SEQUENCE: 27
cagaataaca atgttgtcag                                                 20

<210> SEQ ID NO 28
<211> LENGTH: 20
<212> TYPE: DNA
<213> ORGANISM: Lawsonia intracellularis
```

```
<400> SEQUENCE: 28
attacgcctt gctgatggag                                                20

<210> SEQ ID NO 29
<211> LENGTH: 20
<212> TYPE: DNA
<213> ORGANISM: Lawsonia intracellularis

<400> SEQUENCE: 29
tcgaattgat caatatcgtc                                                20

<210> SEQ ID NO 30
<211> LENGTH: 20
<212> TYPE: DNA
<213> ORGANISM: Lawsonia intracellularis

<400> SEQUENCE: 30
agtatatttg gacattccag                                                20

<210> SEQ ID NO 31
<211> LENGTH: 20
<212> TYPE: DNA
<213> ORGANISM: Lawsonia intracellularis

<400> SEQUENCE: 31
aagataagag cgtggtgctg                                                20

<210> SEQ ID NO 32
<211> LENGTH: 20
<212> TYPE: DNA
<213> ORGANISM: Lawsonia intracellularis

<400> SEQUENCE: 32
tgtttcaaga tctacttcag                                                20

<210> SEQ ID NO 33
<211> LENGTH: 25
<212> TYPE: DNA
<213> ORGANISM: Lawsonia intracellularis

<400> SEQUENCE: 33
caacgtggat ccgaattcaa gcttc                                          25

<210> SEQ ID NO 34
<211> LENGTH: 25
<212> TYPE: DNA
<213> ORGANISM: Lawsonia intracellularis

<400> SEQUENCE: 34
ctatctatta taggactaat aggtc                                          25

<210> SEQ ID NO 35
<211> LENGTH: 29
<212> TYPE: DNA
<213> ORGANISM: Lawsonia intracellularis

<400> SEQUENCE: 35
ggatgaaaca ggttatcagc tttgacatg                                      29

<210> SEQ ID NO 36
<211> LENGTH: 25
<212> TYPE: DNA
```

-continued

<213> ORGANISM: Lawsonia intracellularis

<400> SEQUENCE: 36
ggtctttatt tttgggttag tagag 25

<210> SEQ ID NO 37
<211> LENGTH: 31
<212> TYPE: DNA
<213> ORGANISM: Lawsonia intracellularis

<400> SEQUENCE: 37
cagcatcaga aactgtgaaa gaatgttttg c 31

<210> SEQ ID NO 38
<211> LENGTH: 23
<212> TYPE: DNA
<213> ORGANISM: Lawsonia intracellularis

<400> SEQUENCE: 38
ggatatttag ttatgacaga ttg 23

<210> SEQ ID NO 39
<211> LENGTH: 24
<212> TYPE: DNA
<213> ORGANISM: Lawsonia intracellularis

<400> SEQUENCE: 39
ggcatcatta ggtttatgaa gtcg 24

<210> SEQ ID NO 40
<211> LENGTH: 25
<212> TYPE: DNA
<213> ORGANISM: Lawsonia intracellularis

<400> SEQUENCE: 40
gttagtgtag agactatggg ttggg 25

<210> SEQ ID NO 41
<211> LENGTH: 26
<212> TYPE: DNA
<213> ORGANISM: Lawsonia intracellularis

<400> SEQUENCE: 41
ccttaaagta acaaaaattg atgatc 26

<210> SEQ ID NO 42
<211> LENGTH: 20
<212> TYPE: DNA
<213> ORGANISM: Lawsonia intracellularis

<400> SEQUENCE: 42
gtaagctagg ataggtatcc 20

<210> SEQ ID NO 43
<211> LENGTH: 22
<212> TYPE: DNA
<213> ORGANISM: Lawsonia intracellularis

<400> SEQUENCE: 43
ggtgcttgat gcacctatag ta 22

<210> SEQ ID NO 44
<211> LENGTH: 22

```
<212> TYPE: DNA
<213> ORGANISM: Lawsonia intracellularis

<400> SEQUENCE: 44
tgccatacta cttgggatag cg                                              22

<210> SEQ ID NO 45
<211> LENGTH: 27
<212> TYPE: DNA
<213> ORGANISM: Lawsonia intracellularis

<400> SEQUENCE: 45
gctcaccaga atctttacca ggtgctc                                         27

<210> SEQ ID NO 46
<211> LENGTH: 26
<212> TYPE: DNA
<213> ORGANISM: Lawsonia intracellularis

<400> SEQUENCE: 46
gtttcaagtc cttcaattcg gacatc                                          26

<210> SEQ ID NO 47
<211> LENGTH: 26
<212> TYPE: DNA
<213> ORGANISM: Lawsonia intracellularis

<400> SEQUENCE: 47
gttttagctt ttattgtttc aagtcc                                          26

<210> SEQ ID NO 48
<211> LENGTH: 20
<212> TYPE: DNA
<213> ORGANISM: Lawsonia intracellularis

<400> SEQUENCE: 48
aggtgcaatc acaggtggtg                                                 20

<210> SEQ ID NO 49
<211> LENGTH: 20
<212> TYPE: DNA
<213> ORGANISM: Lawsonia intracellularis

<400> SEQUENCE: 49
gagtttagag aatgggttag                                                 20

<210> SEQ ID NO 50
<211> LENGTH: 21
<212> TYPE: DNA
<213> ORGANISM: Lawsonia intracellularis

<400> SEQUENCE: 50
ttggtacagc aagaaaagca a                                               21

<210> SEQ ID NO 51
<211> LENGTH: 21
<212> TYPE: DNA
<213> ORGANISM: Lawsonia intracellularis

<400> SEQUENCE: 51
atctgaagaa atgattaaac c                                               21

<210> SEQ ID NO 52
```

```
<211> LENGTH: 20
<212> TYPE: DNA
<213> ORGANISM: Lawsonia intracellularis

<400> SEQUENCE: 52
actaaaatat cctaattccc                                              20

<210> SEQ ID NO 53
<211> LENGTH: 22
<212> TYPE: DNA
<213> ORGANISM: Lawsonia intracellularis

<400> SEQUENCE: 53
ttgagctaaa tattgctgta ac                                           22

<210> SEQ ID NO 54
<211> LENGTH: 21
<212> TYPE: DNA
<213> ORGANISM: Lawsonia intracellularis

<400> SEQUENCE: 54
tgcccattct atgggacgct g                                            21

<210> SEQ ID NO 55
<211> LENGTH: 29
<212> TYPE: DNA
<213> ORGANISM: Lawsonia intracellularis

<400> SEQUENCE: 55
ggtataccag caataagagc tttcattgc                                    29

<210> SEQ ID NO 56
<211> LENGTH: 22
<212> TYPE: DNA
<213> ORGANISM: Lawsonia intracellularis

<400> SEQUENCE: 56
ggggatgcta agaagaaagg gg                                           22

<210> SEQ ID NO 57
<211> LENGTH: 21
<212> TYPE: DNA
<213> ORGANISM: Lawsonia intracellularis

<400> SEQUENCE: 57
agtttggtaa ggcactttct g                                            21

<210> SEQ ID NO 58
<211> LENGTH: 20
<212> TYPE: DNA
<213> ORGANISM: Lawsonia intracellularis

<400> SEQUENCE: 58
gaaagtgact ttcctgttcc                                              20

<210> SEQ ID NO 59
<211> LENGTH: 20
<212> TYPE: DNA
<213> ORGANISM: Lawsonia intracellularis

<400> SEQUENCE: 59
ttaggtgctc attcttatgg                                              20
```

```
<210> SEQ ID NO 60
<211> LENGTH: 18
<212> TYPE: DNA
<213> ORGANISM: Lawsonia intracellularis

<400> SEQUENCE: 60
tcctttccaa ccttgtcg                                                   18

<210> SEQ ID NO 61
<211> LENGTH: 22
<212> TYPE: DNA
<213> ORGANISM: Lawsonia intracellularis

<400> SEQUENCE: 61
gatacaagag ggtaaaagtt tg                                              22

<210> SEQ ID NO 62
<211> LENGTH: 22
<212> TYPE: DNA
<213> ORGANISM: Lawsonia intracellularis

<400> SEQUENCE: 62
cttattcgtc taacaaagca gc                                              22

<210> SEQ ID NO 63
<211> LENGTH: 32
<212> TYPE: DNA
<213> ORGANISM: Lawsonia intracellularis

<400> SEQUENCE: 63
cgaccatgga acaggttatc agctttgaca tg                                   32

<210> SEQ ID NO 64
<211> LENGTH: 35
<212> TYPE: DNA
<213> ORGANISM: Lawsonia intracellularis

<400> SEQUENCE: 64
gggactagtt tttataatca gctacataaa aatgg                                35

<210> SEQ ID NO 65
<211> LENGTH: 33
<212> TYPE: DNA
<213> ORGANISM: Lawsonia intracellularis

<400> SEQUENCE: 65
cgaccatggc acaatatcta ttagaaaata tag                                  33

<210> SEQ ID NO 66
<211> LENGTH: 34
<212> TYPE: DNA
<213> ORGANISM: Lawsonia intracellularis

<400> SEQUENCE: 66
gggtctagac gttattacac agtaacagta gaag                                 34

<210> SEQ ID NO 67
<211> LENGTH: 30
<212> TYPE: DNA
<213> ORGANISM: Lawsonia intracellularis

<400> SEQUENCE: 67
aagccatggt agctgattat aaaaatggag                                      30
```

<210> SEQ ID NO 68
<211> LENGTH: 31
<212> TYPE: DNA
<213> ORGANISM: Lawsonia intracellularis

<400> SEQUENCE: 68
caccatatgg ccttaccaaa ctttgtaccc c                                31

<210> SEQ ID NO 69
<211> LENGTH: 27
<212> TYPE: DNA
<213> ORGANISM: Lawsonia intracellularis

<400> SEQUENCE: 69
caatcctggg aatgctggtg gtccatt                                     27

<210> SEQ ID NO 70
<211> LENGTH: 62
<212> TYPE: DNA
<213> ORGANISM: Lawsonia intracellularis

<400> SEQUENCE: 70
ggccatgggt accaccacca ccaccacctc tctggcttca aaagacgatc cttctattgt   60
gg                                                                62

<210> SEQ ID NO 71
<211> LENGTH: 35
<212> TYPE: DNA
<213> ORGANISM: Lawsonia intracellularis

<400> SEQUENCE: 71
ggccatggct tcaaaagacg atccttctat tgtgg                            35

<210> SEQ ID NO 72
<211> LENGTH: 27
<212> TYPE: DNA
<213> ORGANISM: Lawsonia intracellularis

<400> SEQUENCE: 72
ctaacgtaga catgagcaga gaaatgg                                     27

<210> SEQ ID NO 73
<211> LENGTH: 24
<212> TYPE: DNA
<213> ORGANISM: Lawsonia intracellularis

<400> SEQUENCE: 73
ggggtatata caatagatca cttg                                        24

<210> SEQ ID NO 74
<211> LENGTH: 28
<212> TYPE: DNA
<213> ORGANISM: Lawsonia intracellularis

<400> SEQUENCE: 74
ccataactac tgcactagga aatagatg                                    28

<210> SEQ ID NO 75
<211> LENGTH: 27
<212> TYPE: DNA
<213> ORGANISM: Lawsonia intracellularis

<400> SEQUENCE: 75

-continued

```
gcccattcta tgggacgctg ccttgag                                          27

<210> SEQ ID NO 76
<211> LENGTH: 27
<212> TYPE: DNA
<213> ORGANISM: Lawsonia intracellularis

<400> SEQUENCE: 76
gtaagctagg ataggtatcc ataacag                                          27

<210> SEQ ID NO 77
<211> LENGTH: 33
<212> TYPE: DNA
<213> ORGANISM: Lawsonia intracellularis

<400> SEQUENCE: 77
ggctctagag ttagttgcta tcttcagtta aag                                   33

<210> SEQ ID NO 78
<211> LENGTH: 32
<212> TYPE: DNA
<213> ORGANISM: Lawsonia intracellularis

<400> SEQUENCE: 78
ggctctagag tattaatata cctctaacaa gc                                    32

<210> SEQ ID NO 79
<211> LENGTH: 33
<212> TYPE: DNA
<213> ORGANISM: Lawsonia intracellularis

<400> SEQUENCE: 79
ggctctagag ttattagaag aattgcccca ttg                                   33

<210> SEQ ID NO 80
<211> LENGTH: 57
<212> TYPE: DNA
<213> ORGANISM: Lawsonia intracellularis

<400> SEQUENCE: 80
ggccatgggt accaccacca ccaccacctc tctgctattg ttaacagtaa atgaagg         57

<210> SEQ ID NO 81
<211> LENGTH: 35
<212> TYPE: DNA
<213> ORGANISM: Lawsonia intracellularis

<400> SEQUENCE: 81
ggctctagag ttaaatataa cctttccccc ataag                                 35

<210> SEQ ID NO 82
<211> LENGTH: 22
<212> TYPE: DNA
<213> ORGANISM: Lawsonia intracellularis

<400> SEQUENCE: 82
tacaaaatta acaataaaat ac                                               22

<210> SEQ ID NO 83
<211> LENGTH: 20
<212> TYPE: DNA
<213> ORGANISM: Lawsonia intracellularis
```

```
<400> SEQUENCE: 83
agaatgtatg atatcctctc                                              20

<210> SEQ ID NO 84
<211> LENGTH: 20
<212> TYPE: DNA
<213> ORGANISM: Lawsonia intracellularis

<400> SEQUENCE: 84
aggtattgga attgatcgac                                              20

<210> SEQ ID NO 85
<211> LENGTH: 20
<212> TYPE: DNA
<213> ORGANISM: Lawsonia intracellularis

<400> SEQUENCE: 85
ggagagtgga gagatatcag                                              20

<210> SEQ ID NO 86
<211> LENGTH: 20
<212> TYPE: DNA
<213> ORGANISM: Lawsonia intracellularis

<400> SEQUENCE: 86
ctaaactctt tgaccttgac                                              20

<210> SEQ ID NO 87
<211> LENGTH: 20
<212> TYPE: DNA
<213> ORGANISM: Lawsonia intracellularis

<400> SEQUENCE: 87
aaagtttgta ggtatatctc                                              20

<210> SEQ ID NO 88
<211> LENGTH: 20
<212> TYPE: DNA
<213> ORGANISM: Lawsonia intracellularis

<400> SEQUENCE: 88
aataagatac atgaggtgac                                              20

<210> SEQ ID NO 89
<211> LENGTH: 20
<212> TYPE: DNA
<213> ORGANISM: Lawsonia intracellularis

<400> SEQUENCE: 89
gcagttgaga gttaattctc                                              20

<210> SEQ ID NO 90
<211> LENGTH: 20
<212> TYPE: DNA
<213> ORGANISM: Lawsonia intracellularis

<400> SEQUENCE: 90
tccagaattt accatgtgtg                                              20

<210> SEQ ID NO 91
<211> LENGTH: 20
<212> TYPE: DNA
<213> ORGANISM: Lawsonia intracellularis
```

```
<400> SEQUENCE: 91
gatatgttgc ataggcccag                                              20

<210> SEQ ID NO 92
<211> LENGTH: 20
<212> TYPE: DNA
<213> ORGANISM: Lawsonia intracellularis

<400> SEQUENCE: 92
atagtatccc ataccatgac                                              20

<210> SEQ ID NO 93
<211> LENGTH: 20
<212> TYPE: DNA
<213> ORGANISM: Lawsonia intracellularis

<400> SEQUENCE: 93
tgcataacat tgaatgcgac                                              20

<210> SEQ ID NO 94
<211> LENGTH: 20
<212> TYPE: DNA
<213> ORGANISM: Lawsonia intracellularis

<400> SEQUENCE: 94
ctttaaatag agttcaggag                                              20

<210> SEQ ID NO 95
<211> LENGTH: 20
<212> TYPE: DNA
<213> ORGANISM: Lawsonia intracellularis

<400> SEQUENCE: 95
atagtatccc ataccatgac                                              20

<210> SEQ ID NO 96
<211> LENGTH: 20
<212> TYPE: DNA
<213> ORGANISM: Lawsonia intracellularis

<400> SEQUENCE: 96
ttccactttt caatggagtc                                              20

<210> SEQ ID NO 97
<211> LENGTH: 22
<212> TYPE: DNA
<213> ORGANISM: Lawsonia intracellularis

<400> SEQUENCE: 97
cccatggagg ttagaatagc aa                                           22

<210> SEQ ID NO 98
<211> LENGTH: 22
<212> TYPE: DNA
<213> ORGANISM: Lawsonia intracellularis

<400> SEQUENCE: 98
ggggaacgct acttaactta ag                                           22

<210> SEQ ID NO 99
<211> LENGTH: 24
<212> TYPE: DNA
```

-continued

<213> ORGANISM: Lawsonia intracellularis

<400> SEQUENCE: 99
gtaagtttac acgactacct attg                                             24

<210> SEQ ID NO 100
<211> LENGTH: 20
<212> TYPE: DNA
<213> ORGANISM: Lawsonia intracellularis

<400> SEQUENCE: 100
gctggacgta ttatctctct                                                  20

<210> SEQ ID NO 101
<211> LENGTH: 19
<212> TYPE: DNA
<213> ORGANISM: Lawsonia intracellularis

<400> SEQUENCE: 101
ttgtaggttc ttctatagg                                                   19

<210> SEQ ID NO 102
<211> LENGTH: 526
<212> TYPE: PRT
<213> ORGANISM: Lawsonia intracellularis

<400> SEQUENCE: 102

Leu Ile Gln Lys Lys Ser His Pro Pro Ile Lys Leu Ala Thr Lys
1               5                   10                  15

Ser Pro His Val Ser Tyr Phe Lys Pro Leu Leu Glu Ser Leu Ala Glu
                20                  25                  30

Lys Asn Glu Leu Asn Glu Val Ile Lys Asn Cys Val Val Lys Ser Cys
            35                  40                  45

Glu Leu Leu Asp Ser Gly Ile Pro Leu Tyr Pro Asp Glu Phe Val Lys
        50                  55                  60

Glu His Tyr Ala Gly Met Leu Arg Ala Glu Tyr Glu Ala Tyr Ser Ala
65                  70                  75                  80

Ser Glu Leu Glu Ser Leu Asp Glu Ile Phe Ala Cys Ala Gly Arg Ile
                85                  90                  95

Ile Ser Leu Arg Ser Phe Gly Lys Val Ile Phe Phe His Ile Met Asp
            100                 105                 110

Arg Ser Gly Arg Ile Gln Cys Tyr Ala Ser Arg Glu Asn Met Gly Glu
        115                 120                 125

Glu Ala Phe Ser Thr Phe Lys Lys Phe Asp Ile Gly Asp Ile Val Gly
    130                 135                 140

Val Asn Gly Lys Leu Phe Arg Thr Lys Met Gly Glu Leu Thr Leu Asn
145                 150                 155                 160

Cys Ser Thr Ile Thr Leu Leu Ala Lys Ser Phe Arg Ser Leu Pro Glu
                165                 170                 175

Lys His Asn Gly Leu Thr Asn Ile Glu Leu Arg Tyr Arg Gln Arg Tyr
            180                 185                 190

Ile Asp Leu Ile Val Asn Pro Lys Thr Arg Asp Ile Phe Arg Lys Arg
        195                 200                 205

Ser Lys Ile Ile His Glu Ile Arg Ala Phe Leu Glu Glu Asn Gly Phe
    210                 215                 220

Ile Glu Val Glu Thr Pro Ile Leu Gln Pro Ile Pro Gly Gly Ala Met
225                 230                 235                 240

-continued

```
Ala Arg Pro Phe Thr Thr His Asn Asn Ala Met Asp Met Thr Leu Tyr
                245                 250                 255
Met Arg Ile Ala Pro Glu Leu Tyr Leu Lys Arg Leu Leu Val Gly Gly
            260                 265                 270
Phe Glu Lys Leu Phe Glu Leu Asn Arg Ser Phe Arg Asn Glu Gly Ile
        275                 280                 285
Ser Ile Gln His Asn Pro Glu Phe Thr Met Cys Glu Phe Tyr Trp Ala
    290                 295                 300

Tyr Ala Thr Tyr Leu Asp Leu Met Glu Leu Thr Glu Glu Met Phe Ala
305                 310                 315                 320
Tyr Leu Thr Lys Lys Ile Cys Gly Thr Met Thr Ile Ser Tyr Gln Gly
                325                 330                 335
Asn Thr Ile Asp Phe Thr Pro Gly Thr Trp Gln Lys Tyr Thr Phe His
            340                 345                 350
Glu Ser Leu Glu Lys Ile Gly Gly His Ser Pro Glu Phe Tyr Asn Asn
        355                 360                 365
Phe Glu Lys Val Ser Glu Tyr Ile Lys Glu His Gly Glu Lys Val Leu
    370                 375                 380
Thr Thr Asp Lys Ile Gly Lys Leu Gln Ala Lys Leu Phe Asp Leu Asp
385                 390                 395                 400
Val Glu Asn Lys Leu Ile Gln Pro Thr Phe Ile Tyr His Tyr Pro Thr
                405                 410                 415
Asp Ile Ser Pro Leu Ser Lys Lys Asn Lys Asp Asn Pro Glu Val Thr
            420                 425                 430
Asp Arg Phe Glu Leu Phe Ile Ala Gly Lys Glu Ile Ala Asn Ala Phe
        435                 440                 445
Ser Glu Leu Asn Asp Pro Ile Asp Gln Arg Leu Arg Phe Glu Glu Gln
    450                 455                 460
Val Leu Glu Lys Ala Arg Gly Asp Glu Glu Ala Cys Pro Met Asp Glu
465                 470                 475                 480
Asp Tyr Leu Arg Ala Leu Glu Tyr Gly Met Pro Pro Ala Ala Gly Glu
                485                 490                 495
Gly Ile Gly Ile Asp Arg Leu Val Met Leu Leu Thr Asp Ser Pro Ser
            500                 505                 510
Ile Arg Glu Val Ile Leu Phe Pro Leu Leu Arg Thr Glu Arg
        515                 520                 525

<210> SEQ ID NO 103
<211> LENGTH: 11
<212> TYPE: PRT
<213> ORGANISM: Lawsonia intracellularis

<400> SEQUENCE: 103

Arg Gln Gly Gly Ser Thr Ile Thr Gln Gln Val
1               5                   10

<210> SEQ ID NO 104
<211> LENGTH: 21
<212> TYPE: PRT
<213> ORGANISM: Lawsonia intracellularis

<400> SEQUENCE: 104

Met Gly Ser Ser His His His His His His Ser Ser Gly Leu Val Pro
1               5                   10                  15

Arg Gly Ser His Met
            20
```

<210> SEQ ID NO 105
<211> LENGTH: 10
<212> TYPE: PRT
<213> ORGANISM: Lawsonia intracellularis

<400> SEQUENCE: 105

Met Gly Thr Thr Thr Thr Thr Thr Ser Leu
1               5                   10

<210> SEQ ID NO 106
<211> LENGTH: 9
<212> TYPE: PRT
<213> ORGANISM: Lawsonia intracellularis

<400> SEQUENCE: 106

Ala Ser Lys Asp Asp Pro Ser Ile Val
1               5

<210> SEQ ID NO 107
<211> LENGTH: 4
<212> TYPE: PRT
<213> ORGANISM: Lawsonia intracellularis

<400> SEQUENCE: 107

Ser Ala Phe Lys
1

<210> SEQ ID NO 108
<211> LENGTH: 4
<212> TYPE: PRT
<213> ORGANISM: Lawsonia intracellularis

<400> SEQUENCE: 108

Lys Thr Ser Gly
1

<210> SEQ ID NO 109
<211> LENGTH: 5
<212> TYPE: PRT
<213> ORGANISM: Lawsonia intracellularis

<400> SEQUENCE: 109

Gln Gly Ala Ser Thr
1               5

<210> SEQ ID NO 110
<211> LENGTH: 4
<212> TYPE: PRT
<213> ORGANISM: Lawsonia intracellularis
<220> FEATURE:
<221> NAME/KEY: misc_feature
<222> LOCATION: (2)..(3)
<223> OTHER INFORMATION: Xaa can be any naturally occurring amino acid

<400> SEQUENCE: 110

Ser Xaa Xaa Lys
1

<210> SEQ ID NO 111
<211> LENGTH: 4
<212> TYPE: PRT
<213> ORGANISM: Lawsonia intracellularis

```
<400> SEQUENCE: 111

Ser Ala Phe Lys
1

<210> SEQ ID NO 112
<211> LENGTH: 7
<212> TYPE: PRT
<213> ORGANISM: Lawsonia intracellularis

<400> SEQUENCE: 112

Ala Leu Pro Asn Phe Val Pro
1               5
```